(12) United States Patent
Tomar et al.

(10) Patent No.: US 9,778,194 B2
(45) Date of Patent: Oct. 3, 2017

(54) IN-SITU COMBINED SENSING OF UNIAXIAL NANOMECHANICAL AND MICROMECHANICAL STRESS WITH SIMULTANEOUS MEASUREMENT OF SURFACE TEMPERATURE PROFILES BY RAMAN SHIFT IN NANOSCALE AND MICROSCALE STRUCTURES

(71) Applicant: Purdue Research Foundation, West Lafayette, IN (US)

(72) Inventors: Vikas Tomar, West Lafayette, IN (US); Ming Gan, Shanghai (CN)

(73) Assignee: Purdue Research Foundation, West Lafayette, IN (US)

( * ) Notice: Subject to any disclaimer, the term of this patent is extended or adjusted under 35 U.S.C. 154(b) by 3 days.

(21) Appl. No.: 14/800,088

(22) Filed: Jul. 15, 2015

(65) Prior Publication Data
US 2016/0018334 A1    Jan. 21, 2016

Related U.S. Application Data

(60) Provisional application No. 62/025,223, filed on Jul. 16, 2014.

(51) Int. Cl.
*G01J 3/44* (2006.01)
*G01N 21/65* (2006.01)
(Continued)

(52) U.S. Cl.
CPC .............. *G01N 21/65* (2013.01); *G01K 13/00* (2013.01); *G01L 1/24* (2013.01)

(58) Field of Classification Search
CPC ... G01L 1/24; G01L 1/22; G01K 13/00; G01J 3/12; G01B 11/16; B82Y 30/00;
(Continued)

(56) References Cited

PUBLICATIONS

"Thermal Metrology of Polysilicon MEMS using Raman Spectroscopy", Georgia Institute of Technology, Aug. 2005 by Mark Richard Abel.*

(Continued)

*Primary Examiner* — Jamil Ahmed
(74) *Attorney, Agent, or Firm* — John V. Daniluck; Bingham Greenebaum Doll LLP

(57) ABSTRACT

Embodiments of the present disclosure include separating a measured Raman shift signal into mechanical and thermal components when a uniaxial compressive load is applied in situ. In some embodiments, in situ uniaxial compressive loads are applied on examined specimens from room temperature to 150° C. In alternate embodiments, Raman shift measurements are performed as a function of strain at constant temperature and/or as a function of temperature at constant strain levels. It was realized that the Raman shift measured at a given temperature under a given level of applied stress can be expressed as a summation of stress-induced Raman shift signal and temperature-induced Raman shift signal measured separately. Such a separation of Raman shift signal is utilized by various embodiments to measure localized change in thermal conductivity and/or mechanical stress of structures (e.g., semiconductor structures) under applied stress.

28 Claims, 49 Drawing Sheets

(51) Int. Cl.
*G01K 13/00* (2006.01)
*G01L 1/24* (2006.01)

(58) Field of Classification Search
CPC ........... B82Y 40/00; A61K 6/083; A61B 5/01; C04B 16/0675; G01N 21/65
See application file for complete search history.

(56) References Cited

PUBLICATIONS

Gan, Ming, et al., An in situ platform for the investigation of Raman shift in micro-scale silicon structures as a function of mechanical stress and temperature increase, Review of Scientific Instruments 85, 013902. Jan. 16, 2014.

* cited by examiner

IN-SITU COMBINED SENSING OF UNIAXIAL NANOMECHANICAL AND MICROMECHANICAL STRESS WITH SIMULTANEOUS MEASUREMENT OF SURFACE TEMPERATURE PROFILES BY RAMAN SHIFT IN NANOSCALE AND MICROSCALE STRUCTURES

This application claims the benefit of U.S. Provisional Application No. 62/025,223, filed Jul. 16, 2014, the entirety of which is hereby incorporated herein by reference.

GOVERNMENT RIGHTS

This invention was made with government support under CMMI-1131112 awarded by the National Science Foundation. The government has certain rights in the invention.

BACKGROUND

Microscale and nanoscale silicon structures form essential parts of current semiconductor processors, sensors, and MEMS devices. Microscale and nanoscale structures are typically no larger than a millimeter in any dimension, and typically include components no larger than 100 micrometers in size. Microscale and nanoscale structures described herein include MEMS (Micro-Electro-Mechanical Systems), which are typically made up of components between 1 to 100 micrometers in size (i.e. 0.001 to 0.1 mm), and generally range in overall size from 20 micrometers to a millimeter (i.e. 0.02 to 1.0 mm). Devices of this size are frequently characterized by having a relatively large surface area for its mass (sometimes referred to as having a large surface area to volume ratio), resulting in the surface effects of the device (e.g., electrostatic interaction and wetting) frequently dominating over the mass effects (e.g., inertia and thermal conductivity). The functioning of such devices has been found to be highly affected by their operating temperature. Such densely packaged devices generate considerable heat density during operation, which leads to temperature increase of device components. Associated differential thermal expansion leads to thermal stresses and, ultimately, device failure due to thermal stress induced fatigue induced by temperature cycling. The passage of heat in such structures depends upon thermal conductivity. At the microscale, it has been revealed using experiments and simulations that the thermal conductivity of silicon structures changes as a function of mechanical stress. Fundamentally, such analyses have shed new insights regarding the effect of atomic vibrations (thermal properties) on atomic displacements (stress/strain). Results suggest that the influence of stress related thermal property change can lead to a reduction in the passage of heat out of devices and, ultimately, accelerated device failure. Analyses so far have measured thermal properties at a fixed constant applied stress. However, analyses so far have not measured the effect of thermal property change while stress is being applied simultaneously in situ, and, vice versa. Such measurements can reveal new insights regarding the mechanism of thermal stress development as a function of temperature and the corresponding changes in thermal properties. It is useful to be able to measure thermal and mechanical properties simultaneously. Various embodiments of the present disclosure include to simultaneously measuring thermal shift and mechanical shift components in a microscale silicon cantilever structure using Raman spectroscopy.

There are numerous experimental methods available to measure stress distribution inside silicon micro-structures, such as X-ray diffraction (XRD) and cross-sectional transmission electron microscopy (XTEM). These methods have been used to investigate stress distributions in silicon devices. In silicon, the mechanical stress or strain affects Raman shift by changing the frequency of Raman modes. Compared with other available methods for thermal conductivity measurement, Raman spectroscopy is a non-destructive technique, requires minimal sample preparation, and has spatial resolution of less than 1 μm. This method is also suitable for the measurement of temperature distribution and thermal conductivity of silicon structures.

In Raman spectroscopy measurements, a focused laser spot on the sample surface creates localized temperature increase, which can be detected by the Raman spectroscopy system by knowing the temperature dependence of the Raman peak position. Using the corresponding heat transfer models, the Raman spectra can be related to the thermal conductivity. This approach is called Raman thermometry. This method can be applied to thin films deposited onto a thick substrate, with the thickness of the film at least one magnitude higher than the laser spot size. Besides being used for thin films with substrates, the micro-Raman method has also been used for suspended nanowires, suspended membranes, or membranes with support.

As discussed above, the Raman shift of silicon is affected by both applied mechanical stress and temperature. The measured Raman shift is a combination of these two, which creates difficulty for investigation of the relationship between mechanical stress and thermal conductivity. One method that may be used of investigate this relationship is based on Raman Stokes peak position and line width broadening. Using this method, the surface temperature of a polysilicon sample can be measured irrespective of stress state, but with a certain extent of uncertainty. Raman Stokes peak position has better accuracy than Stokes line width when used for temperature measurement.

Microscale silicon structures have been essential parts in micro-electromechanical systems (MEMS). In such applications, the silicon structures are commonly subject to temperatures ranging from 25° C. to 100° C. and stress levels of tens to hundreds of MPa. Various embodiments pertain to measurements of in-situ creep properties of silicon micro-cantilevers in this temperature range under uniaxial compressive stress. Several embodiments have been experimentally verified with a microscale mechanical loading platform and localized heating module. The results reveal that in the stress range of 50 MPa to 150 MPa, the strain rate of the silicon cantilever increases linearly as a function of applied stress. The strain rate also increases as a function of temperature increase. However, the strain rate increase slows down with increase in temperature. The strain rate of the microscale silicon cantilever ($0.2 \sim 2.5 \times 10^{-6}$ s$^{-1}$) was comparable to literature values for bulk silicon reported in temperature range 1100° C.~1300° C. but with one tenth of the applied stress level. However, the sensitivity of the strain rate change with respect to change in temperature or stress was found to be lower, compared with the literature values. It has been earlier revealed by different experiments that the near-surface atoms of the microscale silicon exhibit a relaxed state signified by lower surface stress values than bulk, especially at high temperature. The relaxation of the near-surface atoms also contributes to the creep of the material. As the temperature increases, the relaxation involves atoms deeper into the material surface, which contributes to the higher creep rate at higher temperature.

However, the increase rate in the atomic volume with respect to temperature increase reduces, contributing to reduction in the rate of strain rate increase with increase in creep temperature. The present experiments quantify the extent by measuring surface stress values during uniaxial temperature dependent creep.

The thermal conductivity of many solids and liquids is affected by mechanical stress/strain at small length scales of nanometer and micrometer. At the bulk scale, mechanical strain is mediated by line or point defects (such as dislocations and vacancies). The role of diffusion (motion of grain boundaries, interfaces) is negligible unless the temperature is comparable to the melting point. Since dislocations are sparse enough to not influence the mean free path and velocities of electrons and phonons, strain dependence of electrical and thermal transport at bulk scale is insignificant. However, at the nanoscale, the predominant mechanism becomes surface and interface (i.e., diffusion) mediated deformation. For example strain rate at nano- and microscale scales with the inverse cubic ($d^{-3}$) dependence of length-scale (d) using the following expression:

$$\dot{\varepsilon} = C \frac{D_{gb} G b}{k_B T} \left(\frac{b}{d}\right)^3 \left(\frac{\sigma}{G}\right). \tag{3-1}$$

Here, C is a constant; $D_{gb}$ is interface diffusion coefficient; G is the shear modulus; b is the Burger's vector; $k_B$ is the Boltzmann's constant; T is the absolute temperature; and a is the applied stress. The inverse cubic ($d^{-3}$) dependence of length-scale may induce diffusion even at the room temperature at the nanoscale. However diffusion mainly influences electric transport, not the thermal transport. Unlike dislocations (1D defects), surface and interfaces (2D defects) strongly scatter phonons and electrons at all temperatures. Because of the change in defect dimensionality (1D to 2D), the influence of strain on thermal scattering at the nanoscale and microscale can be expected to be 10 times higher than that at the bulk scale. The same conclusion can be drawn for thermal transport in super-lattices or heterostructures. Even stronger influence is expected because of the exponentially increasing surface to volume fraction at the nanoscale. Also, strain-induced phase transformation (improbable at bulk scale) may drastically change thermal conductivity. Various embodiments described herein use a nanomechanical Raman spectroscopy approach to analyze thermal conductivity of microscale Si cantilevers as a function of temperature.

Controlling the thermal conductivity of Si at the micro/nano-scale opens up opportunities for on-chip heat management and energy conservation of electronic devices. In silicon, phonons are the main energy carrier. Any constraint to the mean free path of the phonons will subsequently affect the thermal conductivity. Some examples of such a constraint are temperature change, grain boundary scattering, mechanical stress, and dopant atom scattering. In the case of bulk silicon, the thermal conductivity increases in the temperature range of 3 K to 30 K, then decreases as a function of temperature. In the temperature range of 300 K to 400 K, which covers the working temperature of most semiconductor devices, the thermal conductivity of bulk silicon is 150 w/m·K at 300 K and 110 w/m·K at 400 K.

Size effect can also significantly affect the thermal conductivity of silicon. At room temperature, it has been found that thermal conductivity of silicon films with the thickness of 1 μm is 10% less than that of bulk silicon; while for the silicon films with the thickness of 100 nm, the thermal conductivity is about half of the value for bulk silicon. The scale of the silicon structures in semiconductor devices is usually in microns or nanometers. This scale constraint brings challenge to the experimental measurement of thermal conductivity of silicon micro-structures. The experimental methods of thermal conductivity measurement at microscale include steady state method, 3ω method, photoacoustic/photothermal method, thermal microscopy method, time-domain thermal reflectance method, and micro-Raman method. Compared with other thermal conductivity measurement methods listed above, the micro-Raman setup discussed herein is open-path with high spatial resolution. It provides the space to the microscale loading module, which applies mechanical stress to the sample.

In Raman spectroscopy measurements, the focused laser spot on the sample surface creates localized temperature increase, which can be detected by the Raman spectroscopy system by knowing the temperature dependence of the Raman peak position. With corresponding heat transfer models, the Raman spectra can be related to the thermal conductivity of the material. This is the principle of the Raman thermometry. This method can be applied to thin films deposited onto a thick substrate, where the thickness of the film should be at least one magnitude higher than the laser spot size. In this way, the effect of the substrate can be neglected.

Drawbacks to prior systems/methods (e.g., prior AFM-Raman testing systems) include load ranges that are too low (e.g., a maximum load range approximately one mN (micro-Newton)) and the absence of uniaxial loading. Drawbacks to other prior systems (e.g., SEM-Raman testing systems) require specific testing conditions (e.g., generating a vacuum, generating an electron field, and destructive sample preparation), and do not provide uniaxial loading. Drawbacks to still other prior systems (e.g., TEM-Raman testing systems) require onerous sample preparation procedures, which frequently involve destructive sample preparation.

SUMMARY

Raman spectroscopy provides an accurate approach to measure temperature and stress in semiconductors at microscale and nanoscale. Embodiments of the present disclosure include an in situ experimentation-based approach to separate a measured room to high temperature Raman shift signal into mechanical and thermal components when a uniaxial compressive load is applied in situ. In situ uniaxial compressive loads can be applied on examined silicon cantilever specimens from room temperature to 150° C. Raman shift measurements can be performed as a function of strain at constant temperature and as a function of temperature at constant strain levels. It was realized that the Raman shift measured at a given temperature under a given level of applied stress can be expressed as a summation of stress-induced Raman shift signal and temperature-induced Raman shift signal measured separately. For silicon, the stress-induced Raman shift appears to be caused by inelastic interaction between the incident laser and the vibration of crystal lattice, while the temperature-induced Raman shift appears to be caused by the anharmonic terms in the vibrational potential energy. It was realized that such separation of Raman shift signal can be used to measure localized change in thermal conductivity and mechanical stress of semiconductor structures under applied stress.

Various embodiments of the present invention pertain to an analysis technique is presented to measure the Raman shift of silicon micro-beams due to applied compressive stress and temperature increase. The approach is based on separating the in situ Raman Stokes peak position induced by applied stress from the Raman Stokes peak position caused by temperature. Some embodiments include the amplification of a nanomechanical stress using an electromagnetic actuator installed in a nanoindentation system as a function of temperature. The in situ measurements are conducted with a nano-mechanical measurement setup that measures the stress and controls the temperature independent of the Raman setup.

Various other embodiments pertain to the thermal and mechanical properties of materials that are a function of the length scale of measurement. In the case of silicon (Si) length scale this dependent interrelationship of thermal and mechanical properties can be used to improve the thermal dissipation and performance of the microscale electronic devices. Still other embodiments a newly established nanomechanical Raman spectroscopy approach to analyze thermal conductivity of microscale Si cantilevers as a function of temperature and mechanical strain. The results show that the thermal conductivity of Si increases from 114 W/m·K to 145 W/m·K with compressive strain level increasing from 0% to 0.25% at room temperature. At higher temperatures, the dependence of thermal conductivity on strain significantly increases. Phonon mean free path shows an increase with uniaxial compression that is accompanied with free surface deformation but it shows decrease with increase in temperature. Analyses establish the notion that the phonon affected thermal conduction in Si is coupled to mechanical deformation at microscale where surface to volume ratio is high.

Advantages realized by embodiments of the present disclosure include no sample preparation, while other embodiments may require minimal sample preparation, which may include non-destructive sample preparation or sample preparation for surface roughness. Higher surface roughness can lower the density of the light being reflected from the surface, while at the same time higher surface roughness can make the angle adjustment less critical. It is desirable in some embodiments to have surface roughness of the sample less than the laser spot size, and in some embodiments the laser spot size is tens of microns or less. If the surface roughness is higher than the laser spot size, surface preparation may be needed with some embodiments of the present disclosure.

Other advantages realized by embodiments of the present disclosure include an ability to apply an increased load to the sample in comparison to other techniques. For example, the mechanical test module in some example embodiments can apply a load to the sample in the mili-Newton (mN) range, which his 2 to 3 magnitudes higher than typical AFM (Atomic Force Microscope) techniques. This increased load can be used to create stress/strain-induced mechanical/thermal property changes. Still other embodiments include mechanical test modules capable of applying uniaxial loading to the test sample.

Still further advantages realized by embodiments of the present disclosure include precise temperature control of the sample and/or the indenter from room temperature (approximately 20° C.) to 750° C. In some embodiments, the chamber in which the sample is enclosed is maintained at a temperature 3° C. higher than the temperature outside the chamber. The temperature within the sample chamber is precisely controlled to within +/−0.3° C. in some embodiments. The temperature outside the sample chamber is controlled to within +/−1° C. in some embodiments.

Yet other advantages realized by embodiments of the present disclosure include an ability to perform thermal conductivity measurements (e.g., direct thermal property measurements and/or stress-affected thermal property changes), which may be performed simultaneously with other tests (e.g., stress measurements) disclosed herein in some embodiments.

Additional advantages realized by embodiments of the present disclosure include the ability to use either nano-test heads and/or micro-test heads to perform measurements to investigate properties of the test samples at different scales.

Embodiments of the present disclosure utilize modulated parts and are capable of upgrading a device's measuring techniques with updated modules and integrating other measuring techniques with additional modules. Updates modules include modules capable of low temperature measurements (e.g., measurements as low as 100° K) and/or liquid imaging.

Various aspects of different embodiments of the present disclosure are expressed in paragraphs A1, A2, A3, A4, A5, A6, A7, A8, A9, A10, A11, A12, A13, and A14 as follows:

A1. One embodiment of the present disclosure includes a method for measuring mechanical properties of a microscale structure, comprising: receiving energy reflected from a structure while the structure is being illuminated; and determining at least one stress property and at least one temperature property of the structure from the energy received from the structure.

A2. One embodiment of the present disclosure includes a method for measuring mechanical properties of a microscale structure, comprising: receiving energy reflected from a structure while the structure is being illuminated; and determining at least one stress property of the structure from the energy received from the structure.

A3. One embodiment of the present disclosure includes a method for measuring mechanical properties of a microscale structure, comprising: receiving energy reflected from a structure while the structure is being illuminated; and determining at least one temperature property of the structure from the energy received from the structure.

A4. One embodiment of the present disclosure includes a method for measuring mechanical properties of a nanoscale structure, comprising: receiving energy reflected from a structure while the structure is being illuminated; and determining at least one stress property and at least one temperature property of the structure from the energy received from the structure.

A5. One embodiment of the present disclosure includes a method for measuring mechanical properties of a nanoscale structure, comprising: receiving energy reflected from a structure while the structure is being illuminated; and determining at least one stress property of the structure from the energy received from the structure.

A6. One embodiment of the present disclosure includes a method for measuring mechanical properties of a nanoscale structure, comprising: receiving energy reflected from a structure while the structure is being illuminated; and determining at least one temperature property of the structure from the energy received from the structure.

A7. Another embodiment of the present disclosure includes an apparatus for measurement of stress and temperature of a microscale structure, comprising: a receiver configured and adapted to receive energy from a microscale structure while the structure is being illuminated with laser energy; and a processor connected to said receiver, the processor configured and adapted to obtain information related to the received energy from the receiver, and determine at least one stress property and at least one temperature property of the structure from the information obtained from the receiver.

A8. Another embodiment of the present disclosure includes an apparatus for measurement of stress of a microscale structure, comprising: a receiver configured and adapted to receive energy from a microscale structure while the structure is being illuminated with laser energy; and a processor connected to said receiver, the processor configured and adapted to obtain information related to the received energy from the receiver, and determine at least one stress property of the structure from the information obtained from the receiver.

A9. Another embodiment of the present disclosure includes an apparatus for measurement of temperature of a microscale structure, comprising: a receiver configured and adapted to receive energy from a microscale structure while the structure is being illuminated with laser energy; and a processor connected to said receiver, the processor configured and adapted to obtain information related to the received energy from the receiver, and determine at least one temperature property of the structure from the information obtained from the receiver.

A10. Another embodiment of the present disclosure includes an apparatus for measurement of stress and temperature of a nanoscale structure, comprising: a receiver configured and adapted to receive energy from a nanoscale structure while the structure is being illuminated with laser energy; and a processor connected to said receiver, the processor configured and adapted to obtain information related to the received energy from the receiver, and determine at least one stress property and at least one temperature property of the structure from the information obtained from the receiver.

A11. Another embodiment of the present disclosure includes an apparatus for measurement of stress and temperature of a nanoscale structure, comprising: a receiver configured and adapted to receive energy from a nanoscale structure while the structure is being illuminated with laser energy; and a processor connected to said receiver, the processor configured and adapted to obtain information related to the received energy from the receiver, and determine at least one stress property of the structure from the information obtained from the receiver.

A12. Another embodiment of the present disclosure includes an apparatus for measurement of temperature of a nanoscale structure, comprising: a receiver configured and adapted to receive energy from a nanoscale structure while the structure is being illuminated with laser energy; and a processor connected to said receiver, the processor configured and adapted to obtain information related to the received energy from the receiver, and determine at least one temperature property of the structure from the information obtained from the receiver.

A13. Another embodiment of the present disclosure includes a method for measuring thermal conductivity of a microscale structure, comprising: receiving energy from a structure being illuminated with energy and to which a stress load is being applied; and determining the thermal conductivity of the structure from the energy received from the structure.

A14. Another embodiment of the present disclosure includes a method for measuring thermal conductivity of a nanoscale structure, comprising: receiving energy from a structure being illuminated with energy and to which a stress load is being applied; and determining the thermal conductivity of the structure from the energy received from the structure.

Yet other embodiments include the features described in any of the previous statements A1, A2, A3, A4, A5, A6, A7, A8, A9, A10, A11, A12, A13, or A14, as combined with
(i) one or more of the previous statements A1, A2, A3, A4, A5, A6, A7, A8, A9, A10, A11, A12, A13, or A14,
(ii) one or more of the following aspects, or
(iii) one or more of the previous statements A1, A2, A3, A4, A5, A6, A7, A8, A9, A10, A11, A12, A13, or A14 and one or more of the following aspects:

Illuminating the structure with a laser.

Wherein said determining at least one stress property and at least one temperature property of the structure occurs simultaneously from the energy received from the structure.

Wherein said determining includes analyzing the energy received from the structure by Raman spectroscopy.

Applying stress to the structure.

Measuring the Raman shift difference $\Delta\omega_m$.

Calculating stress components $\sigma ij$.

Wherein said determining includes determining the stress distribution below the surface of the structure.

Wherein said determining includes determining the thermal conductivity of the structure.

Wherein the receiver and the processor are configured and adapted to perform Raman spectroscopy on the energy received from the structure.

A stress inducing member configured and adapted to impart stress to the structure during said receiving energy.

A laser connected to the receiver, the laser configured and adapted to impart laser energy to the structure.

Wherein the processor determines at least one stress property and at least one temperature property of the structure from the same information obtained from the receiver.

Wherein said applying applies the stress load in a uniaxial direction along a load axis.

Wherein said illuminating and said receiving are performed on a surface, the surface defining a surface axis normal to the surface.

Wherein the surface axis is perpendicular to the load axis.

This summary is provided to introduce a selection of the concepts that are described in further detail in the detailed description and drawings contained herein. This summary is not intended to identify any primary or essential features of the claimed subject matter. Some or all of the described features may be present in the corresponding independent or dependent claims, but should not be construed to be a limitation unless expressly recited in a particular claim. Each embodiment described herein does not necessarily address every object described herein, and each embodiment does not necessarily include each feature described. Other forms, embodiments, objects, advantages, benefits, features, and aspects of the present disclosure will become apparent to one of skill in the art from the detailed description and drawings contained herein. Moreover, the various apparatuses and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

Some of the figures shown herein may include dimensions. Further, some of the figures shown herein may have been created from scaled drawings or from photographs that are scalable. It is understood that such dimensions, or the relative scaling within a figure, are by way of example, and not to be construed as limiting.

FIG. 1-1B shows a scanning electron microscope image of the silicon cantilever.

FIG. 1-2A graphical representation of a comparison of fitting curves using Gauss, Lorentz, and Voigt functions, respectively.

FIG. 1-2B is a graphical representation of a Gaussian fitting of the laser line and Raman peak.

FIG. 1-3 is a graphical representation of the determination of the laser spot size.

FIG. 1-4 shows the measuring of the laser power at different locations to determine the laser power absorbed by the sample.

FIG. 1-5 shows the effective threshold laser power to create detectable temperature increase on the sample surface.

FIG. 1-6A is a graphical representation of a load-displacement curve corresponding to rounding of the cantilever end indicated by almost zero load and significant displacement. A load of 10 mN maximum was applied in this process.

FIG. 1-6B is a graphical representation of a load displacement curve after the rounding of cantilever end has been performed. The zero load displacement shown in FIG. 6A disappears.

FIG. 1-7A shows the Raman shift as a function of compressive strain at room temperature, comparison with Raman shift from literature.

FIG. 1-7B shows the Raman shift as a function of temperature without mechanical strain, comparison with Raman shift value from literature.

FIG. 1-8A shows the Raman shift as a function of strain at different temperature.

FIG. 1-8B shows the Raman shift as a function of strain at different temperature, linearly fitted.

FIG. 1-8C shows the applied stress as a function of compressive strain.

FIG. 2-1A shows a diagram of a setup according to one embodiment of the present invention.

FIG. 2-1B shows a detailed diagram of the mechanical loading and heating to the cantilever.

FIG. 2-1C photograph showing a setup according to one embodiment of the present invention.

FIG. 2-2A is a graphical representation of the mechanical loading process, combined with deformation measurement and thermal drift evaluation showing the overall load unload curve.

FIG. 2-2B is a graphical representation of the mechanical loading process combined with deformation measurement and thermal drift evaluation showing the deformation as a function of time during steady state.

FIG. 2-2C is a graphical representation of the mechanical loading process, combined with deformation measurement and thermal drift evaluation showing the thermal drift evaluation.

FIG. 2-2D is a graphical representation of the mechanical loading process, combined with deformation measurement and thermal drift evaluation showing the mechanical loading curve before and after correction of thermal drift.

FIG. 2-3A is a graphical representation of the creep curve for silicone at room temperature.

FIG. 2-3B is a graphical representation of the creep curve for silicone at 50° C.

FIG. 2-3C is a graphical representation of the creep curve for silicone at 100° C.

FIG. 2-4A is a graphical representation of thermal drift as a function of applied load at different temperature.

FIG. 2-4B is a graphical representation of thermal drift as a function of temperature under different loads.

FIG. 2-5A is a graphical representation of the strain rate of the silicon cantilever as a function of applied stress at 25° C., 50° C. and 100° C.

FIG. 2-5B is a graphical representation of the comparison with literature values.

FIG. 2-6 A is a graphical representation of the strain rate of the silicon cantilever as a function of temperature.

FIG. 2-6B is a graphical representation of a comparison of data.

FIG. 2-7 is a graphical representation of the stress exponent at 25° C., 50° C. and 100° C.

FIG. 2-8A is a graphical representation of the effect of creep on Raman spectroscopy measurement.

FIG. 2-8B is a graphical representation of the comparison of near-surface stress and applied stress to the silicon cantilever.

FIG. 3-1A is a diagram of the combined mechanical loading and Raman spectroscopy setup showing the overview of the setup.

FIG. 3-1B is a diagram of the combined mechanical loading and Raman spectroscopy setup showing the detailed view of the setup.

FIG. 3-1C is a diagram of the combined mechanical loading and Raman spectroscopy setup showing the SEM image of a silicon cantilever sample.

FIG. 3-2A is a schematic showing the laser heating profile of the examined cantilever.

FIG. 3-2B shows the coordinate system used for obtaining analytical solution.

FIG. 3-3A is a graphical representation of the truncation of the infinite summation of $\bar{t}$ showing $t_n$ as a function of n, showing the domination of the first 15 items.

FIG. 3-3B is a graphical representation of the truncation of the infinite summation of $\bar{t}$ showing $\bar{t}$ as a function of n, showing the truncation at the 16th item is proper.

FIG. 3-4-1 is a graphical representation of the load-displacement curve as a function of peak applied load. The Raman spectroscopy measurement was performed when the load was held constant at the maximum.

FIG. 3-4-2A shows measurement of the laser power at different points on sample to determine the laser absorption ratio.

FIG. 3-4-2B shows temperature rise measurement as a function of absorbed laser power to predict threshold laser power.

FIG. 3-5A is a graphical representation of the Raman shift as a function of compressive strain at different temperatures with localized laser heating.

FIG. 3-5B is a graphical representation of a comparison of Raman shift with and without localized laser heating.

FIG. 3-6A is a graphical representation of the Raman shift difference between the cases of with laser heating and without laser heating.

FIG. 3-6B is a graphical representation of the corresponding temperature increase at different strain level and overall temperature.

FIG. 3-7A is a graphical representation of the thermal conductivity of microscale silicon as a function of compressive strain at different temperatures.

FIG. 3-7B is a graphical representation of thermal conductivity of microscale silicon as a function of temperature.

FIG. 3-8A is a graphical representation of phonon thermal conductivity of Si at nanoscale as a function of tensile strain.

FIG. 3-8B is a graphical representation of the corresponding electron thermal conductivity as a function of tensile strain.

DESCRIPTION OF THE ILLUSTRATED EMBODIMENTS

Figures 1, 1A:
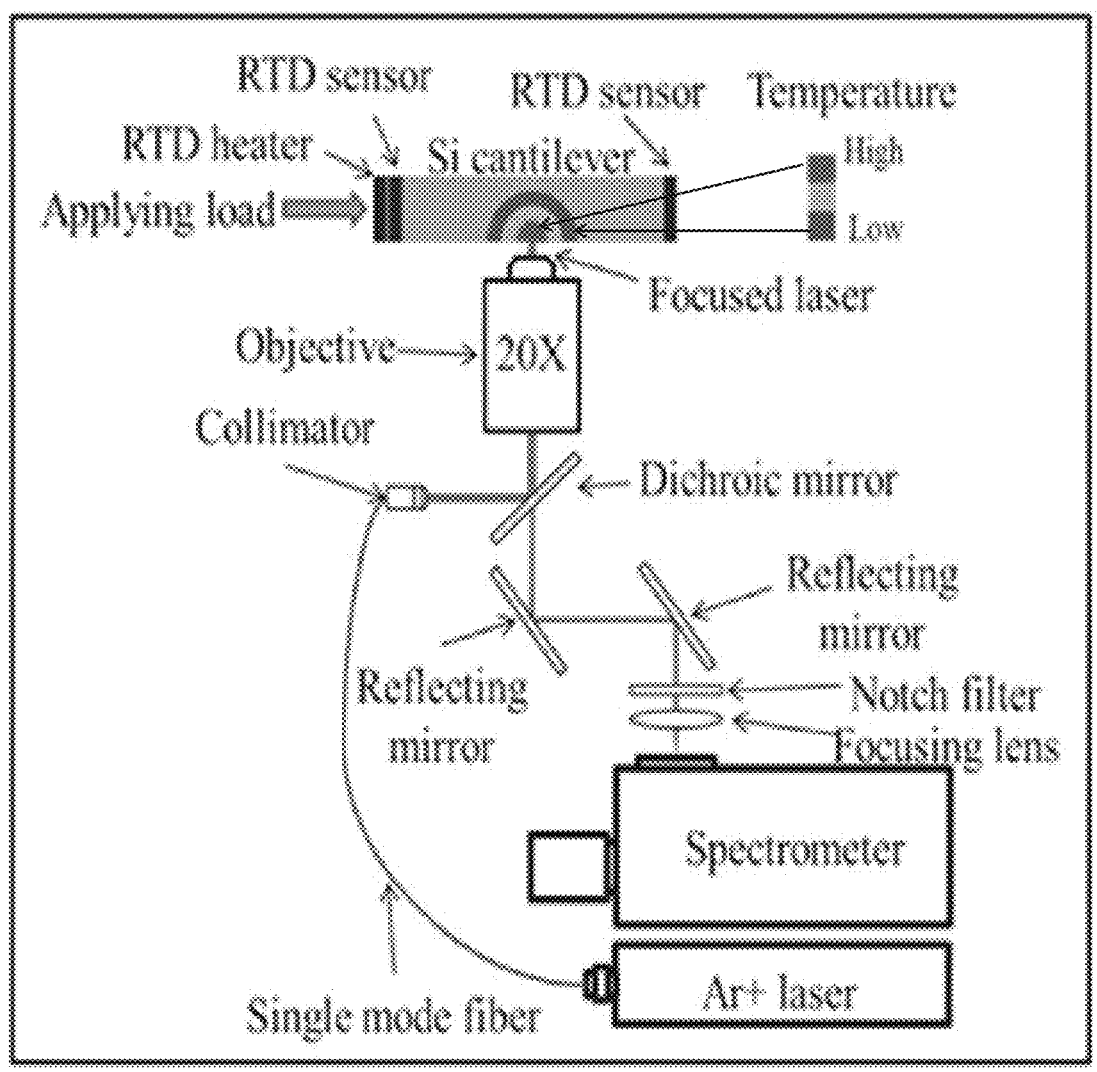
FIG. 1-1A is a schematic representation of a setup according to one embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention. It is understood that any reference to "the invention" is a reference to an embodiment of a family of inventions, with no single embodiment including an apparatus, process, or composition that should be included in all embodiments, unless otherwise stated. Further, although there may be discussion with regards to "advantages" provided by some embodiments of the present invention, it is understood that yet other embodiments may not include those same advantages, or may include yet different advantages. Any advantages described herein are not to be construed as limiting to any of the claims. The usage of words indicating preference, such as "preferably," refers to features and aspects that are present in at least one embodiment, but which are optional for some embodiments.

The use of an N-series prefix for an element number (NXX.XX) refers to an element that is the same as the non-prefixed element (XX.XX), except as shown and described. As an example, an element 1020.1 would be the same as element 20.1, except for those different features of element 1020.1 shown and described. Further, common elements and common features of related elements may be drawn in the same manner in different figures, and/or use the same symbology in different figures. As such, it is not necessary to describe the features of 1020.1 and 20.1 that are the same, since these common features are apparent to a person of ordinary skill in the related field of technology. Further, it is understood that the features 1020.1 and 20.1 may be backward compatible, such that a feature (NXX.XX) may include features compatible with other various embodiments (MXX.XX), as would be understood by those of ordinary skill in the art. This description convention also applies to the use of prime ('), double prime ("), and triple prime (''') suffixed element numbers. Therefore, it is not necessary to describe the features of 20.1, 20.1', 20.1", and 20.1''' that are the same, since these common features are apparent to persons of ordinary skill in the related field of technology.

Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples only, and further, unless otherwise explicitly noted, are approximate values, and should be considered as if the word "about" prefaced each quantity. Further, with discussion pertaining to a specific composition of matter, that description is by example only, and does not limit the applicability of other species of that composition, nor does it limit the applicability of other compositions unrelated to the cited composition.

What will be shown and described herein, along with various embodiments of the present invention, is discussion of one or more tests that were performed. It is understood that such examples are by way of example only, and are not to be construed as being limitations on any embodiment of the present invention. Further, it is understood that embodiments of the present invention are not necessarily limited to or described by the mathematical analysis presented herein.

Various references may be made to one or more processes, algorithms, operational methods, or logic, accompanied by a diagram showing such organized in a particular sequence. It is understood that the order of such a sequence is by example only, and is not intended to be limiting on any embodiment of the invention.

What will be shown and described herein are one or more functional relationships among variables. Specific nomenclature for the variables may be provided, although some relationships may include variables that will be recognized by persons of ordinary skill in the art for their meaning. For example, "t" could be representative of temperature or time, as would be readily apparent by their usage. However, it is further recognized that such functional relationships can be expressed in a variety of equivalents using standard techniques of mathematical analysis (for instance, the relationship F=ma is equivalent to the relationship F/a=m). Further, in those embodiments in which functional relationships are implemented in an algorithm or computer software, it is understood that an algorithm-implemented variable can correspond to a variable shown herein, with this correspondence including a scaling factor, control system gain, noise filter, or the like.

The stress-induced Raman shift and temperature-induced Raman shift of a silicon cantilever pertain to various embodiments of the present invention. During experimentation, the Raman shift was recorded as stress-only, temperature-only, and under combined influence of stress and temperature. From both theoretical analysis and experimental investigations it was discovered that the Raman signal induced by stress and temperature can be separated from a single shift measurement. Therefore, it is possible that both the stress and temperature inside the silicon microstructures can be studied using a single spectroscopic measurement. In silicon based devices, the temperature change and corresponding thermal stress development occurs simultaneously. This provides the foundation of thermal conductivity measurement of silicon micro-devices subject to mechanical stress and temperature increase simultaneously. The embodiments provided in the presented work advance such understanding for in situ measurements.

Various other embodiments of the present invention pertain to measurement of the creep behavior of silicon cantilever at the microscale and in the temperature range of 25° C. to 100° C. The stress level and the temperature range were chosen to correspond close to those in the semiconductor devices. The findings of this research are summarized as follows.

- the creep of the silicon cantilever increases as a function of the mechanical stress in the range of 50 MPa to 150 MPa.
- The creep rate of the silicon cantilever increases a function of temperature. But the increasing rate slows down with rise in temperature from 50° C. to 100° C.

Also the effect of creep on Raman spectroscopy measurement is small, given the exposure time of the Raman spectroscopy measurement is not too long. This provides the basis for stress measurement of microscale silicon structures using Raman spectroscopy. With different laser wavelength, the penetration depth to silicon also varies. Therefore, the Raman spectroscopy method has the capability of investigating the depth sensitive stress distribution of stress inside silicon. Measurements of surface stresses revealed that at lower temperature surface stress value is close to the bulk value. However, as a temperature increases, the surface stress values show deviation from the bulk values.

Various other embodiments pertain to measuring thermal conductivity of microscale Si cantilever specimens using Raman spectroscopy based measurements when it was being loaded in compression in a microscale displacement control setting. The embodiments involve application of compressive load along the microscale cantilever axis. While the load was being applied along axis, the stresses along the transverse side of the samples were calculated using Raman spectroscopy measurements. The thermal conductivity of silicon shows an increase as a function of compressive strain at all measurement temperatures. It also decreases when the overall temperature increases from room temperature to 100° C. The embodiments offered herein provide evidence of thermal mechanical coupling for microscale single crystal Si loaded uniaxially as a function of temperature. The overall thermal conductivity value is smaller than that for bulk silicon, which reveals the scale shrinkage effect on the phonon mean free path change. Although reducing the thermal conductivity has been succeeded with different methods to reduce the phonon mean free path, the method to increase the phonon mean free path is limited. Applying compressive stress to the micro-structures has been one of the few ways to increase the thermal conductivity. Combined with strain engineering for carrier mobility enhancement, the method of applying mechanical stress to increase the thermal conductivity may further increase the performance of micro-electronics.

Measurements are performed on microscale silicon cantilever samples. The silicon cantilever samples were subjected to mechanical load applied by a modified nanoscale loading platform able to apply load as a function of sample temperature. The temperature of the sample was measured using resistance temperature sensor (RTD). Raman spectroscopy was integrated to the nanoscale loading system with laser spot focused onto the sample surface. The mechanical stress and strain were measured using the nanoscale loading platform. The local surface stress and surface temperature were measured using the Raman spectroscopy system based on measured Raman shift and the analysis methodology explained in this section. In the following, a brief description of one sample and one setup is provided, it being understood that various other embodiments of the present invention contemplate yet other samples and yet other setups The schematic diagram of the setup is shown in FIG. 1-1A. As mechanical load applied to the silicon cantilever in the uniaxial direction, the Raman laser is focused onto the side surface of the sample using an objective. Back-scattered Raman signal is collected by the same objective and sent to a spectrometer.

Mechanical load is applied using the nanoindentation platform, manufactured by MicroMaterials Inc., UK. The load ranges from 0.1 mN to 500 mN, with the accuracy of better than 0.1 mN. The load application device in the form of a flathead attached to the nanoindentation load cell. Load calibration was performed before each experiment. For tests at temperatures higher than room temperature, two RTD sensors were attached to the end of the flathead, with one sensor acting as the heater, the other one acting as the temperature sensor.

Figures 1, 1B:
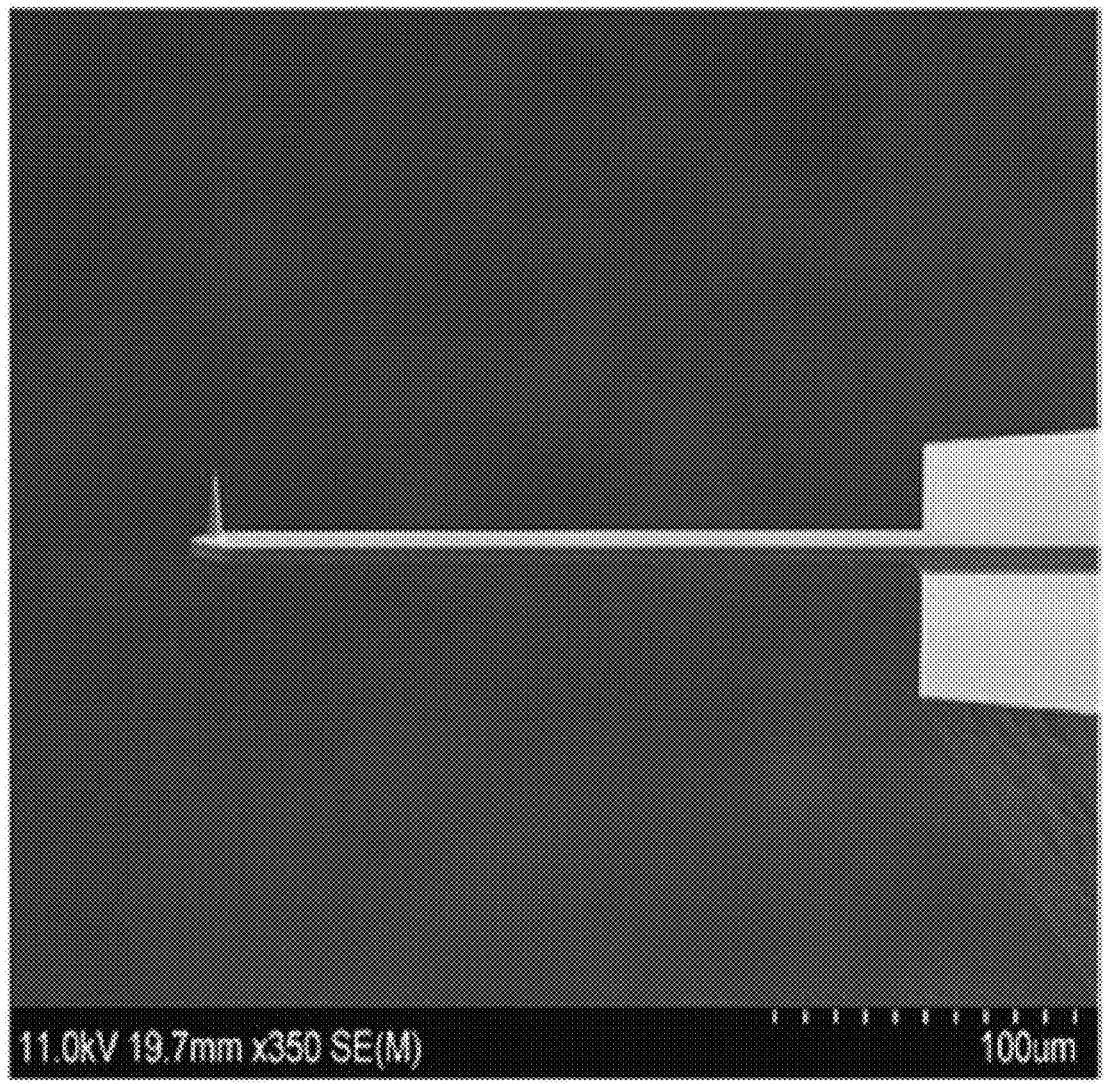

Atomic Force Microscope (AFM) cantilevers CT170 (Nanoscience Instruments, Inc., AZ) were used as the sample, as shown in FIG. 1-1B. It has a length of 225 μm, width of 40 μm, and thickness of 6.5 μm. It is made of highly doped single-crystalline silicon. As shown, the cantilever has a sharp tip. Before the load was applied, the cantilever tip was rounded and visibly inspected to make sure a good contact between the flat nanohead and sample is established. A preload of 1-2 mN is found to be good enough to remove the tip and round the end of the cantilever.

The Raman laser used is 514.5 nm Ar+ laser (Modu-Laser Inc, UT). The laser was directed to the sample using single mode fiber (SMF), and then focused using a 40× objective (NA=0.65). The back-scattered laser was collected by the same objective and sent to the spectrometer (Acton SP2500, Princeton Instruments Inc., NJ)

The measurement of stress using Raman spectroscopy is based on the principle of inelastic interactions between the incident laser and the vibration of crystal lattice. The lattice vibrations are quantized to different modes or phonons. In the case of silicon, the Raman modes include three degenerate k=0 optical phonon modes. In the case of unstressed single crystalline silicon at room temperature, these three modes have the same Raman frequency of ω0 at 520 Rcm-1, which is determined by the natural lattice vibrations of this material. The stress-induced Raman shift is described by the Raman secular equation, given as:

$$\begin{vmatrix} p\epsilon_{11}+q(\epsilon_{22}+\epsilon_{23})-\lambda & 2r\epsilon_{12} & 2r\epsilon_{13} \\ 2r\epsilon_{12} & p\epsilon_{22}+q(\epsilon_{33}+\epsilon_{11})-\lambda & 2r\epsilon_{23} \\ 2r\epsilon_{13} & 2r\epsilon_{23} & p\epsilon_{33}+q(\epsilon_{11}+\epsilon_{22})-\lambda \end{vmatrix} = 0. \quad (1\text{-}1)$$

Here p, q, and r are the optical phonon deformation potentials, with $p=-1.43\omega_0^2$, $q=-1.89\omega_0^2$, $r=-10.59\omega_0^2$, $\epsilon_{ij}$ are the strain tensor components; and λ are the eigenvalues which are related to the Raman shift frequencies. When stress is applied to silicon, the Raman frequencies are related to the eigenvalues λ as follows:

$$\lambda_m = \omega_m^2 - \omega_0^2 \text{ (cm}^{-2}\text{)}. \quad (1\text{-}2)$$

Here ωm (m=1, 2, 3) is the Raman frequency when stress is applied. The Raman shift change Δωm (m=1, 2, 3) is given as $$\Delta\omega_m = \omega_m - \omega_0 \approx \frac{\lambda_m}{2\omega_0}. \quad (1\text{-}3)$$

Since the strain tensor $\epsilon_{ij}$ and the stress tensor $\sigma_{ij}$ are symmetric, the Hooks law is expressed as, $$\{\epsilon\} = [S]\{\sigma\}, \quad (1\text{-}4)$$

where $\{\epsilon\}=\{\epsilon 11, \epsilon 22, \epsilon 33, 2\epsilon 12, \ldots\}^T$; $\{\sigma\}=\{\sigma 11, \sigma 22, \sigma 33, \sigma 12, \ldots\}^T$; S is the elastic compliance matrix. For a material with cubic crystal structure, there are three independent constants in the compliance matrix, which are expressed as, $$[S] = \begin{bmatrix} S_{11} & S_{12} & S_{12} & 0 & 0 & 0 \\ 0 & S_{11} & S_{12} & 0 & 0 & 0 \\ 0 & 0 & S_{11} & 0 & 0 & 0 \\ 0 & 0 & 0 & S_{44} & 0 & 0 \\ 0 & 0 & 0 & 0 & S_{44} & 0 \\ 0 & 0 & 0 & 0 & 0 & S_{44} \end{bmatrix} (Pa^{-1}). \quad (1\text{-}5)$$

In the case of silicon, $S_{11}=7.68\times10^{-12}$ Pa$^{-1}$, $S_{12}=-2.14\times10^{-12}$ Pa$^{-1}$, and $S_{44}=12.7\times10^{-12}$ Pa$^{-1}$. For the measurement of mechanical stress inside silicon, the Raman shift difference $\Delta w_m$ (m=1, 2, 3) is measured, and then it is related to the stress components σij (i,j=1, 2, 3) by Eqs. (1)-(5).

Temperature affects the Raman shift by the anharmonic terms in the vibrational potential energy. The resonant frequency $\Omega(\vec{0},j;\omega)$ determines the scattering line position. The first approximation to the resonant frequency is given as $$\Omega(\vec{0},j;\omega) = \omega_{\vec{0},j} + \Delta(\vec{0},j;\omega) \quad (1\text{-}6)$$

where $\Delta(\vec{0},j;\omega)$ is the real part of the proper self-energy. $\Delta(\vec{0},j;\omega)$ is called the frequency shift, which specifies the position of the laser line shift. It includes the contribution from the cubic, quark, and higher order terms in the anharmonic Hamiltonian $H_A$. In general, the full width at half maximum (FWHM) of the Raman spectrum contains the information of temperature effect. In silicon, the temperature change affects the position of the Raman peak as well. This leads to a relatively easier way to detect the temperature effect—by detecting the Raman shift as a function of temperature, instead of detecting the FWHM versus temperature. The relationship between Raman shift and temperature has been explored by experiments. The Raman shift $\Omega(T)$ as a function of temperature based on the above relations is given as, $$\Omega(T) = \omega_0 + \Delta(T) \quad (1\text{-}7)$$

$$\Delta(T) = C\left(1 + \frac{2}{e^x - 1}\right) + D\left(1 + \frac{3}{e^y - 1} + \frac{3}{(e^y - 1)^2}\right) \quad (1\text{-}8)$$

$$x = \frac{hc\omega_0}{2k_B T}, \quad (1\text{-}9)$$

$$y = \frac{hc\omega_0}{3k_B T}$$

Here $\omega_0=528$ cm$^{-1}$, h=6.626×10$^{-34}$ J s, c=299 792 458 m/s, C=−2.96 cm$^{-1}$, and D=−0.174 cm$^{-1}$. Here C and D are fitting constants, which should not depend on stress/strain in the material. This function fits well with experimental data obtained between 5 and 1400 K.

Low laser power was applied as not to create detectable localized temperature increase on the sample surface. This condition was also ensured by localized temperature measurement of sample surfaces using RTD sensors. The effect of change in temperature on Raman shift was investigated at different stress levels with the corresponding stress/strain level being constant. The temperature levels chosen for the experiments were 25° C., 50° C., 100° C., and 150° C. Compressive load was applied as to create strain levels of 0%, 0.05%, 0.1%, 0.15%, 0.2%, and 0.25%, respectively. The combination of the temperature and the strain level results 24 sets of measurement. For each set of measurement, 5-10 repeated tests were performed.

In order to measure the stress-induced Raman shift and temperature-induced Raman shift accurately, some preliminary experiments were used to determine the position of the Raman shift peak, the laser spot size on the sample surface, the absorbed laser power, and effective threshold laser power to create or not to create detectable temperature increase. Besides, as shown in FIG. 1-1B earlier, the end of the cantilever is not flat. For the purpose of control of the displacement and better thermal conduction between the cantilever and the indenter, the end of the cantilever was flattened by applying multiple trail loads before any measurement.

The Raman peaks that can be observed depend on the polarization of the laser and the orientation of the silicon crystal. The silicon cantilevers used in this research have the top surface [100] oriented, and the side surface [011] oriented. The uniaxial load was applied to the cantilever in the [011] direction. The laser was focused onto the surface and backscattered from the same surface. According to the Raman selection rule, the third polarized phonon would be observed, which corresponds to $\Delta\omega_3$ in Eq. (1-3). The numerical aperture of the objective is 0.65. The other two phonon modes may also have an effect on the measurement. However, due to the relatively low numerical aperture of the objective, this effect from other phonon modes is limited.

The CCD camera of the Raman spectroscopy system captures Raman spectrum using discretized pixels. More pixels of the CCD will result in more accurate measurement of the Raman peak. However, even with high resolution CCD cameras, this discretized capturing process still introduces measurement error of the Raman peak position. The accuracy of the Raman peak detection can be improved by fitting the Raman shift spectrum. For example, the Raman peaks of 528.684 nm and 528.657 nm correspond to Raman shift of 521.455 cm$^{-1}$ and 520.489 cm$^{-1}$, respectively, when the laser line is at 514.5 nm. If this is used for stress measurement in silicon, it leads to stress difference of more than 300 MPa.

Figures 1, 2, 2A:
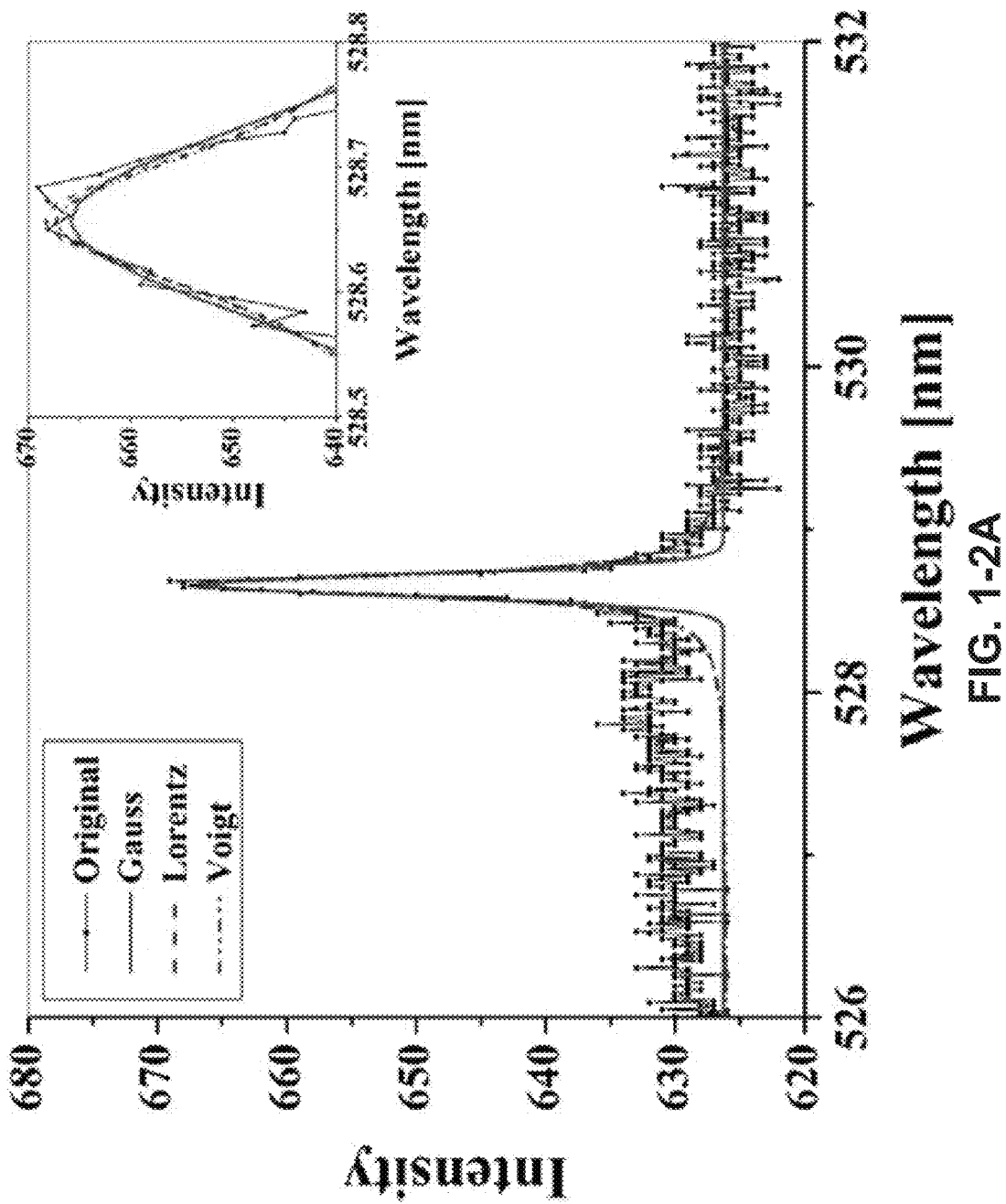
Figures 1, 2, 2B:
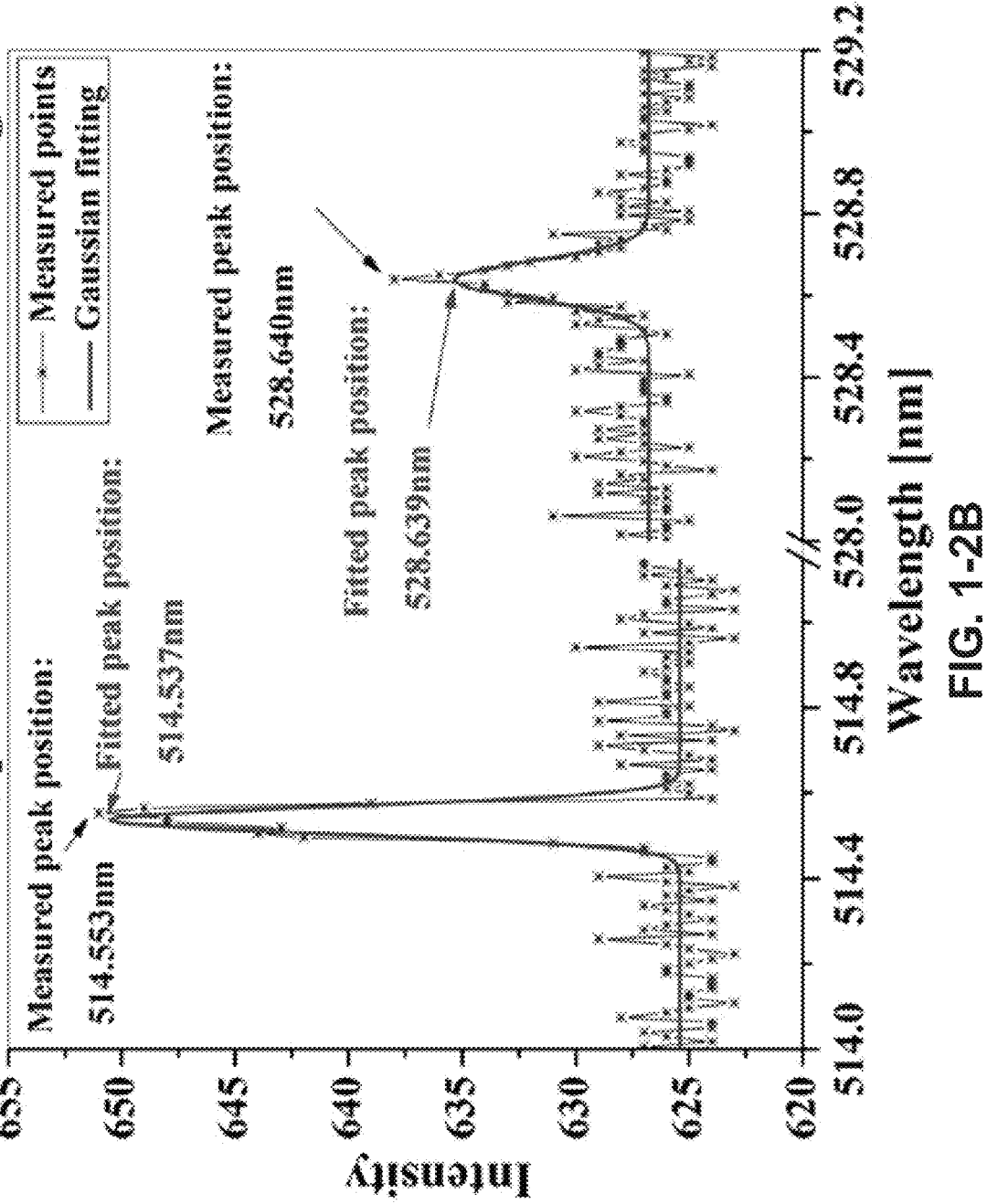

In Raman spectroscopy, the overall line shape originates from the sum of all the individual vibrations inside the material, and the exact vibrational frequency of a particular molecule is controlled by its environment. In solids, the excited molecule relaxes before incoherence becomes severe; while in gases, the dephasing is the dominant energy loss channel. In liquids, the situation lies in between. Voigt profile has been widely applied to fit Raman spectra in real practice. It is a convolution of Gaussian profile and Lorentz profile. Herein, the three fitting functions generate very close peak positions. One example has been shown in FIG. 1-2A, with corresponding peak positions listed in Table 1-1. In this table, the maximum value of the discretized spectrum obtained directly from the spectrometer is also listed for comparison purpose. As shown in Table 1-1, the three types of curve fitting functions provide close results, which differ from the maximum value from original measured data. However, the Gaussian fit has less fitting error than the Voigt fitting. In this research, for the purpose of simplicity, Gaussian fitting was applied in the curve fitting process. The peak position of the fitted Gaussian curve was treated as the real Raman shift peak. To further improve the Raman shift measurements, for each capture of the Raman shift signal, the laser line was also scanned. The same Gaussian fitting was also applied to the laser line, as shown in FIG. 1-2B.

Figures 1, 2, 3:
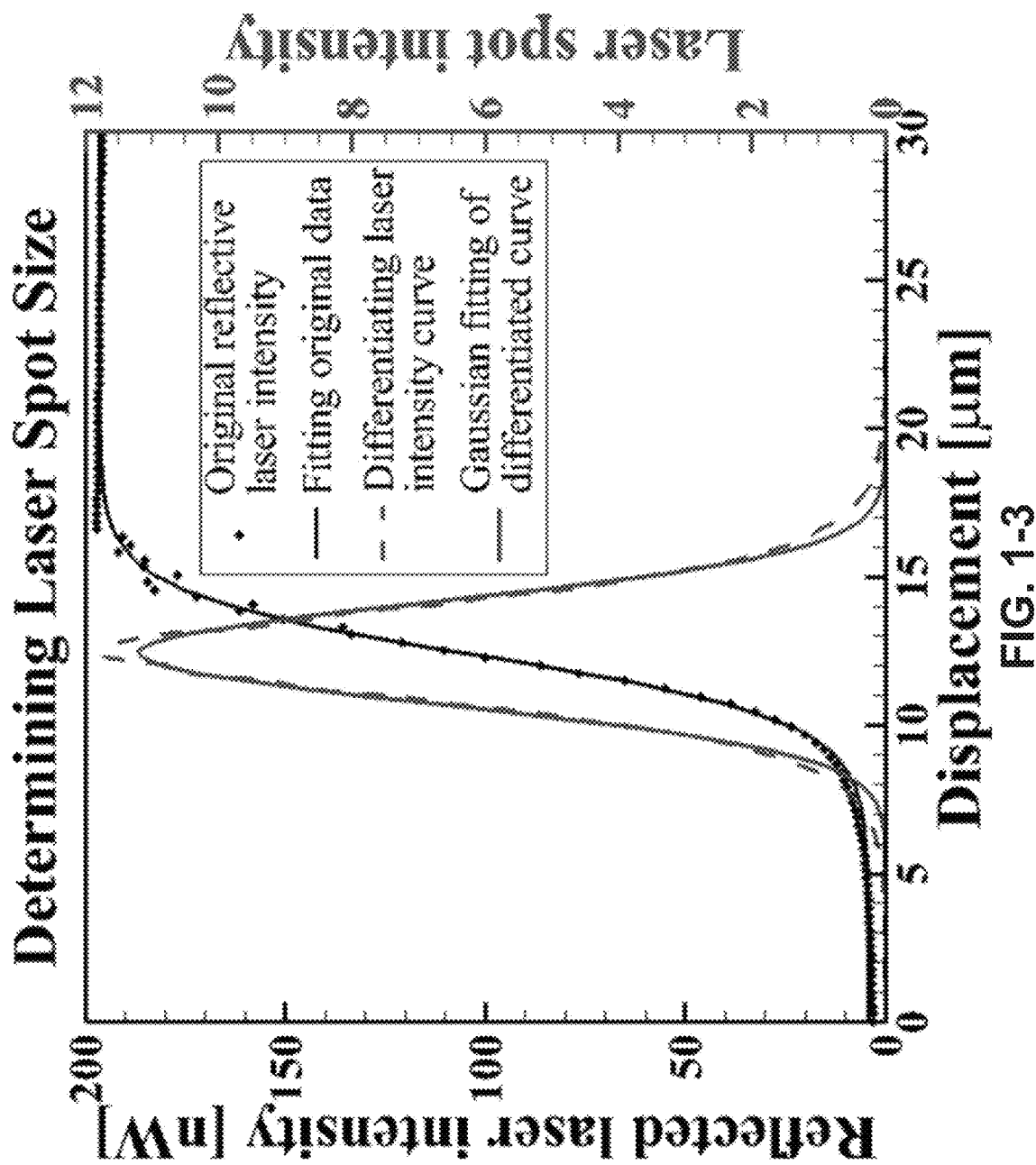

To achieve optimized Raman signal intensity and for precise control of the absorbed laser power, the laser spot size on the sample surface was determined. When light is well focused by a specific objective, the minimum spot size, d, is calculated by, $$d = \lambda/(\pi NA), \quad (1\text{-}10)$$

where $\lambda$ is the wavelength of the incident light; NA is the numerical aperture of the objective. However, in real practice, the laser spot size is affected by focusing distance and by the quality of incident laser beam. Therefore, the laser spot size should be determined for each measurement. One way to obtain the spot size is to scan across a cleaved edge. In the experiment, the laser was focused onto the sample for achieving maximum intensity of the Raman signal. Then the sample moved in lateral direction for the laser to scan across the edge. In this process, the reflected laser intensity was captured as a function of moving distance. The laser intensity profile was first fitted using proper functions for following process. Differentiation of the laser intensity profile with respect to moving distance x leads to the intensity file of the laser spot. The laser spot profile also follows Gaussian shape. It was fitted using Gaussian function $\exp(-2x^2/r_0^2)$ for calculating the laser spot radius $r_0$. The laser spot size as shown in FIG. 1-3 is 4.4045 µm. For most of the measurements, the laser spot size is in the range of 3.5-4.5 µm. If an objective with higher magnification is used, the laser spot size can be further reduced.

The absorbed laser power is parameter to derive properties of the sample. It is also helpful to control the localized temperature increase on the sample. In experiments, the incident laser was absorbed, reflected and scattered by the sample surface. Indirect method of evaluating absorbed laser power was applied herein, assuming the transmission ratio and reflectance ratio of the dichroic mirror and objective being constant within the laser intensity range used in the experiments. It is determined by measuring laser power at different points of the optical path as shown in the FIG. 1-4.

TABLE 1-1

Raman peak position from original data and curve fittings.

| | Max value of original data | Gauss | Lorentz | Voigt |
|---|---|---|---|---|
| Raman peak (nm) | 528.684 | 528.65725 | 528.65775 | 528.65649 |
| Fitting error (nm) | NA | 0.00205 | 0.00197 | 0.04965 |

When the output laser intensity from the Ar$^+$ laser machine is stable, the laser power at different locations shown in FIG. 1-4 was measured using a power meter (S140C+PM100USB, Thorlabs Inc., NJ). The total laser power $I_A$ coming out from the fiber end was mostly reflected by the dichroic mirror. A portion of $I_A$ transmitted through the dichroic mirror, noted as $I_C$. In the experiments, $I_C$ is the only "free end" of the optical path. The absorbed laser power is related to $I_C$ with a calibrated ratio. $I_E$ represents the laser power delivered to the sample. Since the sample surface is well-polished, the scattered portion of the laser is ignored in the experiments. Therefore, the absorbed laser power is the difference between $I_E$ and the reflected portion. The reflected laser power from the sample surface was derived from $I_D$ after taking account the transmission ratio of the objective and the dichroic mirror. Finally the absorbed laser power was represented as a function of $I_C$, after calibration of the transmission ratio and reflectance ratio of the dichroic mirror and the objective. The final relationship between the absorbed laser power FIG. 1-3. Determination of the laser power $I_{AB}$ and $I_C$ is represented as, $$\frac{I_{AB}}{I_C} = \frac{I_C \times I_E^2 - I_A \times I_B \times I_D}{I_C \times I_C \times I_E} = a. \quad (1\text{-}11)$$

In Eq. (1-11), the ratio is assigned to a constant a. After calibration at different laser power levels, the value of a is found to be 273±21. For each measurement, the absorbed laser power is calculated as, $$I_{AB} = a \times I_c \quad (1\text{-}12)$$

$I_C$ was measured to evaluate the absorbed laser power by the sample.

The Raman shift of silicon is affected by both temperature and mechanical stress of the sample. There will always be localized temperature increase and corresponding thermal stress when the laser is focused onto the sample. However, the capability of the spectrometer to detect this temperature increase or thermal stress/strain is limited by the focal length of the spectrometer, the gratings, and the number of pixels of the CCD array (if CCD is used as the photo detector). For a specific spectrometer, there can be a cut-off value of temperature increase or thermal stress, below which the change of temperature or stress is not easily detected by the spectrometer. In another meaning, there is an effective threshold laser power, below which the temperature increase created by the laser heating cannot be detected by the spectrometer. The temperature-effect-only Raman shift can be measured without applying mechanical load. However, when the stress-effect only Raman shift to be measured, the laser power can be chosen as not to create detectable temperature increase of the sample surface caused by laser heating. Therefore, there is an effective threshold laser power, above which detectable temperature increase of the sample surface will be created. The effective threshold laser power was calibrated by setting the sample to a constant temperature (room temperature in this case) and measuring the temperature of the sample surface with different incident laser power using Raman thermometry. The effective threshold laser power was determined when the temperature measured by Raman thermometry appeared just higher than sample temperature measured by a RTD sensor. In the measurement, the sample was kept at 27° C. The plot of measured temperature by Raman spectroscopy versus absorbed laser power is shown in FIG. 1-5. The data points were fitted linearly, with 95% confidence intervals expressed by dashed lines. The intersection of the fitted line and the actual temperature line denoted the effective threshold laser power. In this case, the effective threshold laser power is about 2.43 mW. The laser power can be kept lower than the effective threshold laser power, when measuring stress effect-only Raman shift. However, if the laser power is too low, the exposure time for each Raman spectrum increases (>5 min), which introduces the measurement error of background noise, and vibration of the platform, etc. Therefore, the laser power used in the experiment was kept slightly higher than the effective threshold laser power, but less than 4 mW.

As shown in FIG. 1-1 earlier, the end of the cantilever has a triangular shape, which has limited contact between the cantilever and the heater. It also affects the measurement of the indenter displacement. However, before measuring thermal conductivity for each sample set as a function of applied strain, a pre-load process aiming to round the cantilever end was performed, as shown in FIG. 1-6. In this process, a load of 10 mN was applied to the cantilever. This load is big enough to break the sharp end of the cantilever, but not the whole cantilever beam. The breakage of the cantilever end leaves a flat region in the loading curve (FIG. 1-6A). After this rounding process, the loading curve of the cantilever exhibits normal shape (FIG. 1-6B). Rounding process also removes AFM tip.

Before measuring the Raman shift as a function of both mechanical strain and temperature increase, the Raman shift affected by these two parameters separately should be measured, for comparison and validation purpose. The measurement of Raman shift as a function of The Raman shift induced only by temperature increase and Raman shift induced only by mechanical stress at room temperature is shown in FIG. 1-7. In the experiments, the displacement of the cantilever was monitored by the nanoindentation system. The strain level of the sample was calculated by the measured displacement and the original length of the cantilever. Therefore, in FIG. 1-7, the strains are not exactly at 0.05%, 0.1%, and 0.2%, etc.

FIG. 1-7 shows the Raman shift induced by mechanical strain or temperature increase, with comparison to literature values. In FIG. 1-7A, the comparison Raman shifts were calculated from a relationship of Raman shift and mechanical strain. FIG. 1-7A shows the trend of the Raman shift to compressive strain. FIG. 1-7B shows the temperature-induced Raman shift, compared with the experimental values from literature.

FIG. 1-8 shows the Raman shift as a function of strain at different temperatures. The temperature significantly affects the Raman shift, as shown in FIG. 1-8A. At a specific temperature, the Raman shift is almost linearly affected by mechanical strain. The relationship of Raman shift and compressive strain at each temperature was fitted using a linear function and plotted in FIG. 1-8B. The slope for each linear fitting is 2.58 cm$^{-1}$ for Raman shift at 25° C., 0.97 cm$^{-1}$ for Raman shift at 50° C., and 0.51 cm$^{-1}$ for Raman shift at 100° C. FIG. 1-8B reveals the linear relationship of Raman shift and mechanical strain at temperature, as well as the effect of softening at higher temperature.

FIG. 1-8C shows the applied stress as a function of strain. It shows that the stress applied to the sample was actually higher at high temperature, compared to room temperature, but the Raman shift shows a lighter dependence on strain at higher temperature, as shown in FIG. 1-8B. This further confirms the temperature softening of the material. Overall, FIG. 1-8 shows that the temperature increase does not interact with the effect of strain on Raman shift, except for overall softening of the material. This also means the Raman shift may be affected by temperature and mechanical strain independently, which establishes the basis of separation of strain-induced Raman shift and temperature-induced Raman shift.

Due to the principle of Raman spectroscopy, the accuracy of final measurement includes on the accuracy of wavelength measurement. The spectrometer was calibrated using Hg light source before each experiment. The laser line was also scanned after each set of measurement.

The notch filter was typically used and the exposure time was kept short (<2 s). The measured laser line was 514.52 nm, instead of 514.5 nm. This 0.02 nm difference leads to 0.76 cm$^{-1}$ difference in the corresponding wavenumber, which is twice the wavenumber resolution of the system.

The nanoindentation system used in the experiments has load-control mode and displacement-control mode. The displacement measured by the nanoindentation system contains the deformation of the cantilever, as well as the deformation of the indenter and the cantilever base. The scale of the indenter and the cantilever base can be magnitudes bigger than the cantilever. The deformation of the indenter and the cantilever base may be smaller than that of the cantilever. Another reason of using load-control mode is because of the creep effect. When the cantilever is loaded with a constant mechanical force, the deformation of the cantilever increases as a function of time due to the creep effect. Therefore, the strain of the cantilever also increases as a function of time. The deformation of the cantilever occurred during the creep is small compared to the overall deformation caused by the mechanical load. Moreover, the creep rate will reach a steady state after a few seconds, with a low creep rate. The Raman spectroscopy measurement was carried out during the steady state creep. On the other hand, if the cantilever is loaded using displacement-control mode, the mechanical load to maintain this fix displacement will decrease as a function of time due to the creep relaxation effect. Load-control mode was applied.

Another discussion about the load-control or displacement control of the mechanical loading is that the Raman effect is intrinsically related to the mechanical stress, but expressed as a function of strain. The Raman peak exhibits splitting and shift which are linear with respect to applied stress. The Raman shift can be described in terms of the changes of spring constant of the q≈0 optical phonons with strain. The objective used in this research has the NA value of 0.65. The nanoindentation platform was selected because it provides enough space for integrating the Raman spectroscopy setup.

For the Raman spectroscopy measurement in some embodiments, point-wise measurement was applied. First of all, the mechanical load was applied in the uniaxial direction. The modified nanoindentation platform applies the mechanical load in the horizontal direction. In the meanwhile, the cantilever was positioned with the length axis horizontal, which was verified using the laser beam before Raman spectroscopy measurement. Second, the flathead which applies the compressive load and the base of the cantilever are at the scale of 1 mm. Both of them are at least one magnitude bigger than the cantilever, which is 225 μm×40 μm×6.5 μm. The relatively big indenter and cantilever base help transduce the mechanical force evenly to the cantilever. Furthermore, the cantilever is only 6.5 μm thick. The overall setup was kept inside a closed chamber, which maintains its inside temperature at 25° C. with a proportional integral differential (PID) controlled thermal management system. For high temperature tests, the cantilever was heated at both ends. Two RTD sensors were placed the both ends of the cantilever to monitor the temperature. One was attached to the cantilever base, while the other one was attached to flathead. The tests were performed when the temperature stabilized.

Whenever the laser is focused onto the sample surface, it will create localized temperature increase and subsequent thermal stress/strain. If the thermal stress/strain is comparable to the applied stress/strain, it will significantly affect the accuracy of the measurements. Fortunately, when the laser power is lower than the effective threshold value, this temperature increase cannot be detected by the spectrometer. At 300 K, the thermal expansion coefficient for silicon is 2.6×10$^{-6}$° C.$^{-1}$. Therefore, for a typical 10° C. of localized temperature increase of the laser spot, the subsequent thermal expansion will be $2.6 \times 10^{-5}$, which is about two magnitudes lower than the applied strain level. The cantilever was suspended at one end and free at the other end. This suspended structure also releases the thermal stress/strain to some extent. The effect of thermal expansion caused by laser heating on the Raman stress measurement is limited.

Various other embodiments of the present invention pertain to measurement of the creep behavior of silicon cantilever at the microscale and in the temperature range of 25° C. to 100° C. The stress level and the temperature range were chosen to correspond close to those in the semiconductor devices. The findings of this research are summarized as follows.

The creep of the silicon cantilever increases as a function of the mechanical stress in the range of 50 MPa to 150 MPa.

The creep rate of the silicon cantilever increases a function of temperature. But the increasing rate slows down with rise in temperature from 50° C. to 100° C.

Also, the effect of creep on Raman spectroscopy measurement is small, given the exposure time of the Raman spectroscopy measurement is not too long. This provides the basis for stress measurement of microscale silicon structures using Raman spectroscopy. With different laser wavelength, the penetration depth to silicon also varies. Therefore, the Raman spectroscopy method has the capability of investigating the depth sensitive stress distribution of stress inside silicon. Measurements of surface stresses revealed that at lower temperature surface stress value is close to the bulk value. However, as a temperature increases, the surface stress values show deviation from the bulk values.

Microscale silicon structures are parts of MEMS devices, due to the excellent electrical and mechanical properties, as well as low manufacturing cost. Nowadays, nanoscale silicon structures, e.g. silicon nanowires, have been used in similar devices, such as field effect transistors (FETs), p-n diodes, and some complementary inverters. The micro/nano-scale silicon structures are commonly subject to mechanical stress when functioning, which may lead to creep deformation of the structures under certain conditions. When the working temperature increases, the creep deformation of the silicon structures could cause permanent failure.

Creep is non-recoverable plastic deformation occurring at low load regimes, constant stress, and small strain rates. Creep occurs in the form of transient deformation of a material leading to permanent plastic strain at applied stress values lower than the material yield stress. Creep of bulk materials starts with a decreasing strain rate in the primary (initial) stage followed by a steady state—the secondary stage creep. After that, in the tertiary stage, the strain rate increases again until the materials fails. Besides occurring at high temperatures in bulk materials, creep deformation can also occur at nanoscale contacts at moderate temperatures. Characterization of such nanoscale creep deformation is useful for applications related to operation of miniature devices, thermal stability of interfaces etc. The creep behavior of a material is expressed by, $$\dot{\varepsilon} = A\sigma^n \mathrm{Exp}\left(\frac{Q}{RT}\right) \quad (2\text{-}1)$$

where $\dot{\varepsilon}$ is the strain rate, A is a material coefficient, Q is the activation energy, R is the universal gas constant, and T is temperature in Kelvin. The stress exponent n is usually used as an indicator of the creep mechanism. It is believed that when the value of n is 1, creep is controlled by vacancy diffusion as deformation mechanism; when the n value is 2, the creep mechanism the controlled by grain boundary sliding; when n is 3, diffusion-controlled dislocation motion dominates as deformation mechanism; and when n is 5, it is dislocation climb-controlled creep mechanism. During microscale indentation creep tests on certain metals, alloys, and ceramics at room temperature, high stress exponent values up to hundreds have been observed. The mechanism behind such high stress exponent values has been attributed to volumetric densification and dislocation pile up.

For silicon, the brittle-to-ductile transition occurs at temperature between 520° C. and 600° C. Creep deformation of silicon is believed to be higher above this temperature range.

For most MEMS devices, the working temperature may not exceed 200° C. Creep of silicon structures could still happen at low temperature, especially at microscale or nanoscale. Various embodiments of the present invention pertain to microscale creep behavior of silicon cantilevers from room temperature to 100° C. The creep mechanism and the correlation between surface stress and creep is discussed.

The deformation of the microscale silicon cantilever samples under constant load was investigated at 25° C., 50° C., and 100° C., respectively. The load was applied by a modified mechanical loading platform, FIG. 2-1. The temperature was controlled by electronic heaters and monitored by resistance temperature sensors (RTD). An open-path Raman spectroscopy setup was integrated to the mechanical loading system to measure the near-surface stress of the sample.

The schematic diagram of the setup is shown in FIG. 2-1A. As mechanical load is applied to the silicon cantilever in the uniaxial direction, the Raman laser was focused onto the side surface of the sample using a 40× objective. Back-scattered Raman signal was collected by the same objective and sent to a spectrometer. The mechanical loading platform can apply load ranging from 0.1 mN to 500 mN, with accuracy of better than 0.1 mN. The uniaxial load is applied using a flathead attached to the load cell. For tests at high temperature, one electronic heater and one RTD sensor were attached to both ends of the sample, for controlling and monitoring the temperature, respectively. Atomic force microscope (AFM) cantilevers CT170 (Nanoscience Instruments, Inc., AZ) were used as the sample. It possesses the length of 225 µm, width of 40 µm, and thickness of 6.5 µm. It was made of highly-doped single-crystalline silicon. Before the measurement was performed, the cantilever was compressed using a trial load to ensure good contact between the load application module and the sample, which was represented by a linearly increasing loading curve. A trial load of 1~2 mN was found to be enough to provide good contact area.

The laser used in this Raman spectroscopy setup was 514.5 nm Ar+ laser (Modu-Laser Inc, UT). The laser was directed to the sample using single mode fiber (SMF), and then focused using a 40× objective (NA=0.65). The back-scattered laser was collected by the same objective and sent to the spectrometer. (Acton SP2500, Princeton Instruments Inc., NJ)

The deformation of the cantilever under constant load was measured during with a mechanical loading process, as shown in FIG. 2-2A. The mechanical loading process consists of three stages—applying the load with a designated rate, holding the mechanical load at the maximum for a designated period of time and unloading the sample with a designated rate. The deformation measurement for creep was performed at the second stage of mechanical loading process, when the applied load was at its maximum. During the load holding stage, the load was held constant, and the deformation of the sample was monitored as a function of time, as shown in FIG. 2-2B. At the unloading stage, when the load was reduced to the 10% of the maximum value, the load was held for 100 seconds to evaluate the thermal drift of the system. In the thermal drift evaluation process, the last 60 seconds of drift data were fitted linearly to calculate the thermal drift rate of the system, as shown in FIG. 2-2C.

The thermal drift rate is a characteristic parameter of the system, and was assumed to be constant during the whole process of measurement. The thermal drift effect was treated by removing the thermal drift displacement from the whole mechanical loading curve. The correction of the thermal drift effect was applied as shown in FIG. 2-2 (*d*). The thermal drift rate in FIG. 2-2 C is 0.0947 nm/s. However, it alters the mechanical loading curve, as shown in FIG. 2-2 (*d*). Creep is the plastic deformation of solids under certain stress level (less than yield stress) and temperature (lower than the melting temperature). The creep behavior of solids is usually described by Eq. (2-1). The strain rate $\dot{\epsilon}$, and the stress σ and are calculated using the relations, $$\dot{\varepsilon} = \frac{dh(t)}{dt}\frac{1}{h}, \quad (2\text{-}2)$$

and $$\sigma = F/A_s \quad (2\text{-}3)$$

where h(t) is the dimension of the sample along which the load is applied; F is the applied load and $A_s$ is the cross-section of the sample. The stress exponent n is calculated by taking logarithm to both sides of Eq. (2-1), which gives, $$\ln\dot{\varepsilon} = n\ln\sigma + \ln\left(A \cdot \text{Exp}\left(\frac{Q}{RT}\right)\right) = n\ln\sigma + C(T) \quad (2\text{-}4)$$

where C(T) is a constant at a specific temperature. If the $\dot{\epsilon}$-σ curve is plotted in the double-log coordinates, the stress exponent n will be the slope of the curve at the constant creep stage. As shown in Eq. (2-2), the derivation of the strain rate includes differentiation of the creep curve h(t). However, the creep data are scattered dots, as illustrated in FIG. 2-2B. In order to perform the differentiation, corresponding curve fitting was used to obtain a smooth function of the creep curve. One fitting function for h(t) is given as, $$h(t) = h_i + a(t+t_i)^b + kt, \quad (2\text{-}5)$$

where $h_i$, a, b, and k are fitting constants. A slightly modified form (Eq. (2-6)) was used herein:

$$h(t) = h_i + at^b + kt. \quad (2\text{-}6)$$

Using the h(t) curve, and Eq. (2-2) to Eq. (2-6), the creep strain rate and stress exponent can be calculated.

The Raman spectroscopy measurements to calculate surface stress were performed at the maximum load, when the load was held constant. The measurement of stress using Raman spectroscopy can be based on the principle of inelastic interactions between the incident laser and the vibration of crystal lattice. The lattice vibrations are quantized to different modes or phonons. In the case of silicon, the Raman modes consist of three degenerate k=0 optical phonon modes. For unstressed single-crystalline silicon at room temperature, these three modes have the same Raman frequency of $\omega_0$ at 520 Rcm$^{-1}$, which is determined by the natural lattice vibrations of this material. The stress-induced Raman shift is described by the Raman secular equation, given as, $$\begin{vmatrix} p\dot{o}_{11} + q(\dot{o}_{22} + \dot{o}_{33}) - \lambda & 2r\dot{o}_{12} & 2r\dot{o}_{13} \\ 2r\dot{o}_{12} & p\dot{o}_{22} + q(\dot{o}_{33} + \dot{o}_{11}) - \lambda & 2r\dot{o}_{23} \\ 2r\dot{o}_{13} & 2r\dot{o}_{23} & p\dot{o}_{33} + q(\dot{o}_{11} + \dot{o}_{22}) - \lambda \end{vmatrix} = 0. \quad (2\text{-}7)$$

Here p q and r are the optical phonon deformation potentials, with $p=-1.43\omega_0^2$, $q=-1.89\omega_0^2$, $r=-0.59\omega_0^2$; $\dot{o}_{ij}$ are the strain tensor components; and λ are the eigenvalues which are related to the Raman shift frequencies. When stress is applied to silicon, the Raman frequencies are related to the eigenvalues λ as follows, $$\lambda_m = \omega_m^2 - \omega_0^2 \text{ [cm}^{-2}\text{]}. \quad (2\text{-}8)$$

Here $\omega_m$ (m=1, 2, 3) is the Raman frequency when stress is applied. The Raman shift change $\Delta\omega_m$ (m=1, 2, 3) is given as, $$\Delta\omega_m = \omega_m - \omega_0 \approx \frac{\lambda_m}{2\omega_0}. \quad (2\text{-}9)$$

Since the strain tensor $\dot{o}_{ij}$ and the stress tensor $\sigma_{ij}$ are symmetric, the Hook's law is expressed as, $$\{\dot{o}\} = [S]\{\sigma\}, \quad (2\text{-}10)$$

where $\{\dot{o}\} = \{\dot{o}_{11}, \dot{o}_{22}, \dot{o}_{33}, 2\dot{o}_{12}, \ldots\}^T$; $\{\sigma\} = \{\sigma_{11}, \sigma_{22}, \sigma_{33}, \sigma_{12}, \ldots\}^T$; S is the elastic compliance matrix. For a material with cubic crystal structure, there are three independent constants in the compliance matrix, which are expressed as, $$[S] = \begin{bmatrix} S_{11} & S_{12} & S_{12} & 0 & 0 & 0 \\ 0 & S_{11} & S_{12} & 0 & 0 & 0 \\ 0 & 0 & S_{11} & 0 & 0 & 0 \\ 0 & 0 & 0 & S_{44} & 0 & 0 \\ 0 & 0 & 0 & 0 & S_{44} & 0 \\ 0 & 0 & 0 & 0 & 0 & S_{44} \end{bmatrix} (\text{Pa}^{-1}). \quad (2\text{-}11)$$

In the case of silicon, $S_{11}=7.68\times10^{-2}$ Pa$^{-12}$, $S_{12}=-2.14\times10^{-12}$ Pa$^{-1}$, and $S_{44}=12.7\times10^{-12}$ Pa$^{-1}$. For the measurement of mechanical stress inside silicon, the Raman shift difference $\Delta\omega_m$ (m=1, 2, 3) is measured, and then it is related to the stress components $\sigma_{ij}$ (i,j=1, 2, 3) by Eq. (2-7) to Eq. (2-11). The deformation of the silicon cantilever under constant load was investigated at 25° C., 50° C., and 100° C., respectively. The compressive load at the holding stage was chosen to be 13 mN, 26 mN and 39 mN. The corresponding compressive stress along the longitudinal direction of the cantilever was 50 MPa, 100 MPa, and 150 MPa. The mechanical loading and unloading rate were chosen to make the loading and unloading stages last for 10 s, respectively. The load was held at its maximum for 500 s to investigation the deformation at constant load. The creep curve includes of three stages. The time frame of the second stage is much longer than that of the other two stages. The third stage of the creep curve may not be of interest. For the silicon cantilever investigated in this research, the initial stage of the creep is very short (<2 s) in the observation time frame of 500 s. Therefore, the second stage of creep dominates the creep curve, which makes the creep curve follow a linear pattern, as shown in FIG. 2-3. The term kt in Eq. (2-6) dominates the terms on the right side of the equation. At room temperature, the overall deformation from creep is limited (<30 nm), as shown in FIG. 2-3A. As the temperature increases to 50° C., the overall deformation increases dramatically by a factor of 5 to 6, as shown in FIG. 2-3B. From 50° C. to 100° C., the deformation of the cantilever under compression further increases, but the ratio of this increase of much lower than that from room temperature to 50° C. The deformation of the cantilever tends to increase as a function of the compressive load.

Figures 1, 2, 3, 4:
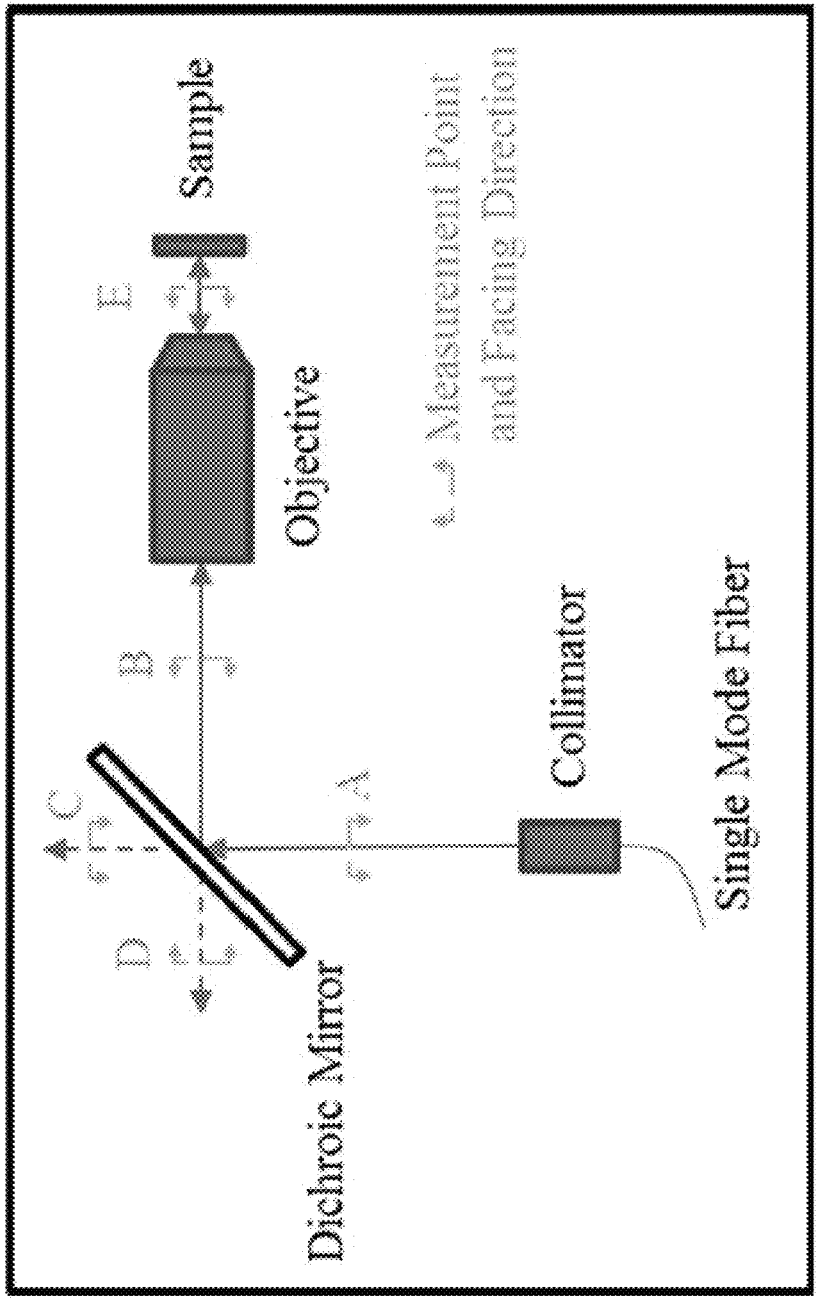

The setup was maintained at a constant temperature before and during the measurements for thermal equilibrium of the system. The whole equipment was placed inside a closed chamber to eliminate the air flow and other possible disturbance to the temperature distribution of the system. As shown in FIG. 2-4, temperature determines the magnitude of the thermal drift rate. The thermal drift rate increases when the temperature increases. Besides, at higher temperature, the variation of the thermal drift rate also increases, which means a higher fluctuation of the temperature distribution of the system. This phenomenon is common for high temperature tests. The temperature fluctuation of the system can be suppressed by minimizing the air flow inside the test chamber and also longer waiting time for the system to reach thermal equilibrium. FIG. 2-4B shows the dependence of the thermal drift rate on the maximum load. It reveals that the thermal drift rate has low dependence on the maximum load at this loading range. After compensation of the thermal drift in the process described by FIG. 2-4, the realistic creep rate of the silicon cantilever was obtained.

At room temperature, the strain rate of the cantilever under uniaxial compressive load is in the order of $2 \times 10^{-7}$ s$^{-1}$, with slight increase as a function of maximum load, as shown in FIG. 2-5A. During the loading time of 500 s, the overall deformation during the mechanical holding period corresponds to compressive strain of 0.01%. FIG. 2-5A also shows that the strain rate increases dramatically as a function of temperature. From 25° C. to 100° C., the strain rate increases by a factor of 10. Besides the dependence of the strain rate on temperature, the strain rate is also affected by the applied stress. Almost temperature, the strain rate increases as a function of applied stress. The increase ratio of the strain rate from 50 MPa to 150 MPa is less than 2. From FIG. 2-5A, it can be deduced that the strain rate of the silicon cantilever is affected by the temperature increase in the temperature range of 25° C. to 100° C., and in the stress range of 50 MPa to 150 MPa.

The comparison of the parameters of the sample and the testing conditions are listed in Table 2-1. For silicon, the transition from brittle to ductile behavior happens in the temperature range of 520° C.~600° C. Therefore, the creep deformation of bulk silicon is unlikely to happen below 600° C. However, for microscale silicon samples, the creep deformation occurs at relatively lower homologous temperature due to the size effect and surface stress.

The steady state creep of silicon can be expressed by the kinetic equation $$\dot{\varepsilon} = 10^{11} s^{-1} \text{Exp}\left(-\frac{5.6 \text{ eV} - 2.7 \times 10^{-21} \text{cm}^3 \sigma}{kT}\right), \quad (1)$$

where σ is the applied stress; k is the Boltzmann constant; and T is the absolute temperature. The equation is valid for stress level up to 100 MPa. According to this equation, the strain rate of bulk silicon has strong dependence on temperature and applied stress, as shown in FIG. 2-5B.

TABLE 2-1

Comparison of the parameters of the sample and test conditions with literatures

| Material | Characteristic scale | Stress range [MPa] | Temperature range [° C.] | Measurement condition |
|---|---|---|---|---|
| SCS*, heavily doped | 225 μm × 40 μm × 6.5 μm | 50~200 | 25~150 | In-situ uniaxial compression |
| SCS | Bulk | 2~7 | 800~940 | |
| SCS, N-type | Bulk | 20~147 | 900~1300 | In-situ uniaxial compression, argon atmosphere |
| SCS, two different dislocation densities | 12 mm × 4.4 mm × 3.5 mm | 1.4~8.3 | 850~1300 | uniaxial compression, argon atmosphere |
| SCS | Bulk | 50~200 | 600~850 | 4-point bending |
| SCS | 45 μm in thickness | ~40 | 1000, 1100 | Ex-situ deformation |

*SCS: single-crystalline silicon

In FIG. 2-6, the strain rate is plotted as a function of temperature. The strain rate increases by a factor of 10 with 75 degrees of temperature increase (25° C. to 100° C.). This is for the condition of low homologous temperature (0.18~0.22) and microscale silicon sample. In contrast, at higher homologous temperature (>0.5), the transition from brittle to ductile behavior occurs. The dependence of creep rate on temperature increase is therefore much higher, FIG. 2-6B. However, it should be remembered that the available data from other literature works is for high homologous temperature and bulk scale silicon samples.

Stress exponent n in Eq. (2-1) has been used as an indicator of the creep mechanism of materials, especially metals. Similar analysis has been performed here and shown in FIG. 2-7A. The stress exponent roughly exhibits an increase as a function of temperature. The slight decrease of the stress exponent from 25° C. to 50° C. is due to the measurement point of 150 MPa at 50° C. Overall, the stress exponent obtained in this research is relatively low (<1), which indicates that the creep behavior of this silicon cantilever at low homologous temperature cannot be explained by existing creep models.

The creep mechanism of silicon has also been analyzed earlier according to the Ashby map. The Ashby map is based on experimental investigation of creep properties of silicon with the grain size of 100 μm. If analyzed using the Ashby map, the homologous temperature range and the applied stress investigated in this research is categorized into the power-law creep. However, in the Ashby map, this region is not directly supported by experimental results.

In order to further investigate the fundamental relationship between the stress and strain rate, the surface stress of the silicon cantilever was measured using Raman spectroscopy with the spatial resolution of around 4 μm. The detail of the stress measurement is discussed herein.

The creep measurement of the silicon cantilever benefits from accurate measurement of the displacement at micrometer or even nanometer scale. While compressive load is applied to the cantilever, it also compresses the sample holder. The overall displacement measured by the system may include the creep of the cantilever and the creep of the sample holder. For the cantilever used in this research, the cross section is $2.6\times10^{-10}$ m$^2$, while the cross section of the cantilever base is larger than $7\times10^{-7}$ m$^2$. The cross section of the sample holder is much bigger, which is in the order of $5\times10^{-5}$ m$^2$. With the sample compressive load applied to the cantilever, the cantilever base and the sample holder, the deformation of the cantilever can dominate the overall deformation of the whole assembly, despite the material property of each part.

Another factor that could influence the accuracy of the creep measurement is the thermal expansion of different parts, especially for high temperature measurements. The experimental setup was kept inside an enclosed chamber, where the inside temperature was kept constant with a temperature difference of about 3° C. above the outside temperature. The silicon cantilever and the end of the load application module were heated locally with electronic heaters. Thermal equilibrium was ensured by a constant reading from the RTD sensors attached to the sample and the load application module. This localized heating avoids disturbance to the functioning electrical parts of the test platform. However, it also creates a constant temperature gradient between the sample and other parts of the equipment. This temperature gradient may lead to extra thermal drift to the parts close to the sample. However, compared to global heating of the whole assembly, the localized heating method should introduce much less error to the measurement, because the global heating method will not only increase the thermal drift, but also affect the functioning of the electric sensors of the system. Raman spectroscopy has been an effective tool to investigate the mechanical stress and strain of silicon at microscale. The measurement of stress using Raman spectroscopy is based on the principle of inelastic interactions between the incident laser and the vibration of crystal lattice, which is expressed by the Raman secular equation, $$\begin{vmatrix} p\varepsilon_{11}+q(\varepsilon_{22}+\varepsilon_{33})-\lambda & 2r\varepsilon_{12} & 2r\varepsilon_{13} \\ 2r\varepsilon_{12} & p\varepsilon_{22}+q(\varepsilon_{33}+\varepsilon_{11})-\lambda & 2r\varepsilon_{23} \\ 2r\varepsilon_{13} & 2r\varepsilon_{23} & p\varepsilon_{33}+q(\varepsilon_{11}+\varepsilon_{22})-\lambda \end{vmatrix} = 0. \quad (2\text{-}13)$$

Here p, q and r are the optical phonon deformation potentials, with $p=-1.43\omega_0^2$, $q=-1.89\omega_0^2$, $r=-0.59\omega_0^2$; $\delta_{ij}$ are the strain tensor components; and $\lambda$ are the eigenvalues which are related to the Raman shift frequencies.

The Raman secular equation relates the Raman shift to the strain of the silicon sample. The elastic matrix correlates the strain to the mechanical stress. Both relationships are one-to-one mapping. When the stress is constant, the strain is changing as a function of time, due to the creep effect; and when the strain is constant, the stress is changing as a function of time as well, due the relaxation effect. This phenomenon conflicts with the idea of stress or strain measurement using Raman spectroscopy. That means either the stress or the strain cannot be measured accurately from the Raman spectroscopy method. The Raman shift from a single time interval of 200 s is shown in FIG. 2-8A. In this figure, the Raman shift values were linearly fitted as a function of time. The slope of the fitted line is $1.28\times10^{-6}$ nm/s, which means the Raman shift is not affected by the measurement time. Considering the strain rate of the silicon cantilever is only $2.5\times10^{-7}$ s$^{-1}$, for the time interval of 200 s, the strain change is $5\times10^{-5}$, or 0.005%, which is at least one magnitude lower than the strain level in the Raman spectroscopy measurement of this research. Therefore, in the temperature range of 25° C. to 100° C., and the stress level of tens to hundreds of MPa, the effect of creep on the Raman spectroscopy measurement is limited during the exposure time of 200 s.

For microscale or nanoscale structures, the atoms near the surfaces experience less bounding forces from neighboring atoms, compared with the inside atoms. This fact also applies to bulk materials. But at the bulk scale the effect is insignificant because of its atomic or nanometer range of scale. The lack of bounding force results in a "relaxed" state of the surface or near-surface atoms. Therefore, the stress at surface is zero and near the surface is lower than the bulk stress value. Besides, the stress also exhibits a depth dependency as the bounding force increases when the depth with regard to the surface increases. Theoretically, the stress at free surfaces should be zero.

FIG. 2-8B shows the correlation between the surface stress and applied stress for the cantilever in this research. At room temperature, the surface stress roughly matches with the applied stress. At some points, the surface stress is slightly higher than the applied stress. When the temperature increases, the surface stress becomes lower than the applied stress, and it keep decreasing as temperature changes from 25° C. to 100° C. This implies that the relaxation of the surface atoms increases as a function of temperature. In the meanwhile, the creep rate of materials also increases as a function of temperature increase. The mechanism of creep includes vacancy diffusion, grain boundary sliding, diffusion-controlled dislocation, and dislocation climb. At micro/nano-scale, the material properties near the surface show significant size dependence. The relaxation of surface atoms will enhance the creep strain rate of the material. Across a given microscale cross section, surface atoms are likely to experience higher strain than the bulk atoms due surface softening. This also explains that silicon can sustain more mechanical strain at microscale than bulk scale. However, this does not mean the temperature dependency of the creep effect is entirely caused by the near-surface relaxation. In some embodiment of the present invention, the near-surface relaxation is contributing to the temperature dependency of the creep effect.

Various embodiments presented herein provide integrated Raman thermometry in a microscale mechanical loading setup. Thermal conductivity measurement of microscale Si cantilevers is performed while those are being loaded in compressive manner along their axes. Analyses and results focus on presenting a quantification of the extent of thermomechanical coupling in microscale Si. However, methods and results have wide applicability in problems where thermal conduction influences mechanical performance.

Analyses shown herein in various embodiments pertain to measuring thermal conductivity of microscale Si cantilever specimens using Raman spectroscopy based measurements when it is being loaded in compression in a microscale mechanical loading setting. Compressive load is applied along the microscale cantilever axis. While the load is being applied along axis, the stresses along the transverse side of the samples were calculated using Raman spectroscopy measurements. The experiments were carried out using an integrated nanomechanical loading-Raman spectroscopy platform, as shown in FIGS. 3-1A and 3-1B. The mechanical load was applied in the uniaxial direction. The Raman spectroscopy apparatus approached the sample from the lateral direction. The back-scattered laser from the sample surface was collected by the objective and analyzed by the spectrometer. The load that can be applied ranges from 0.1 mN to 500 mN, with an accuracy better than 0.1 mN. For high temperature tests, one resistance temperature detector (RTD) was attached as a heater on one end of sample. The other end of the sample was heated by electrical coils. One RTD sensor was attached to each end of the sample serving as temperature detector. The RTD sensors have tolerance of ±0.12%, and repeatability of ±0.1° C.

Figures 1A, 2:
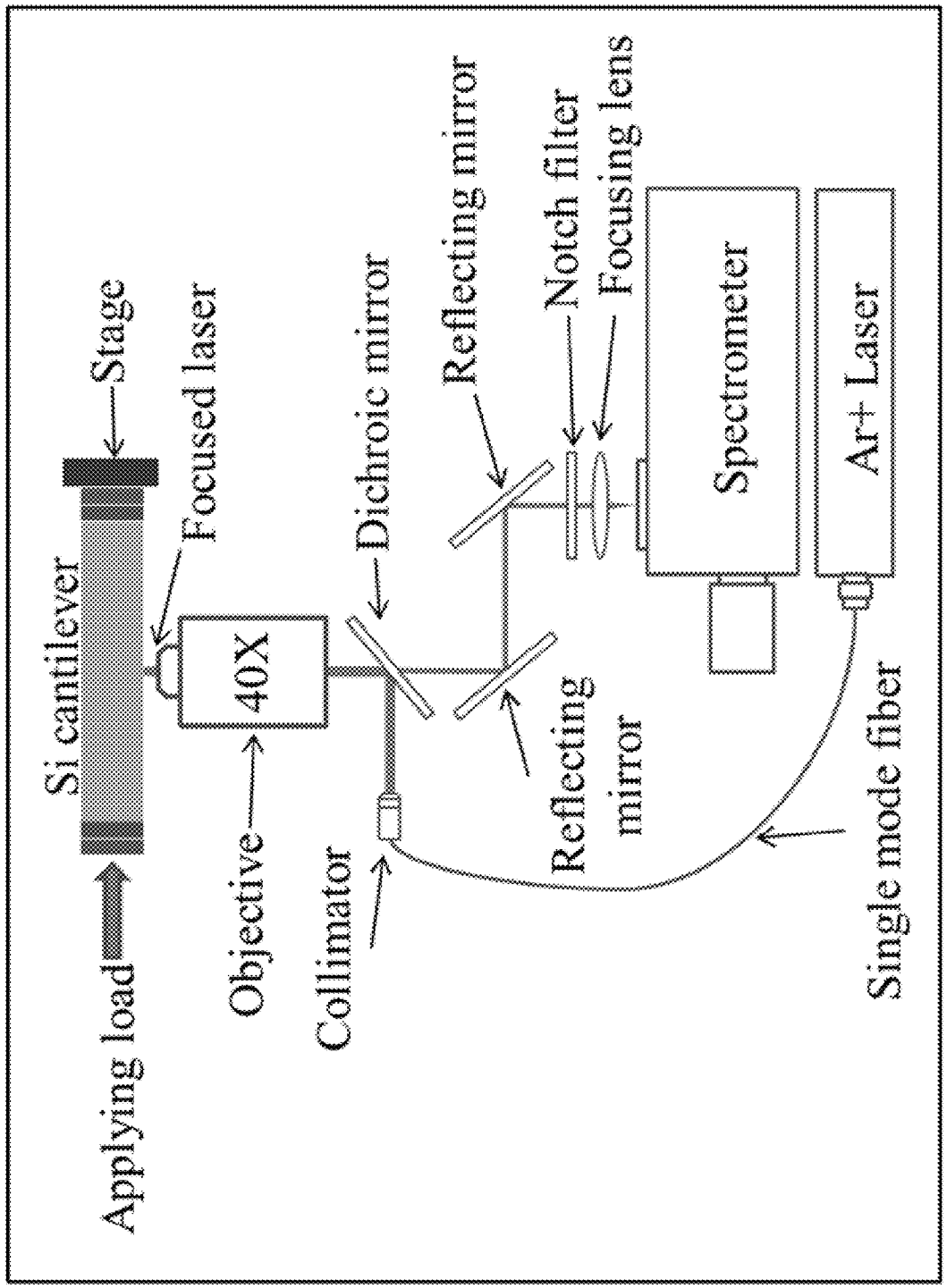
Figures 1B, 2:
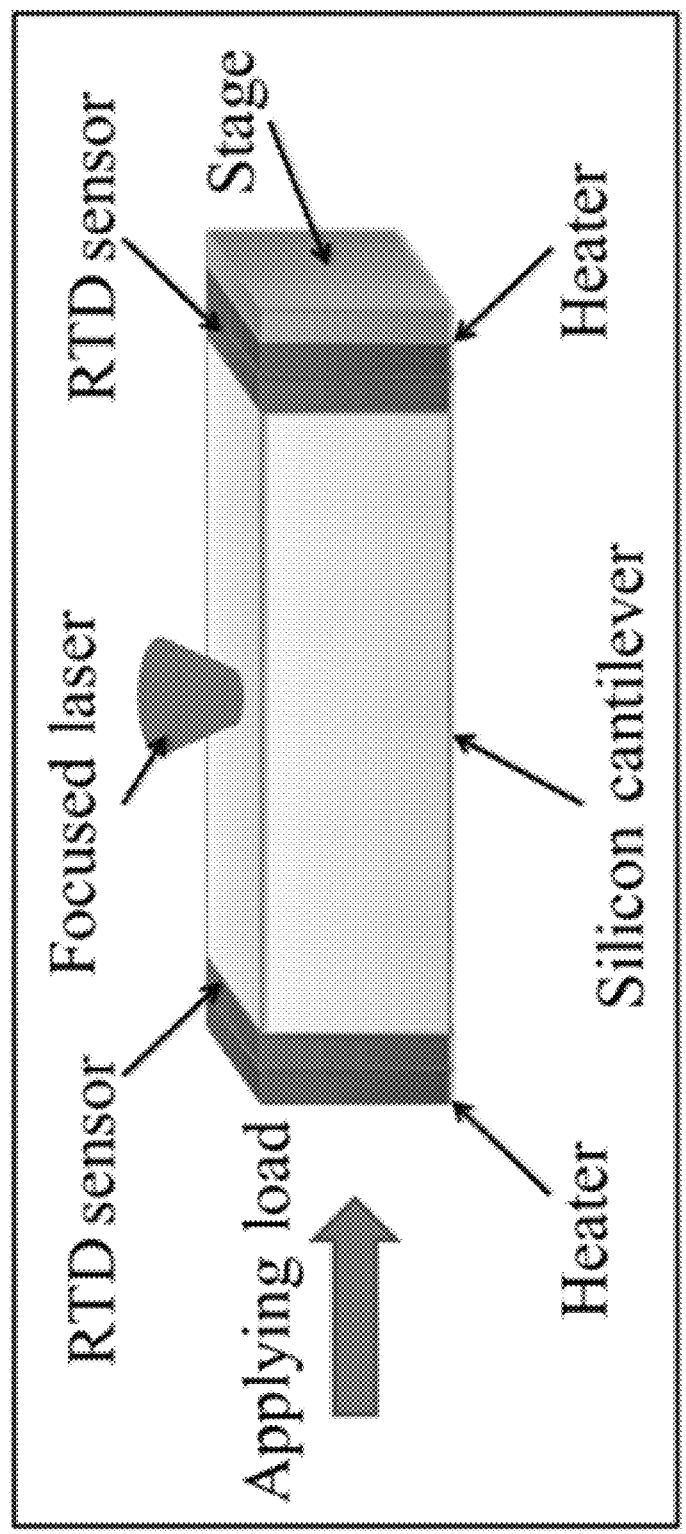
Figures 1C, 2:
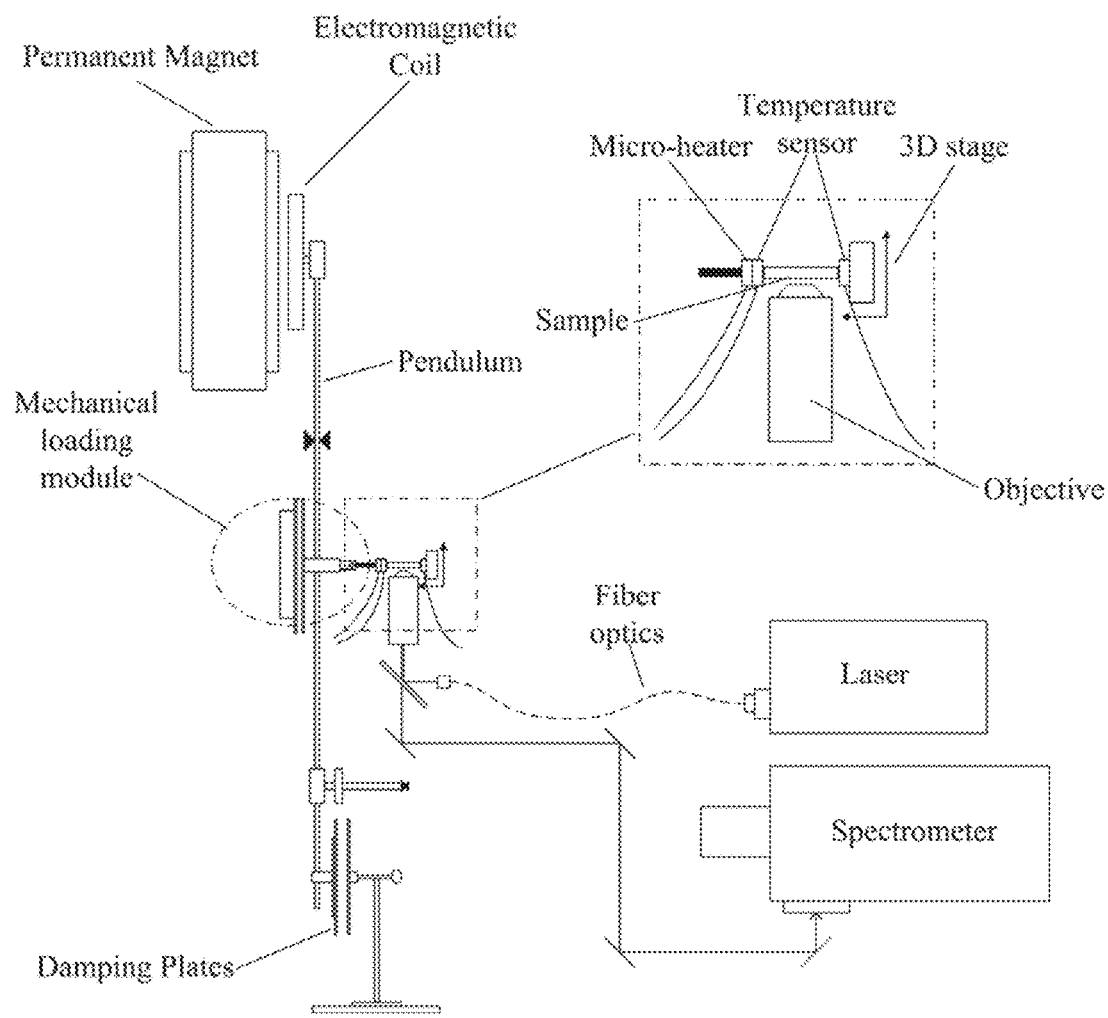
Figures 2, 2A:
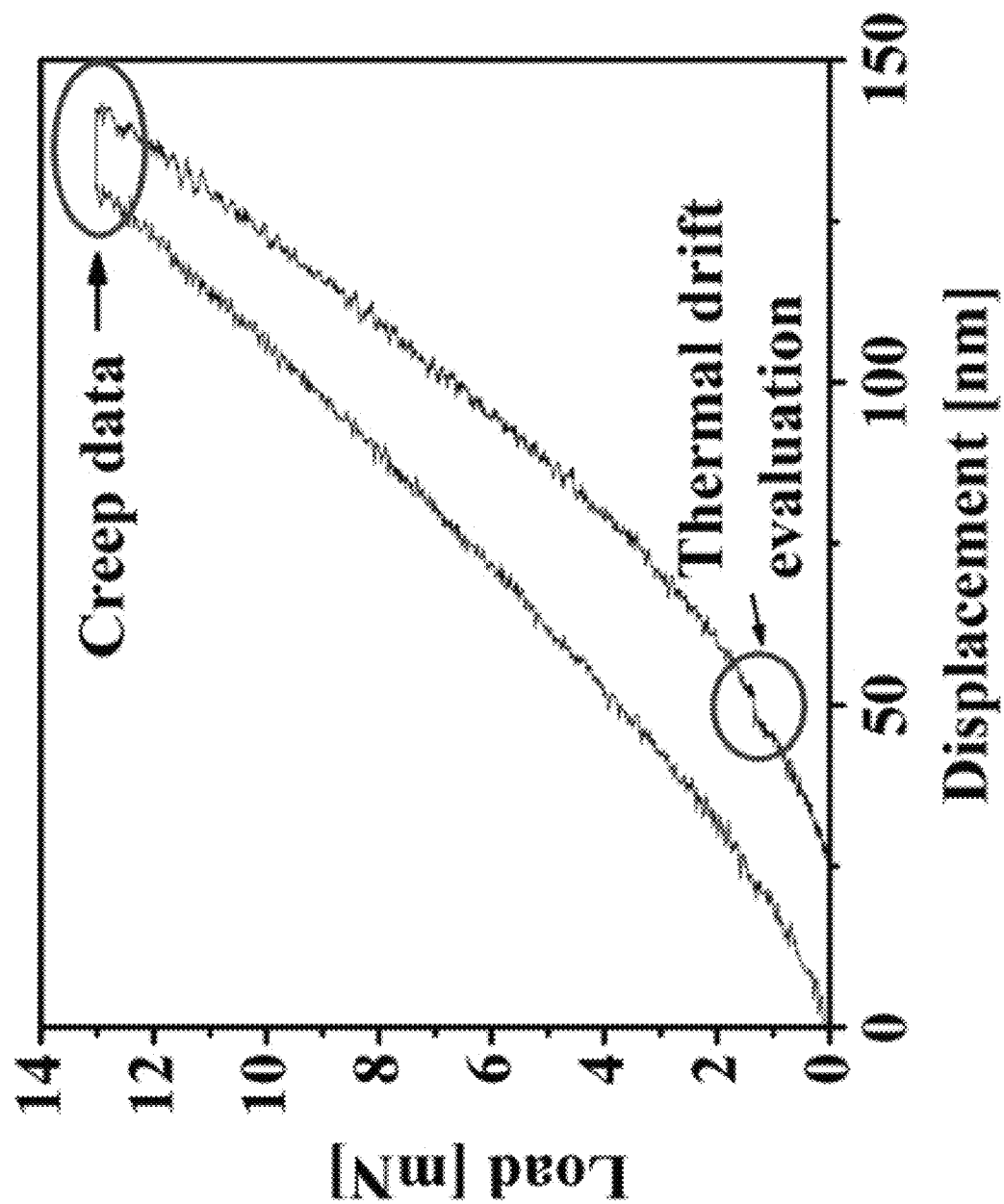
Figures 2, 2B:
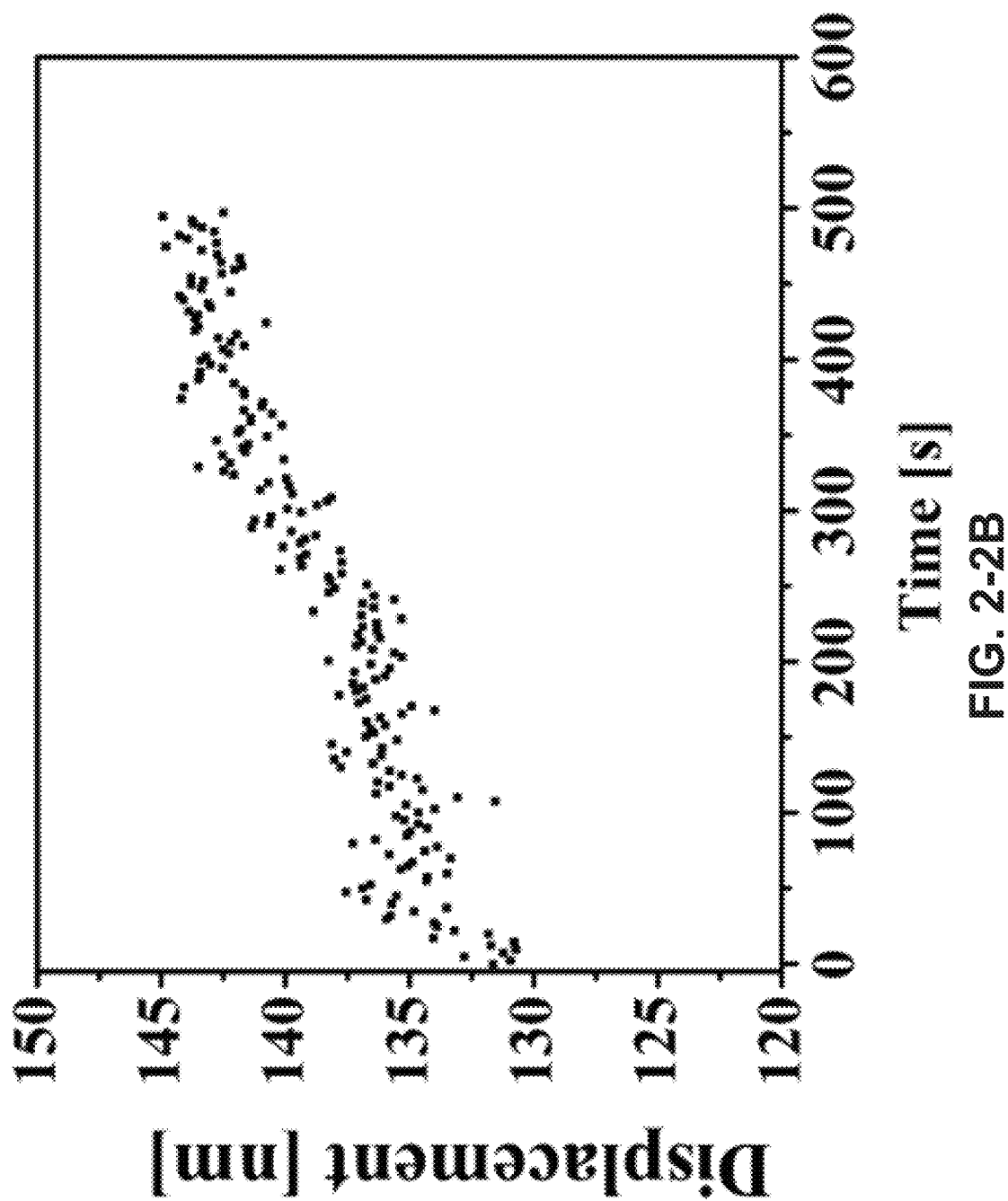
Figures 2, 2C:
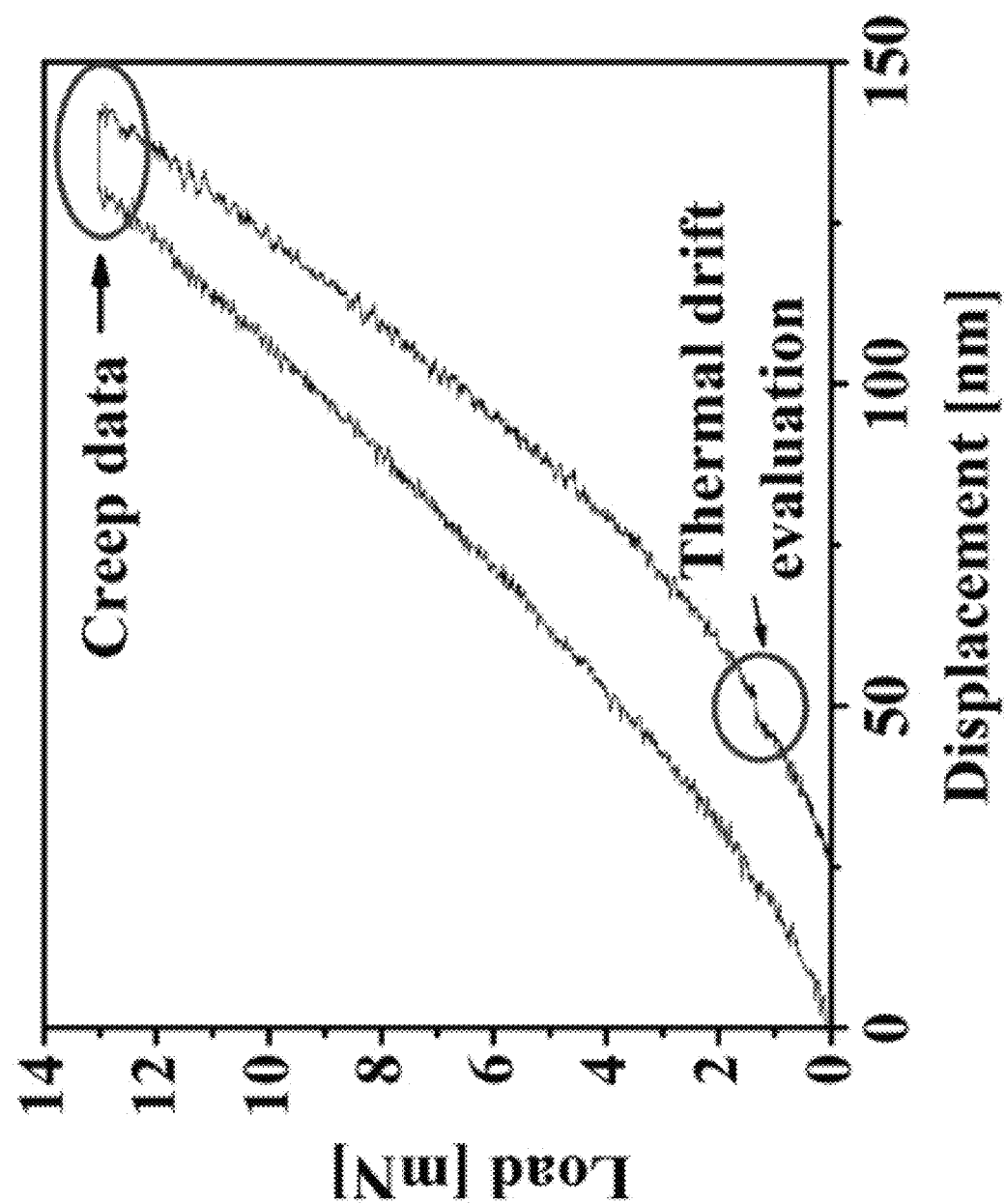
Figures 2, 2D:
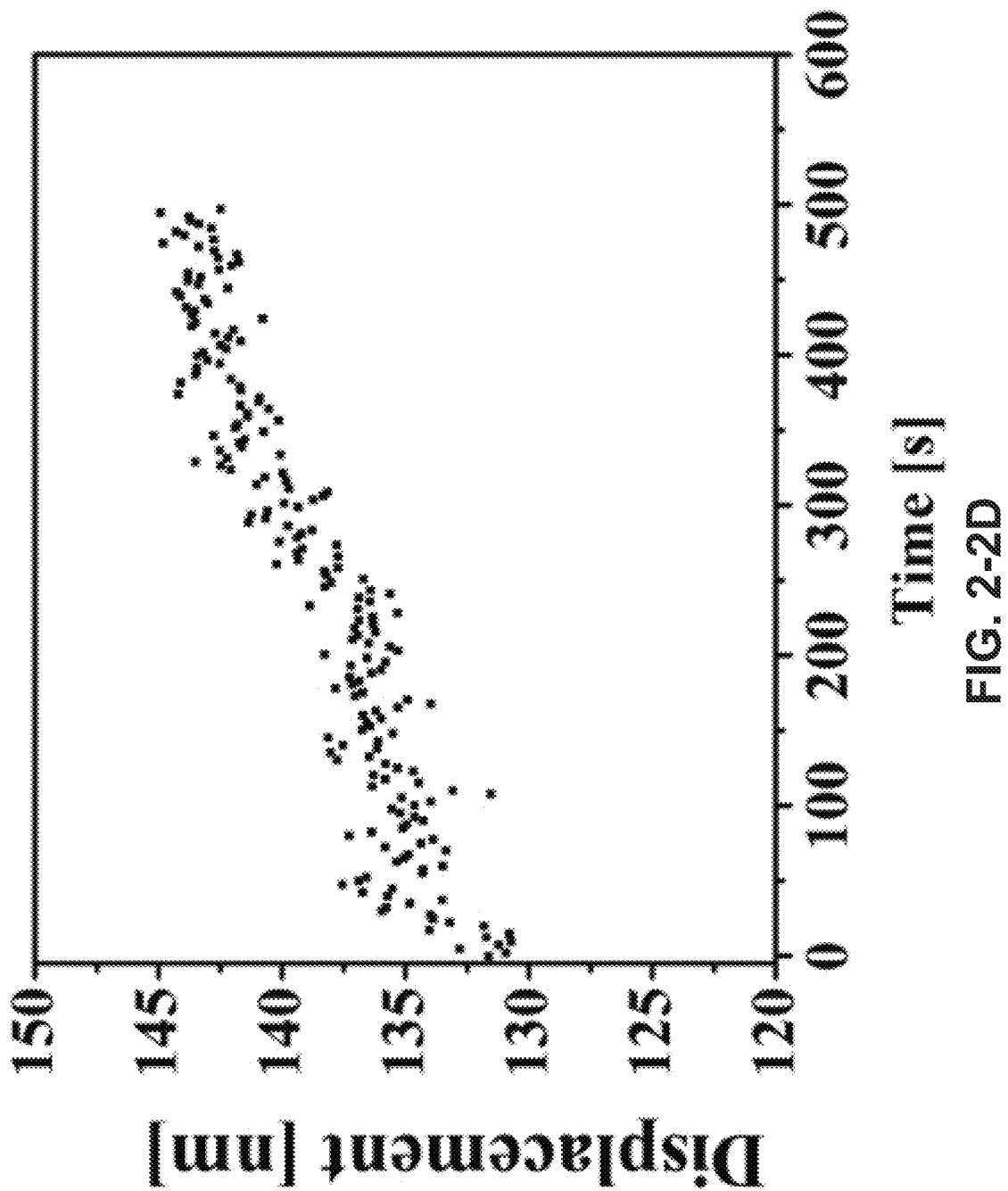
Figures 2, 3, 3A:
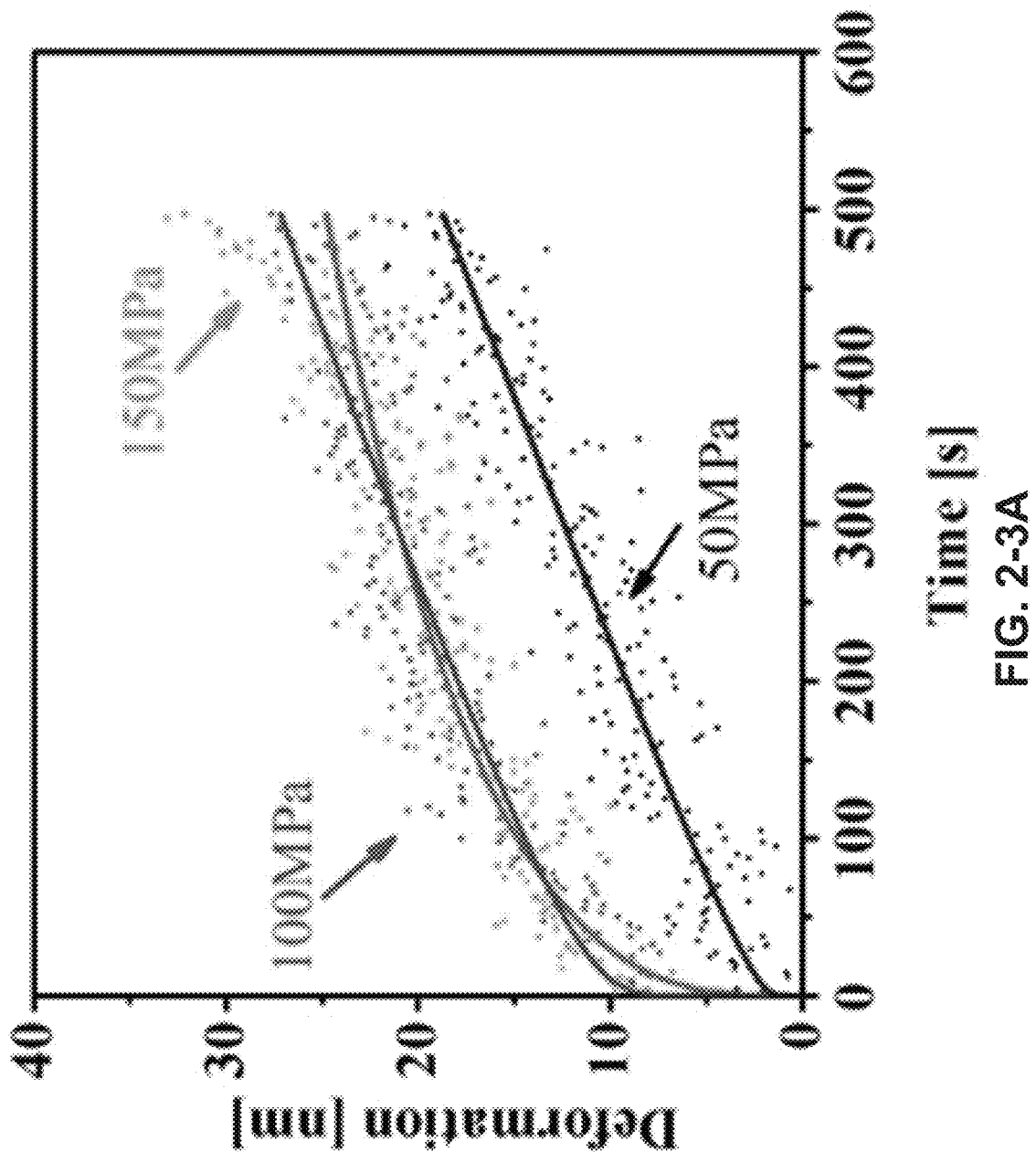
Figures 2, 3, 3B:
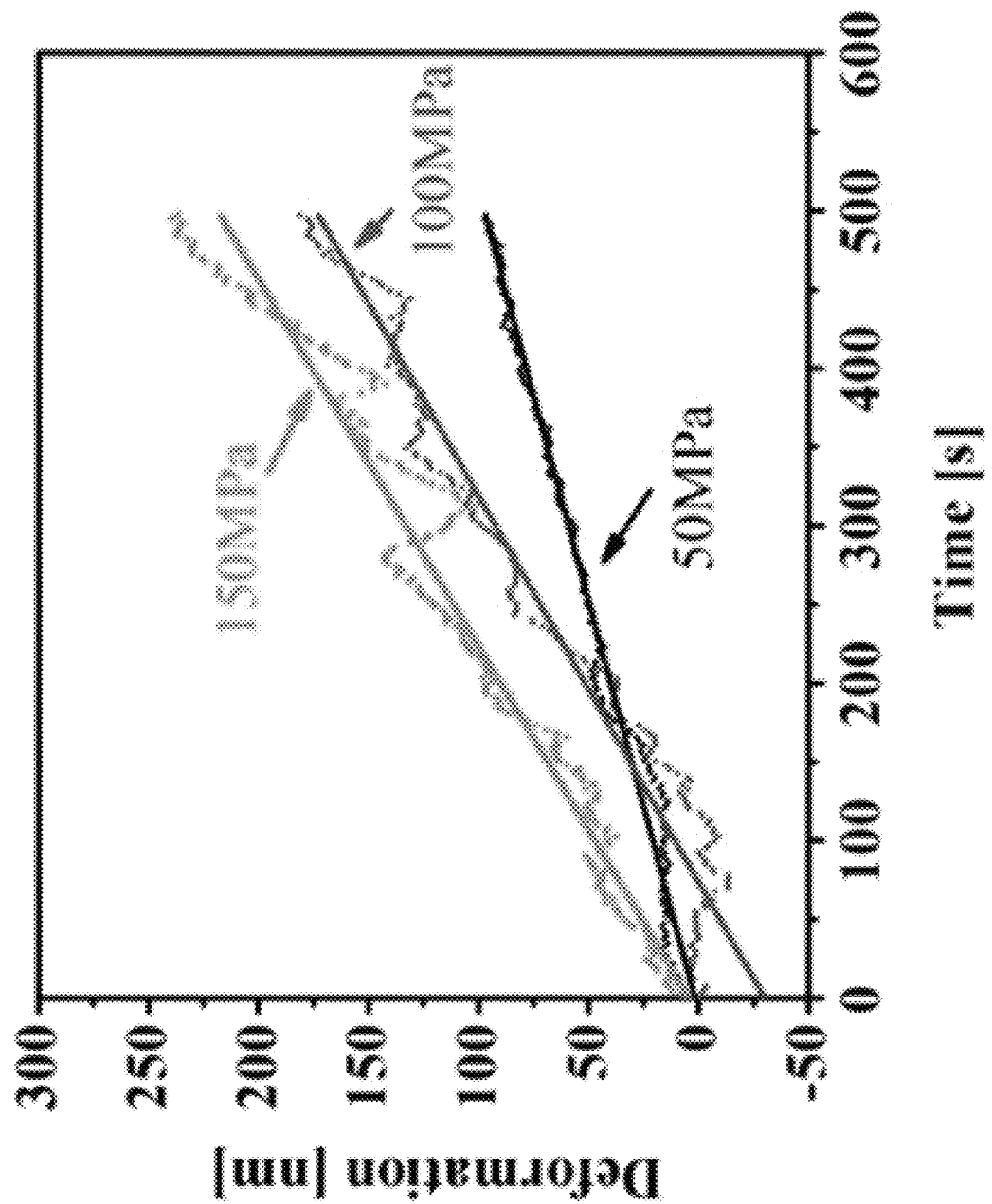
Figures 2, 3, 3C:
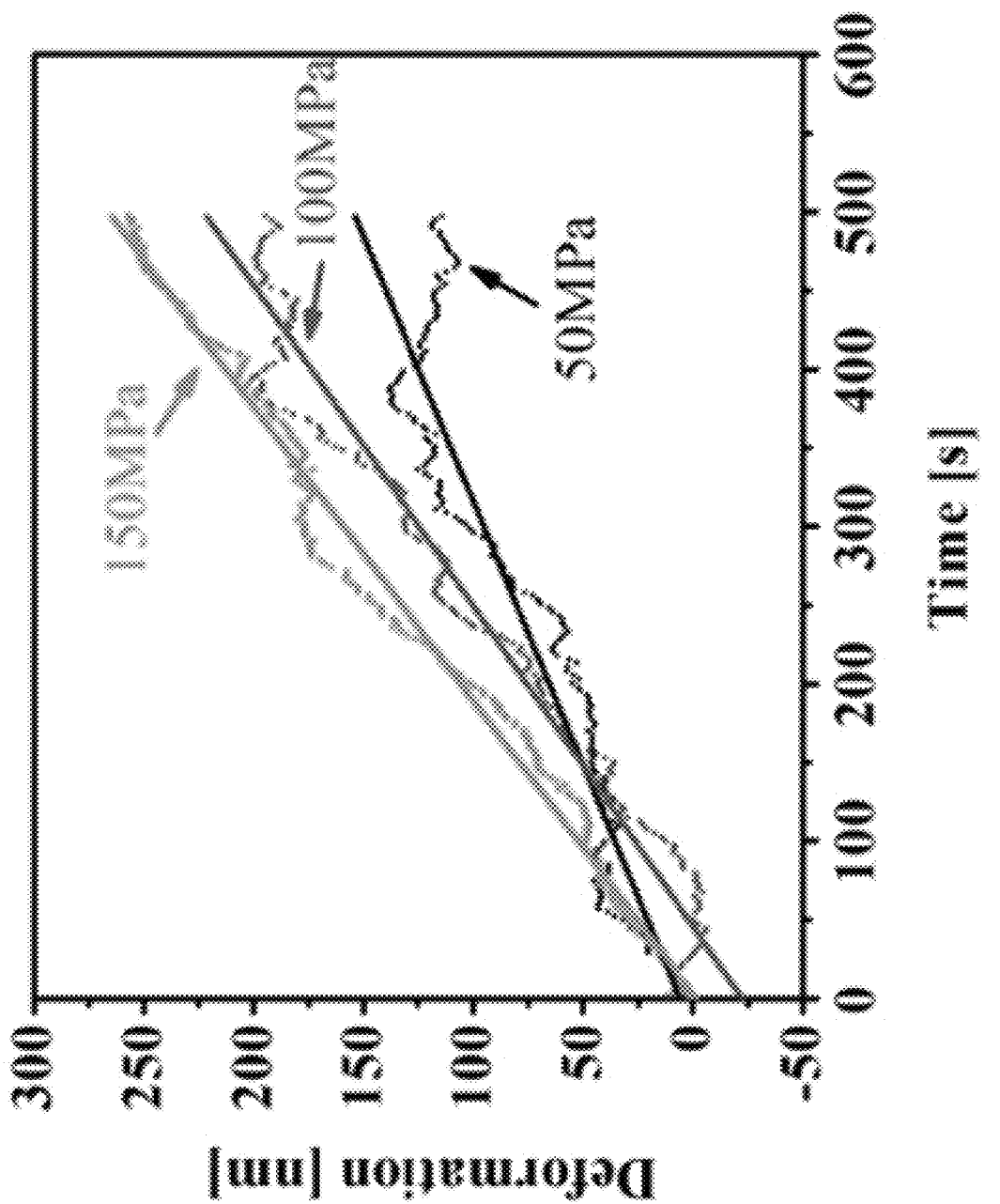
Figures 2, 3, 4, 4A:
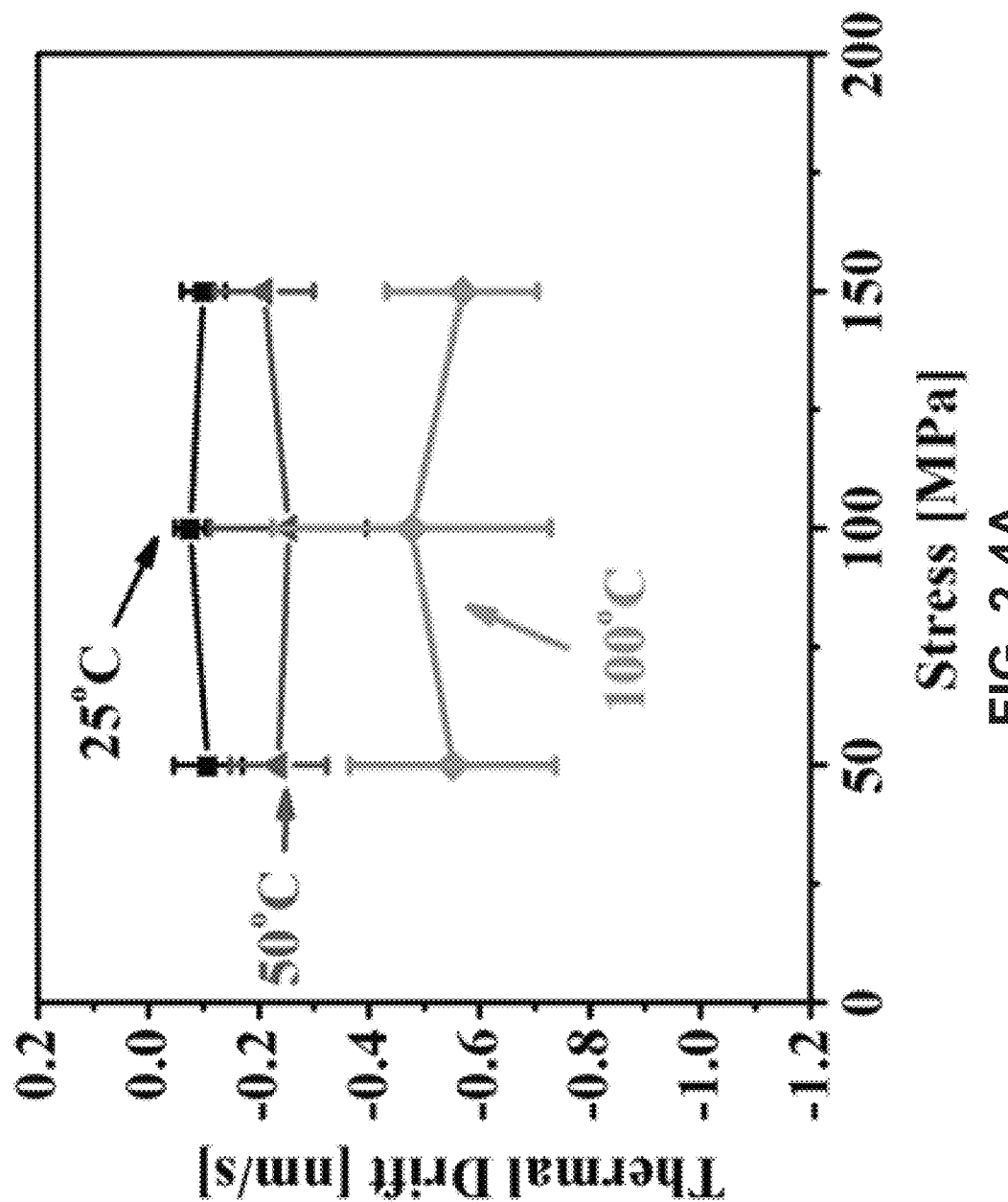
Figures 2, 3, 4, 4B:
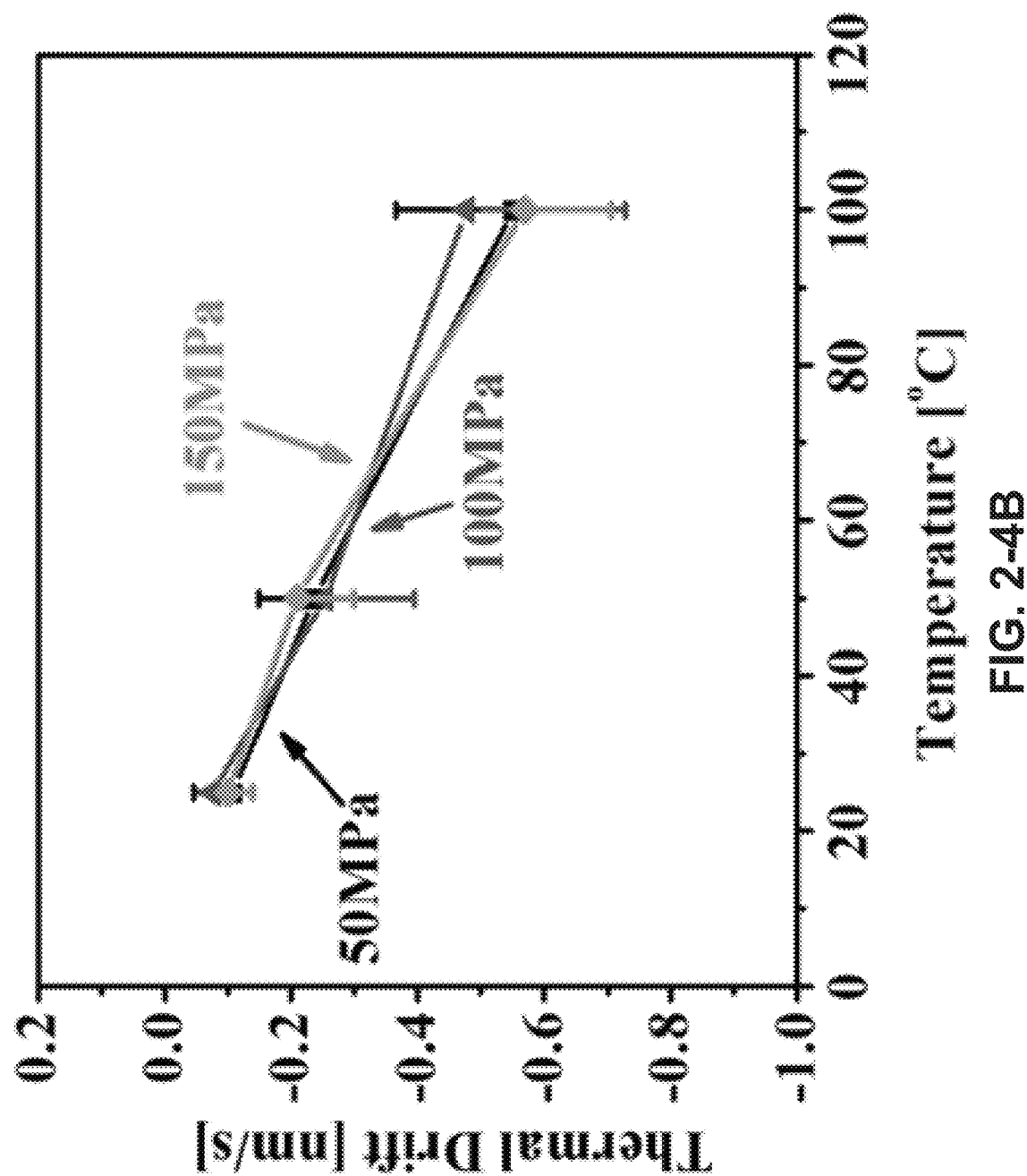
Figures 2, 3, 4, 5, 5A:
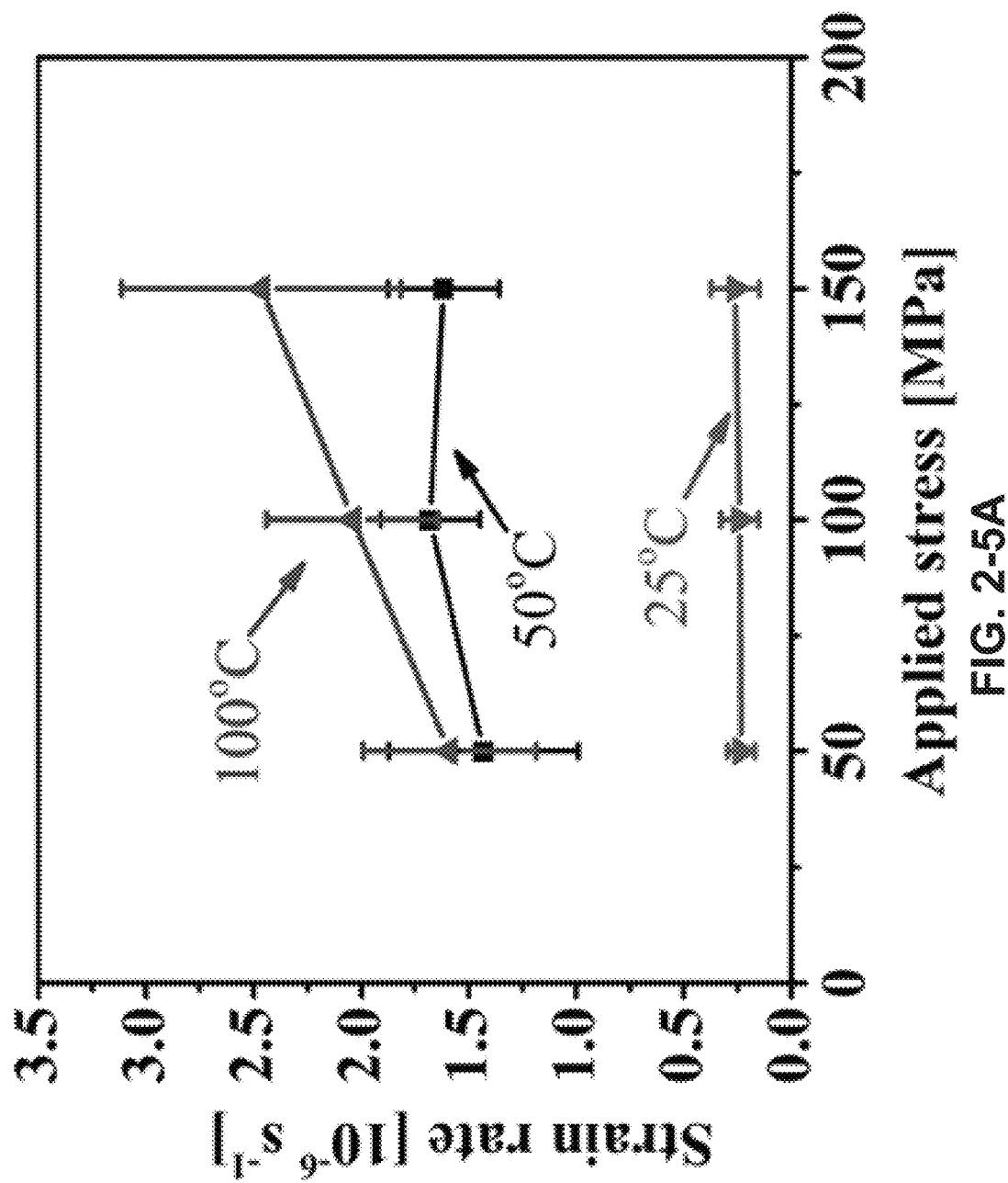
Figures 2, 3, 4, 5, 5B:
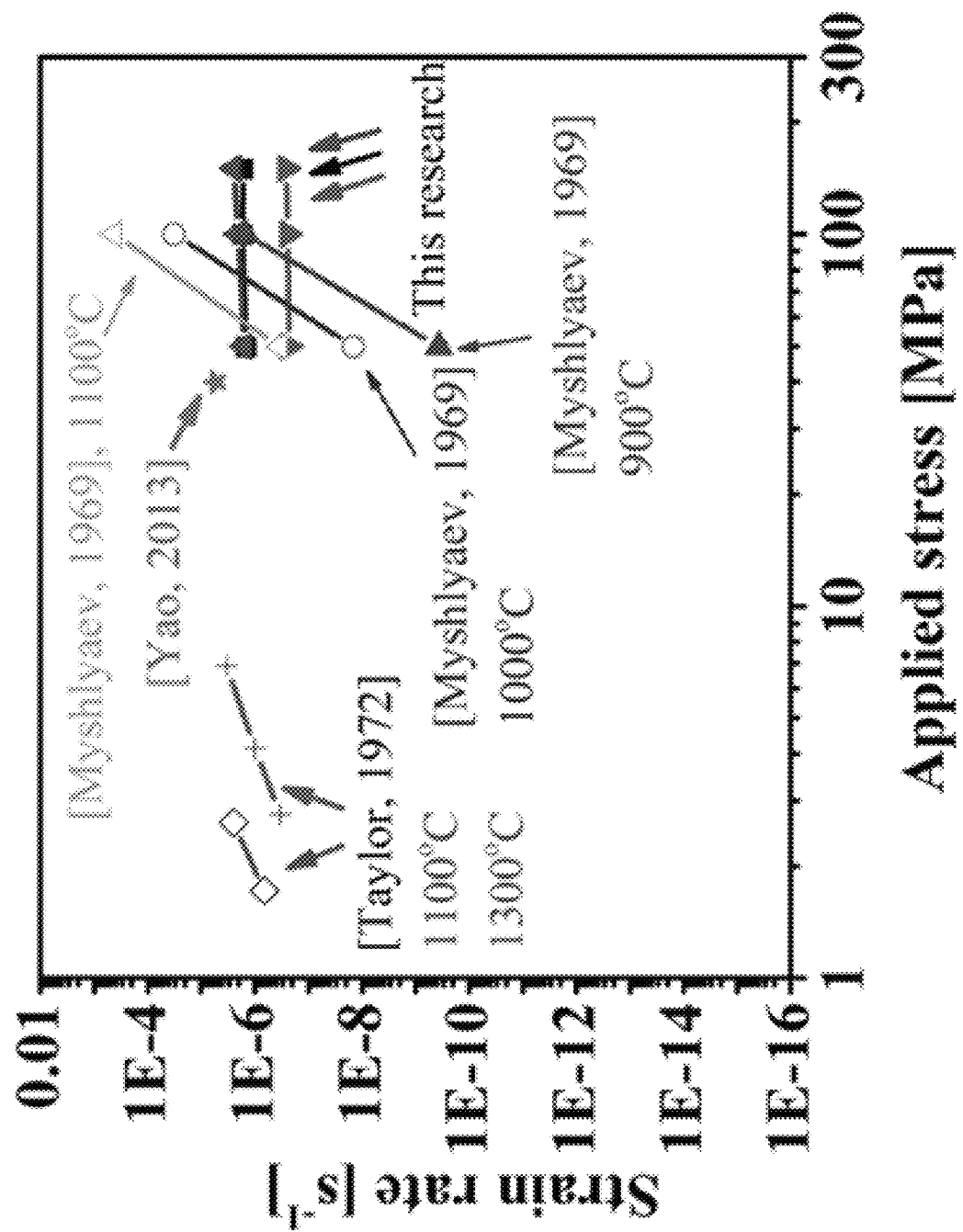
Figures 2, 3, 4, 5, 6, 6A:
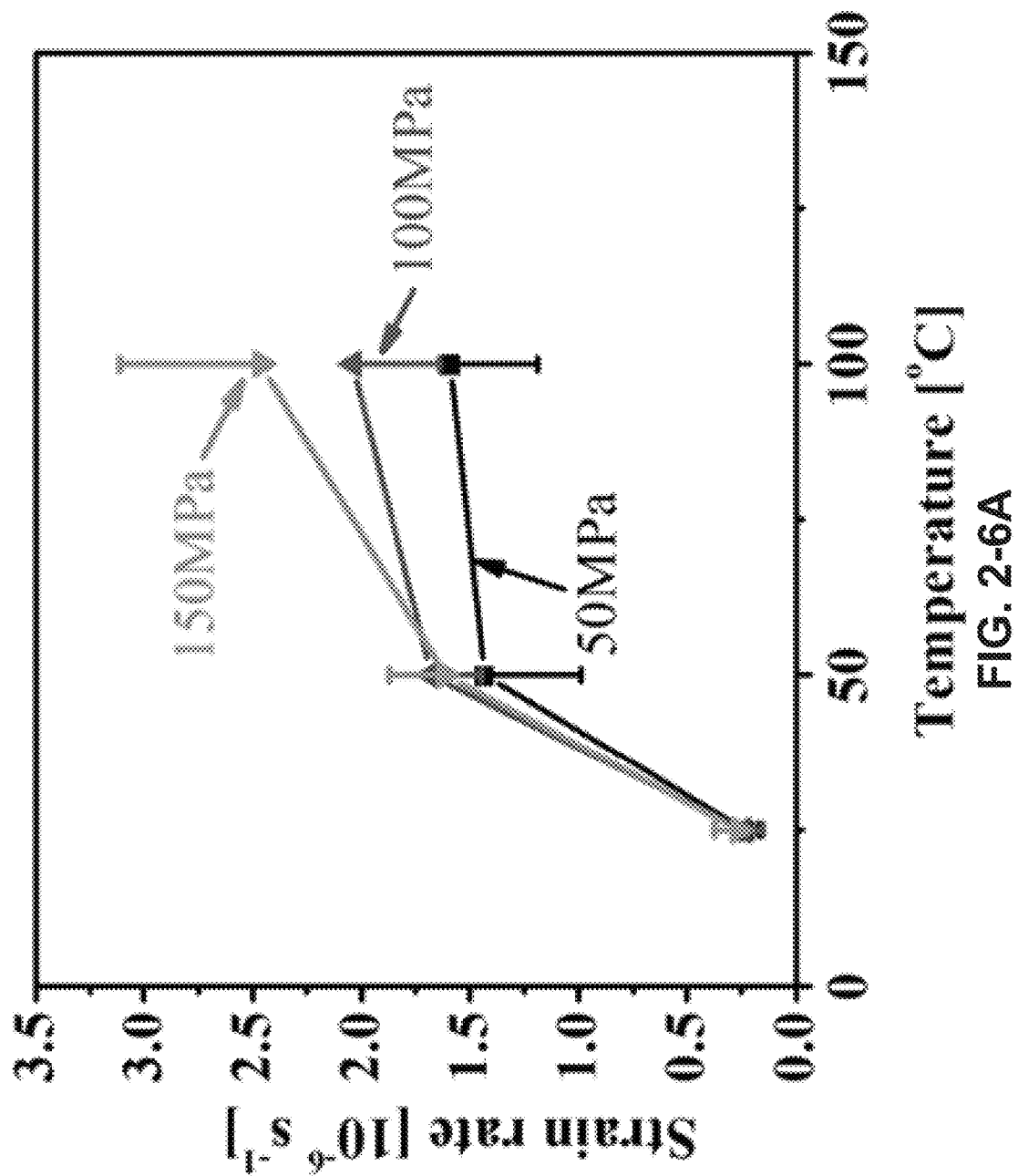
Figures 2, 3, 4, 5, 6, 6B:
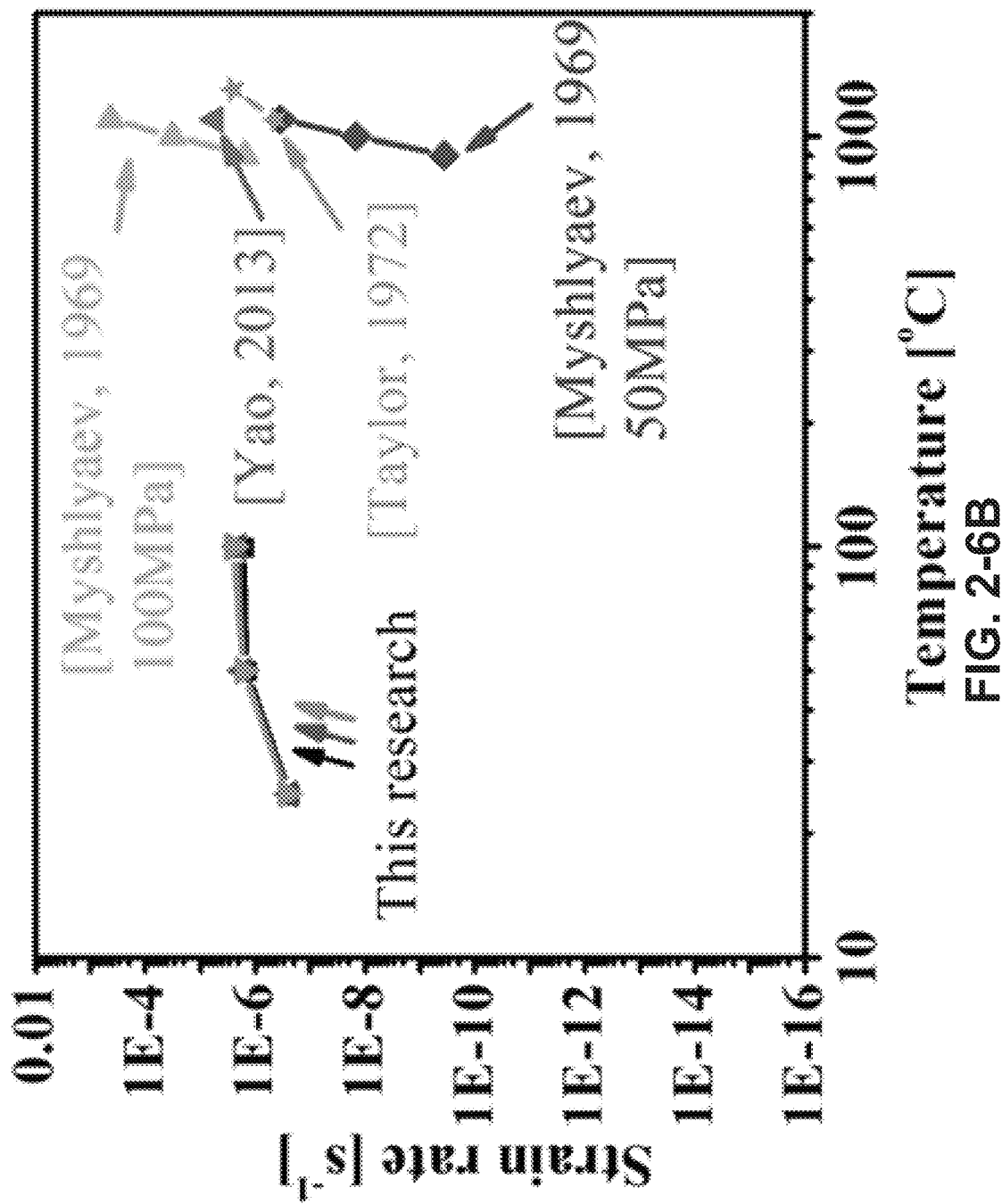
Figures 2, 3, 4, 5, 6, 7:
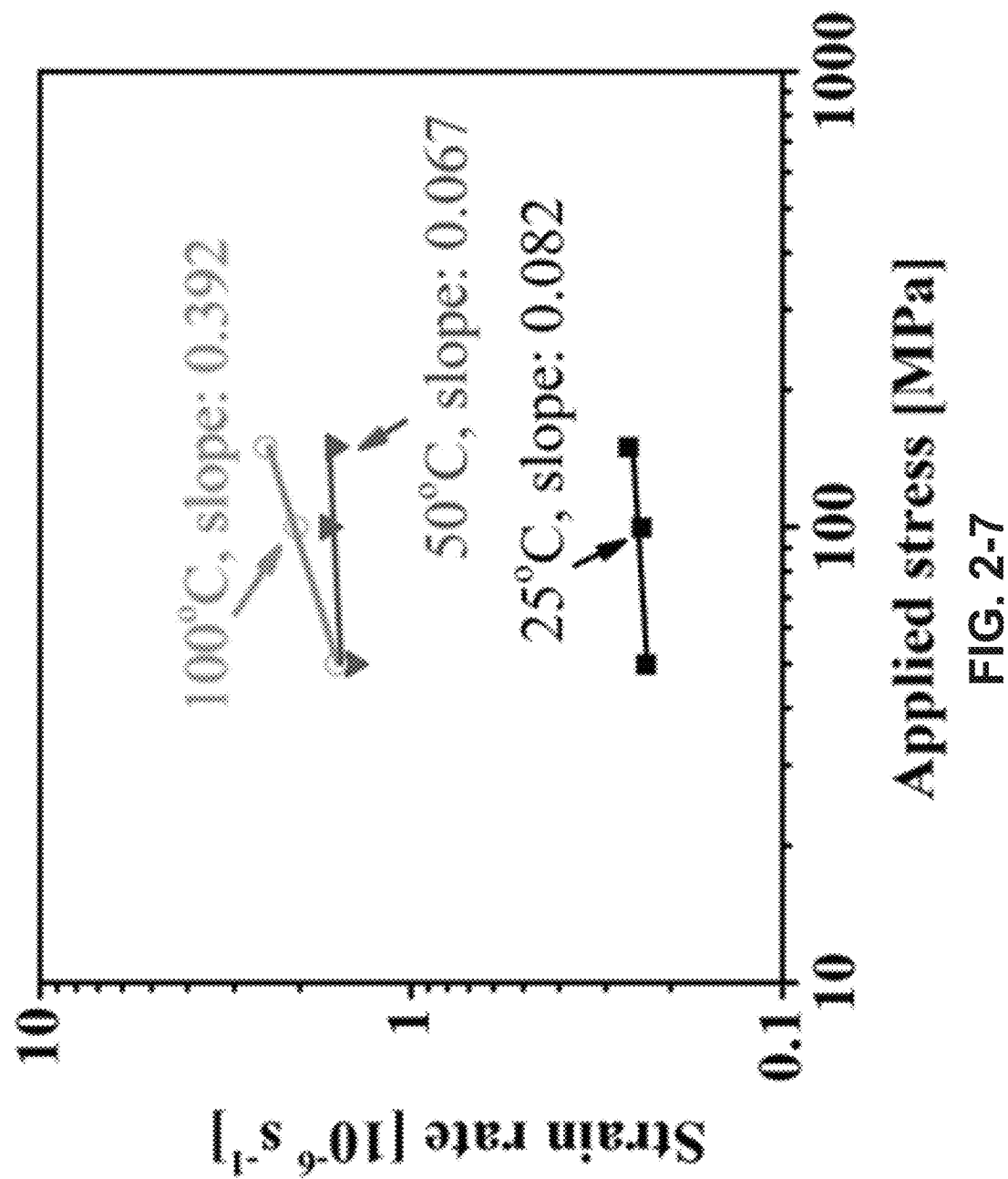
Figures 2, 3, 4, 5, 6, 7, 8, 8A:
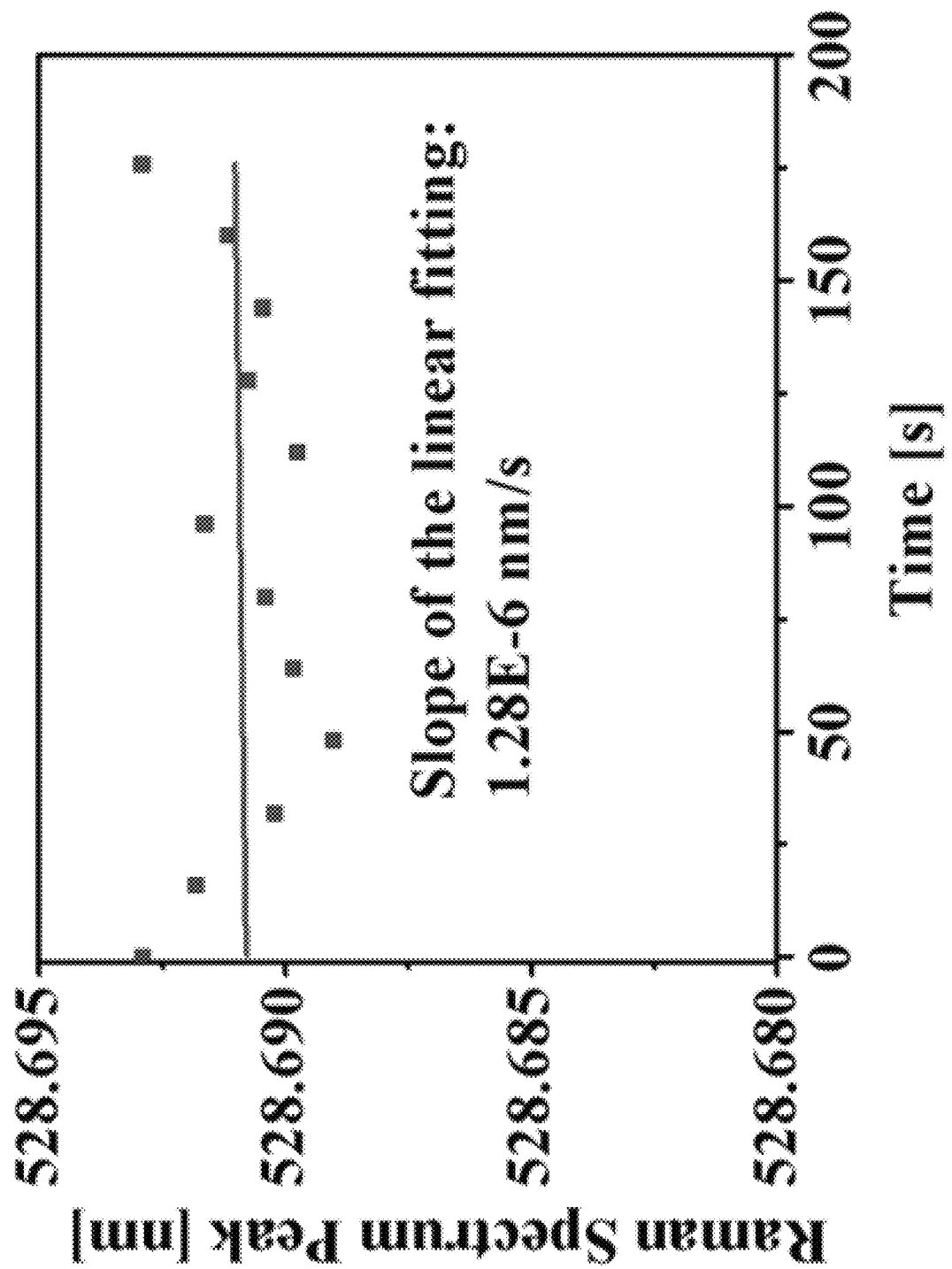
Figures 2, 3, 4, 5, 6, 7, 8, 8B:
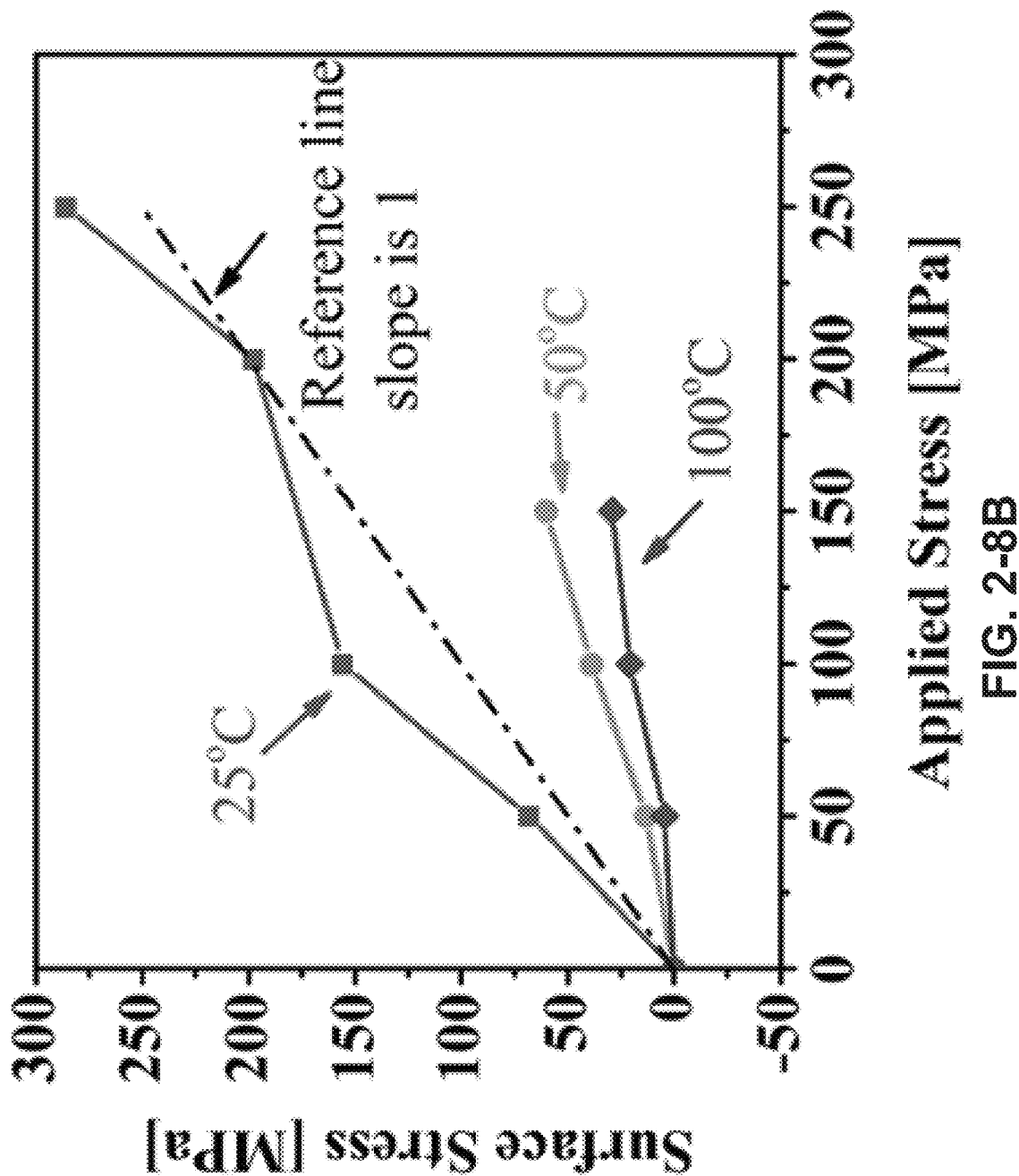
Figures 1A, 3:
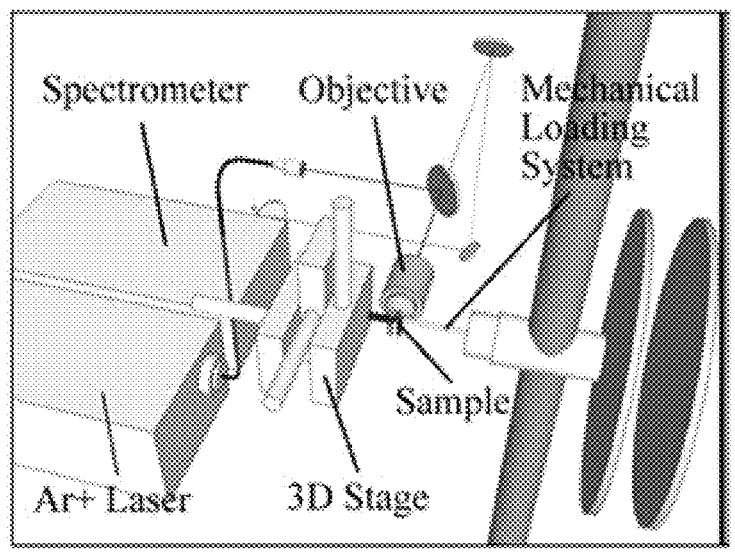
Figures 1B, 3:
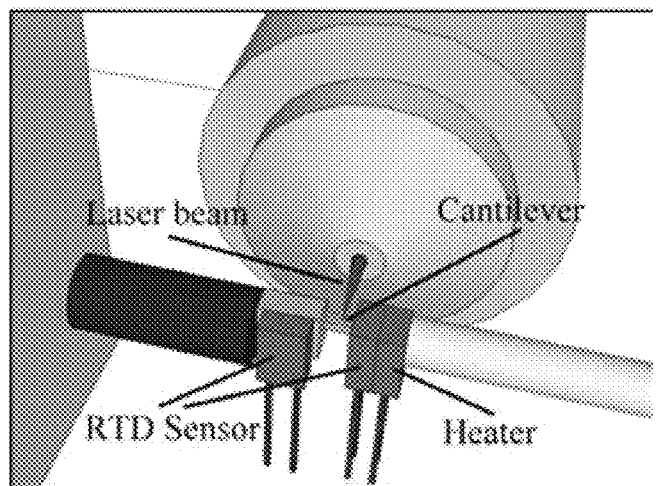
Figures 1C, 3:
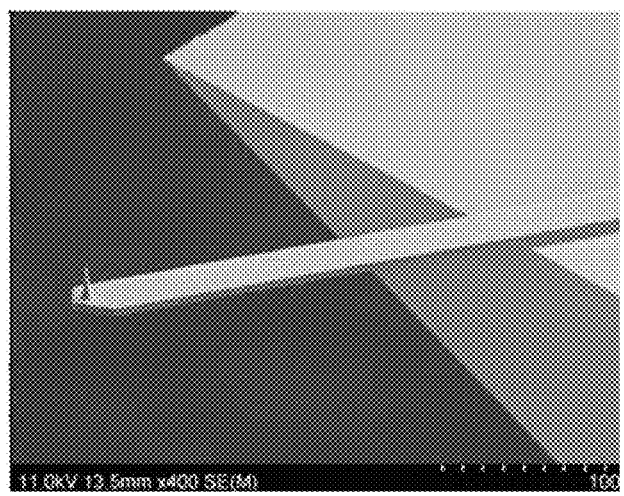
Figures 2A, 3:
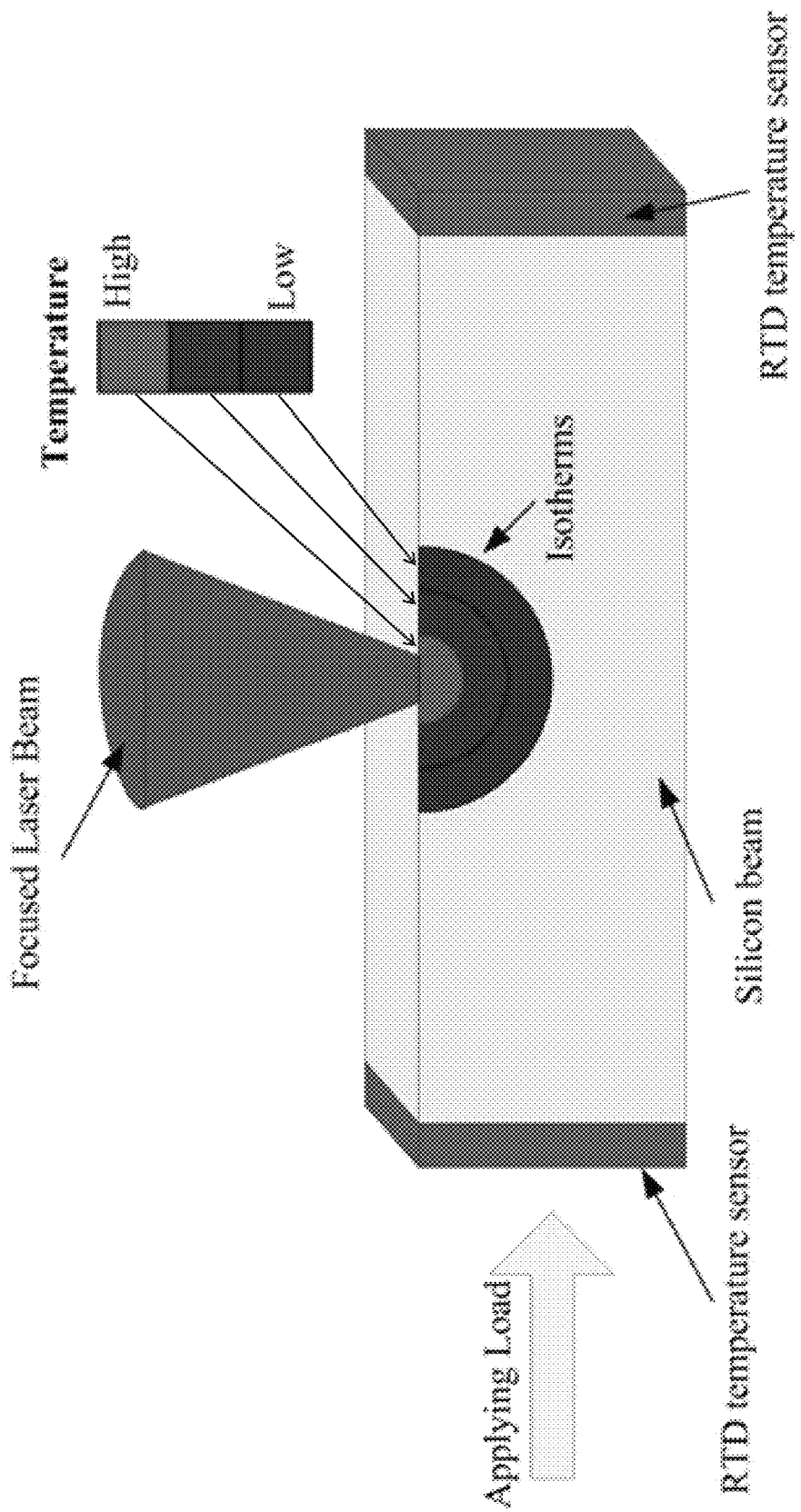
Figures 2B, 3:
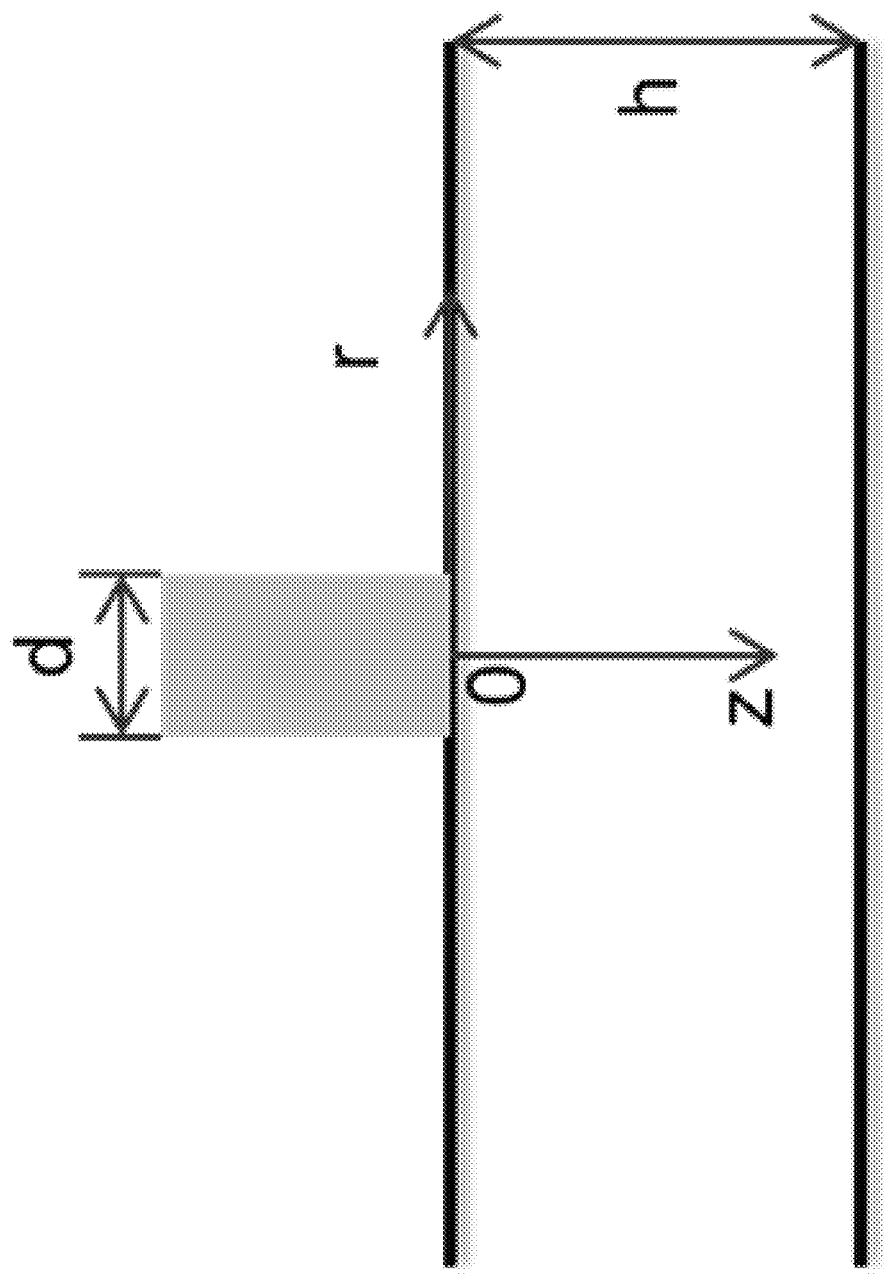
Figures 3, 3A:
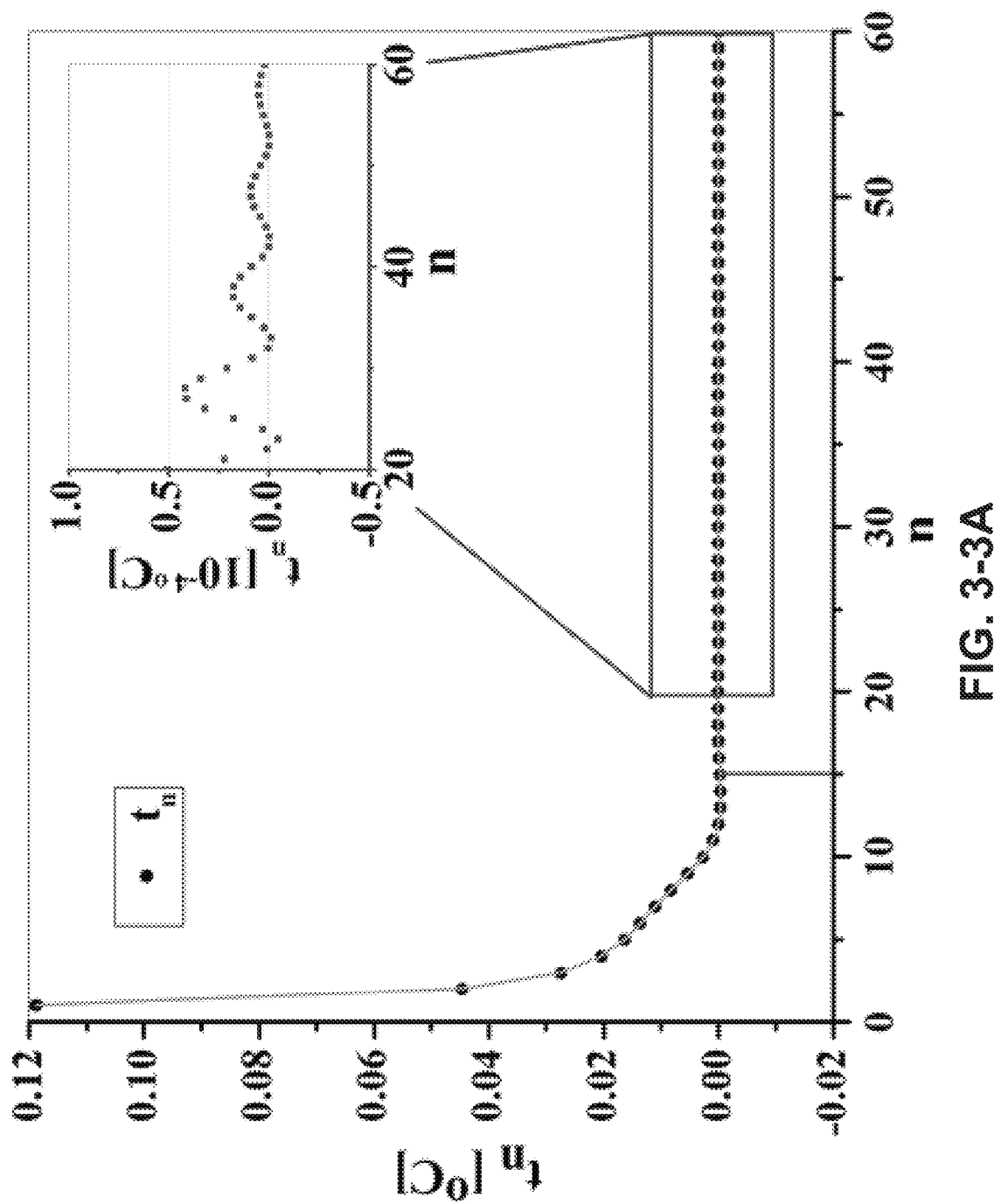
Figures 3, 3B:
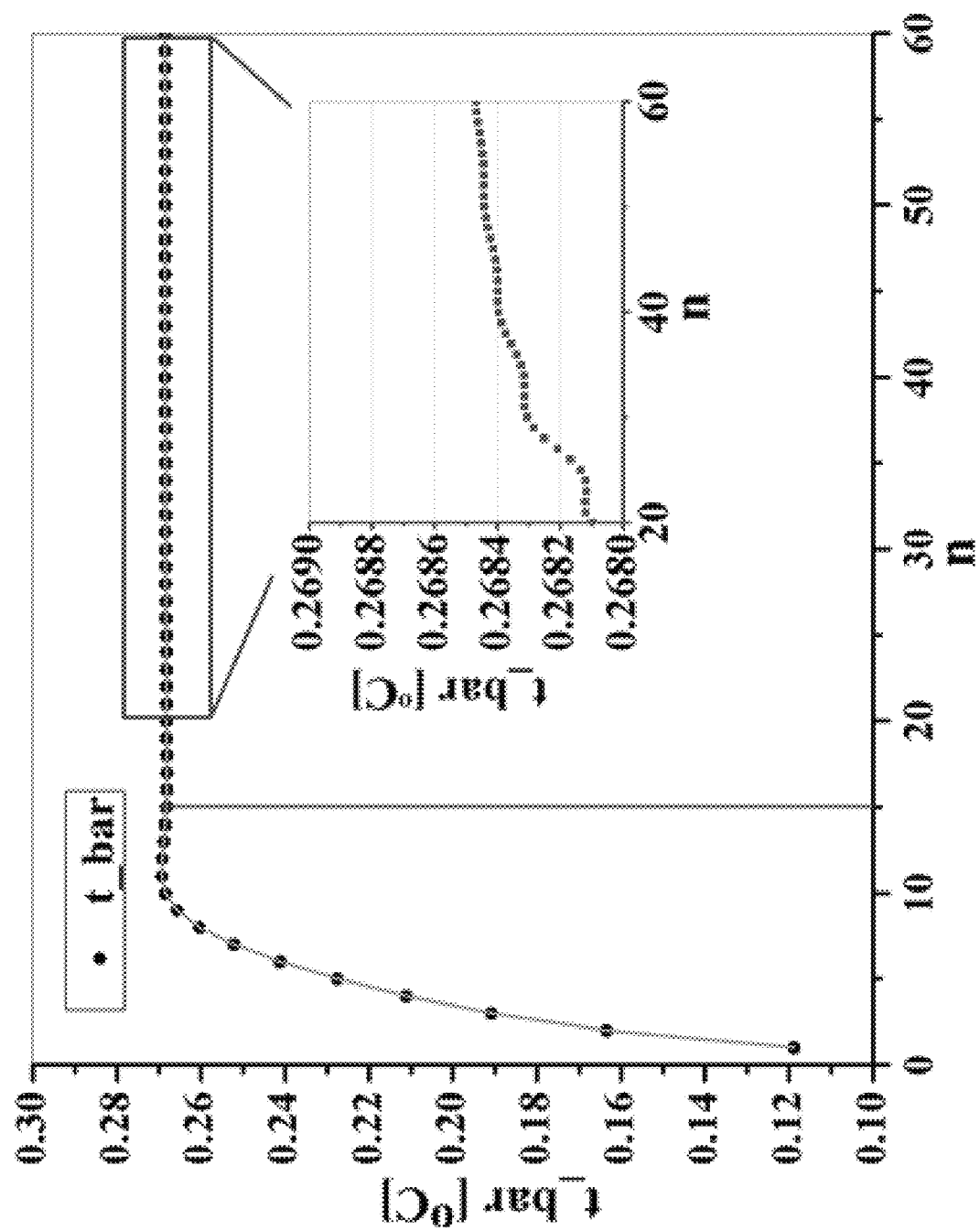
Figures 1, 3, 4:
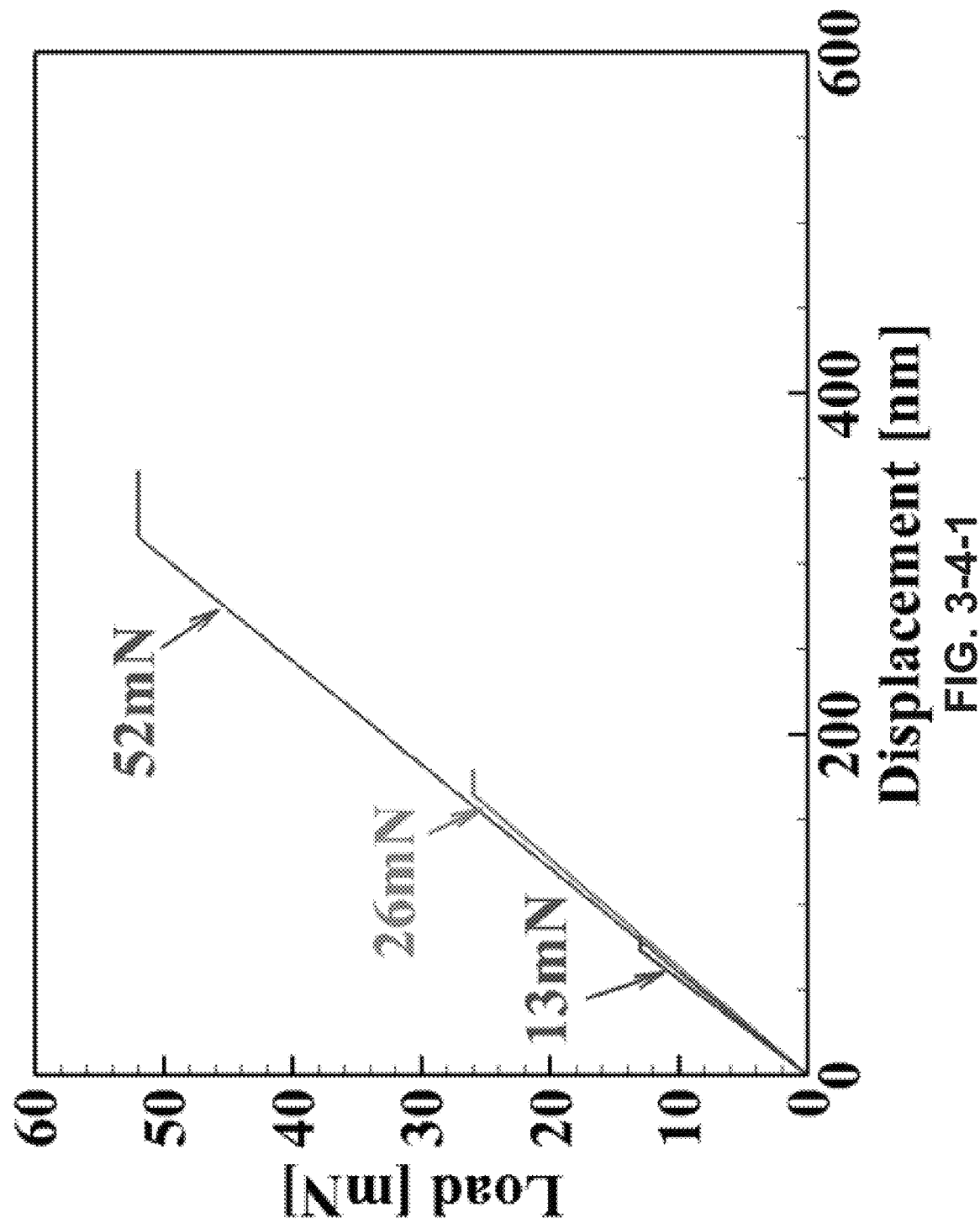
Figures 2A, 3, 4:
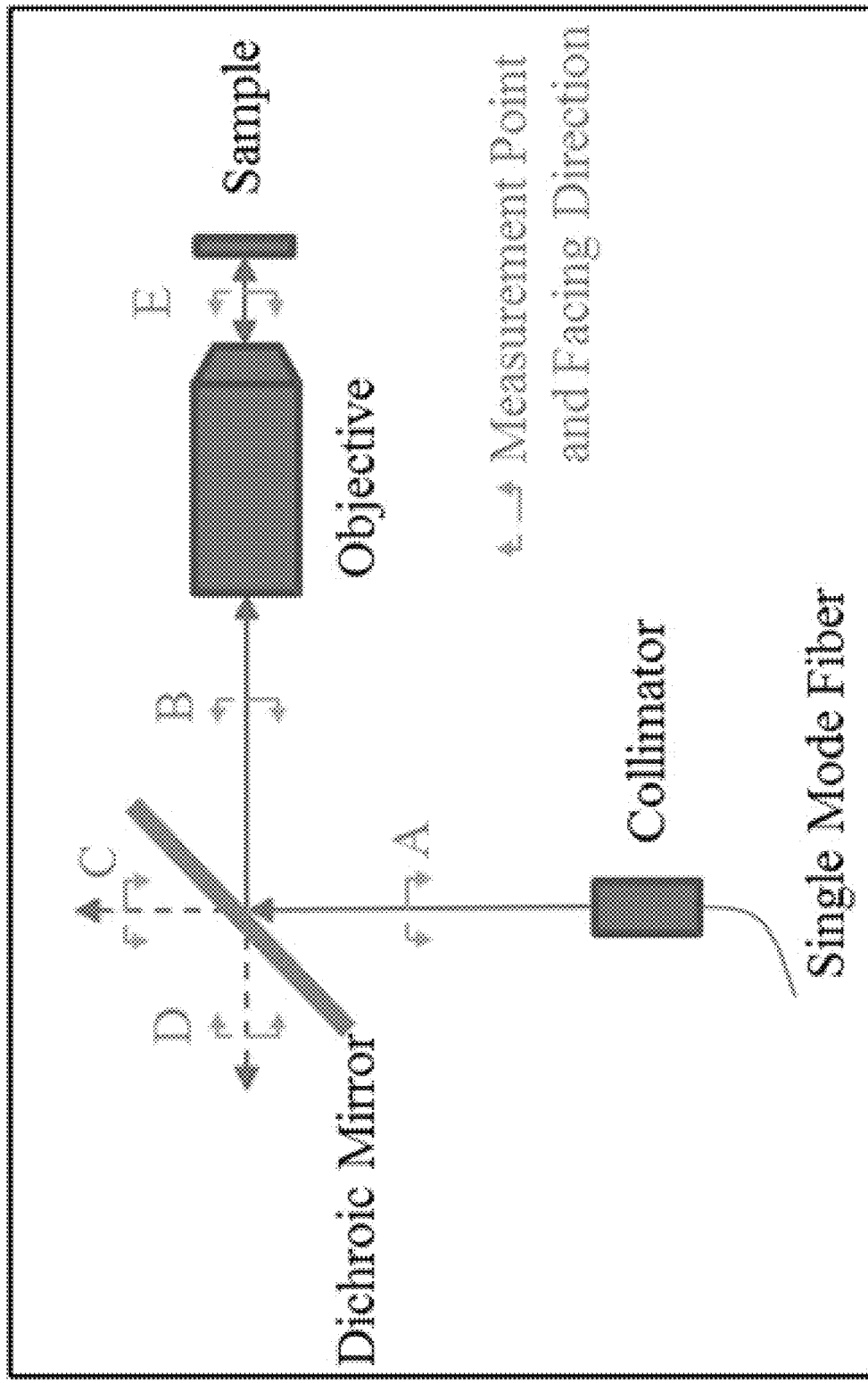
Figures 2B, 3, 4:
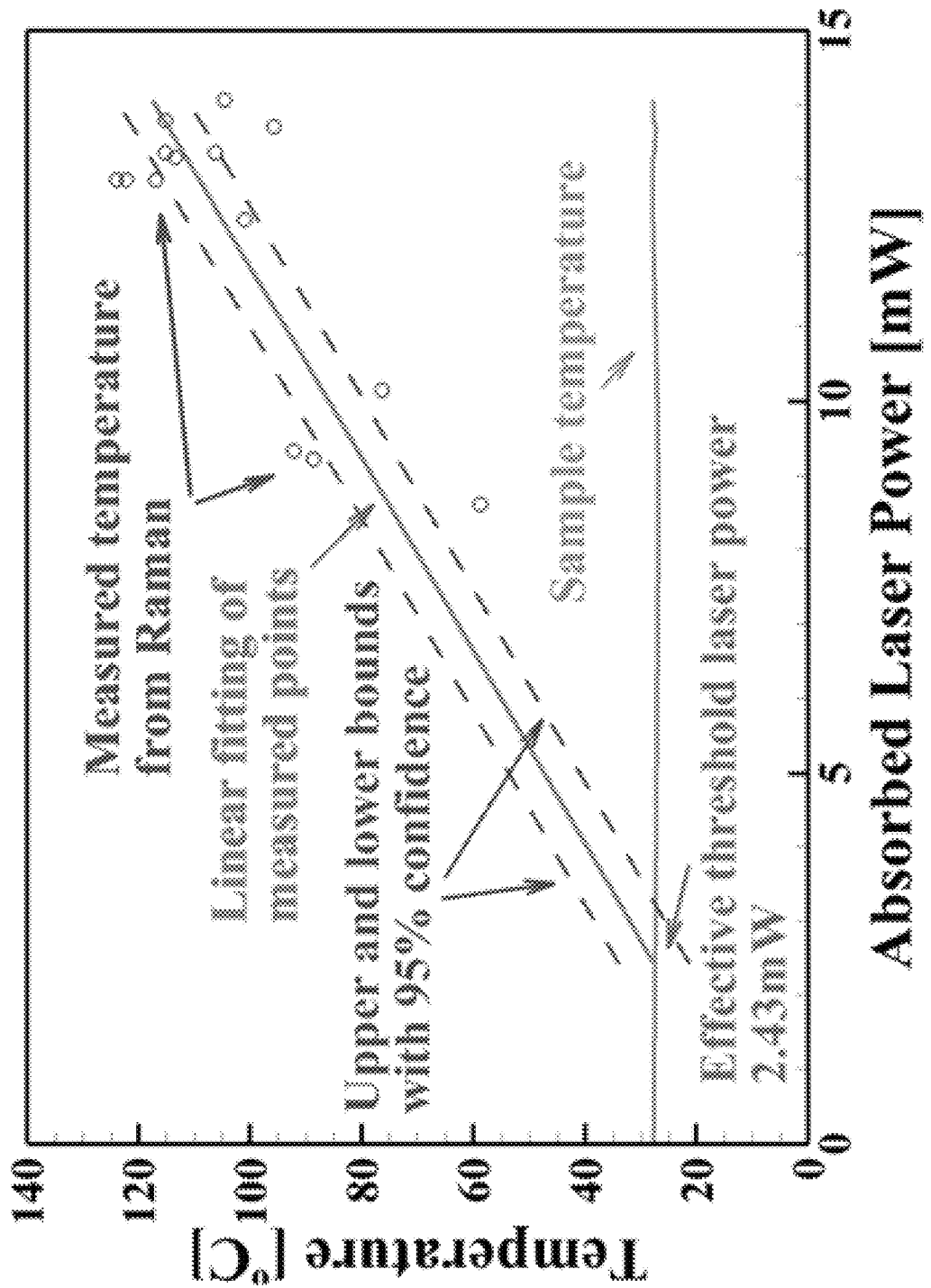
Figures 3, 4, 5, 5A:
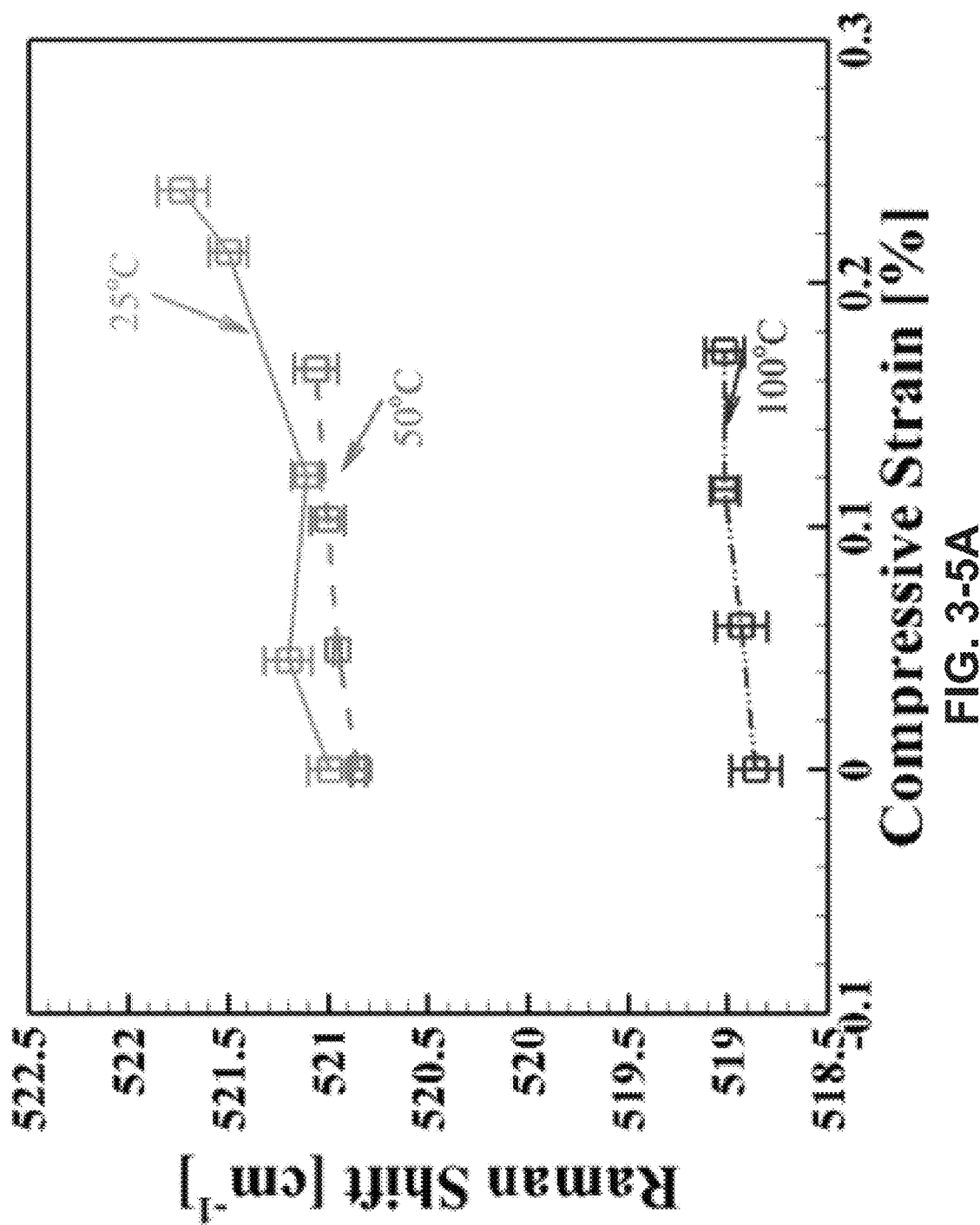
Figures 3, 4, 5, 5B:
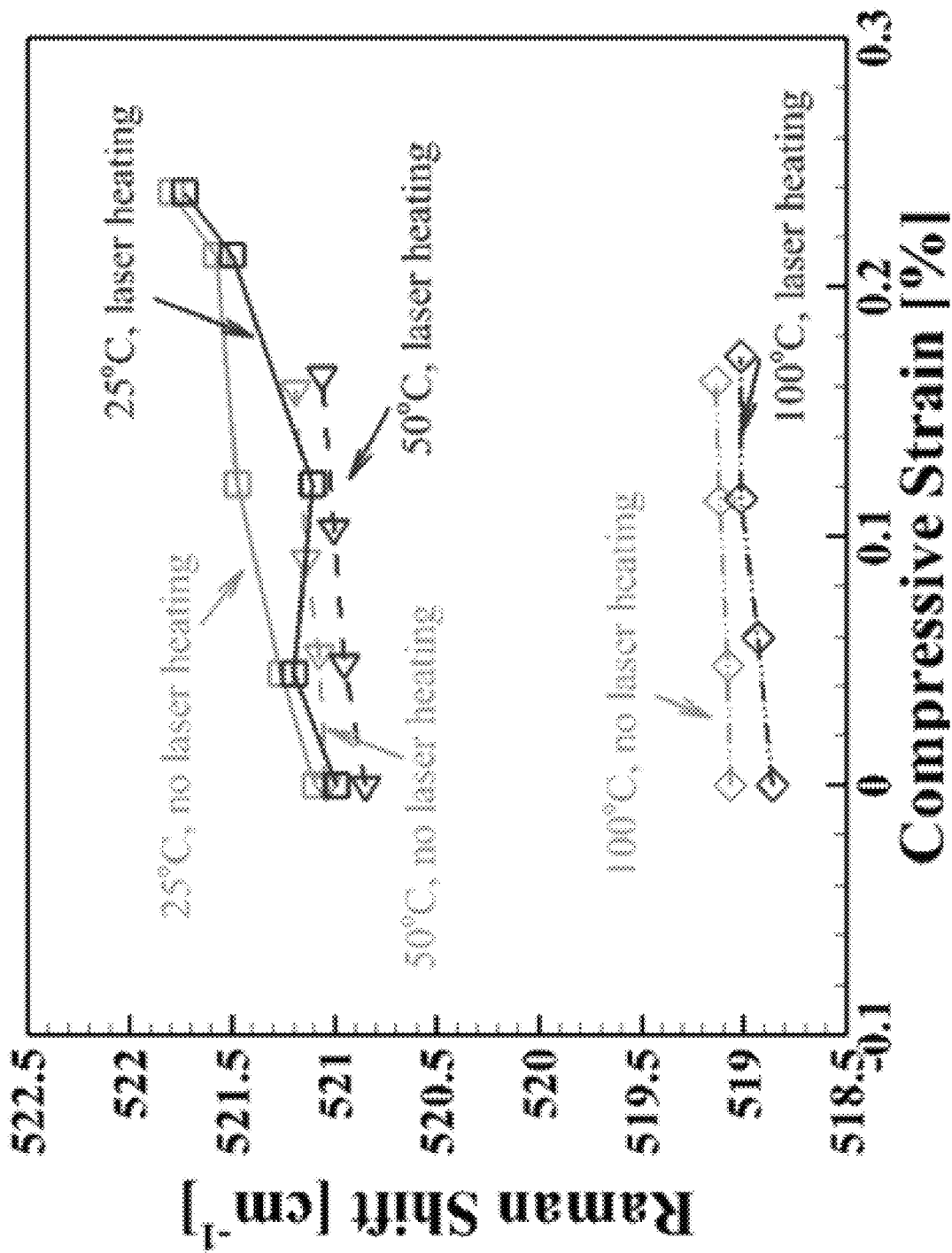
Figures 3, 4, 5, 6, 6A:
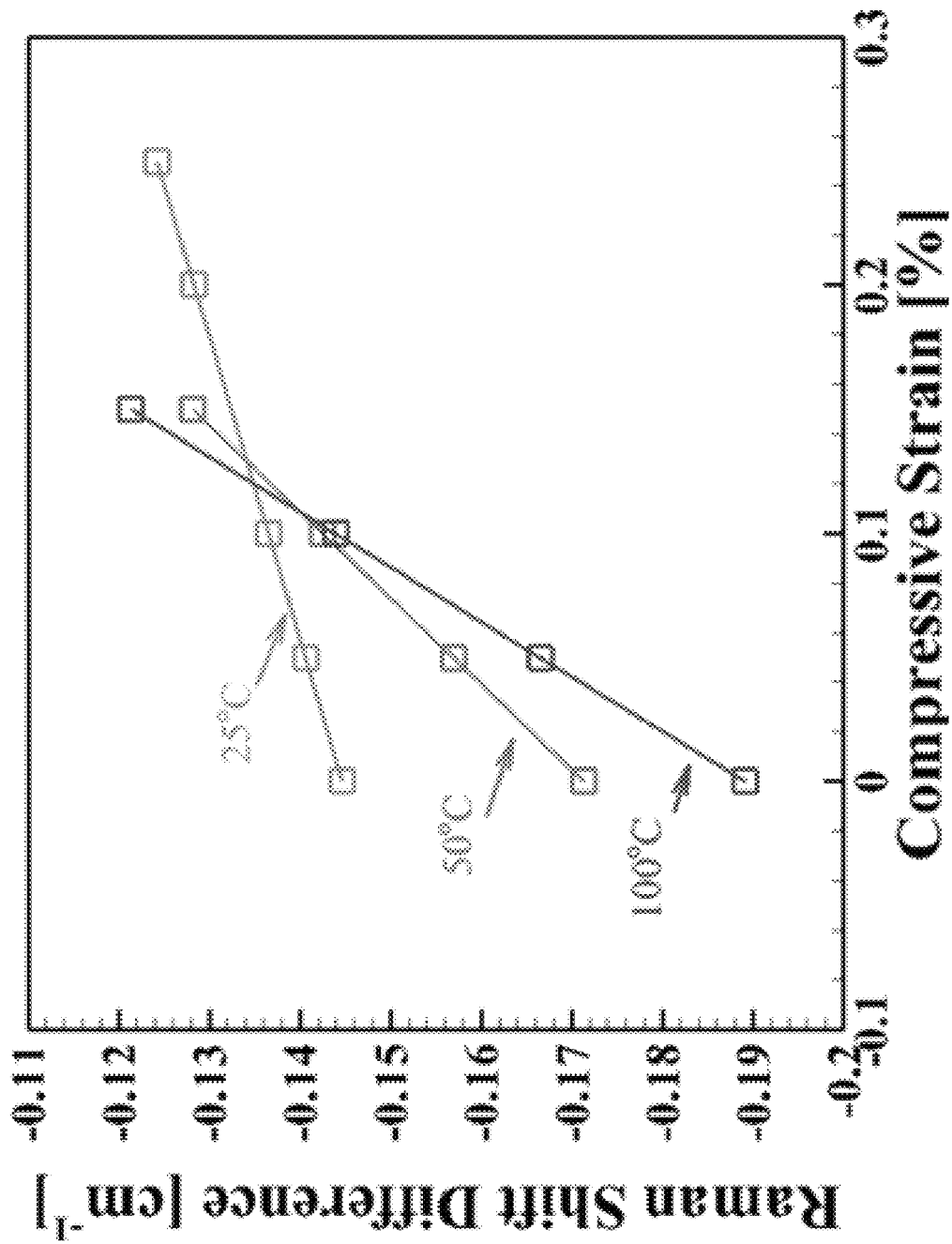
Figures 3, 4, 5, 6, 6B:
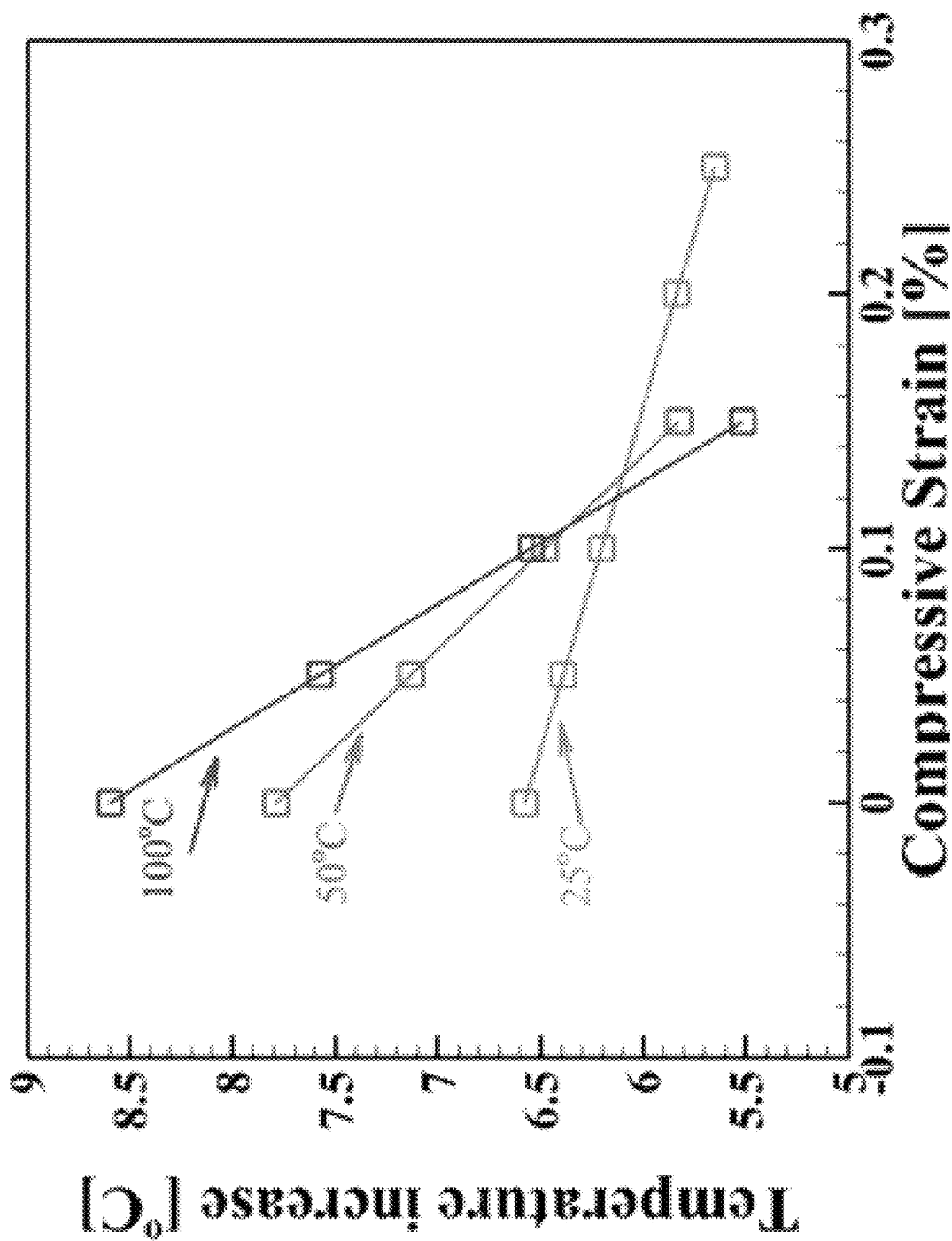
Figures 3, 4, 5, 6, 7, 7A:
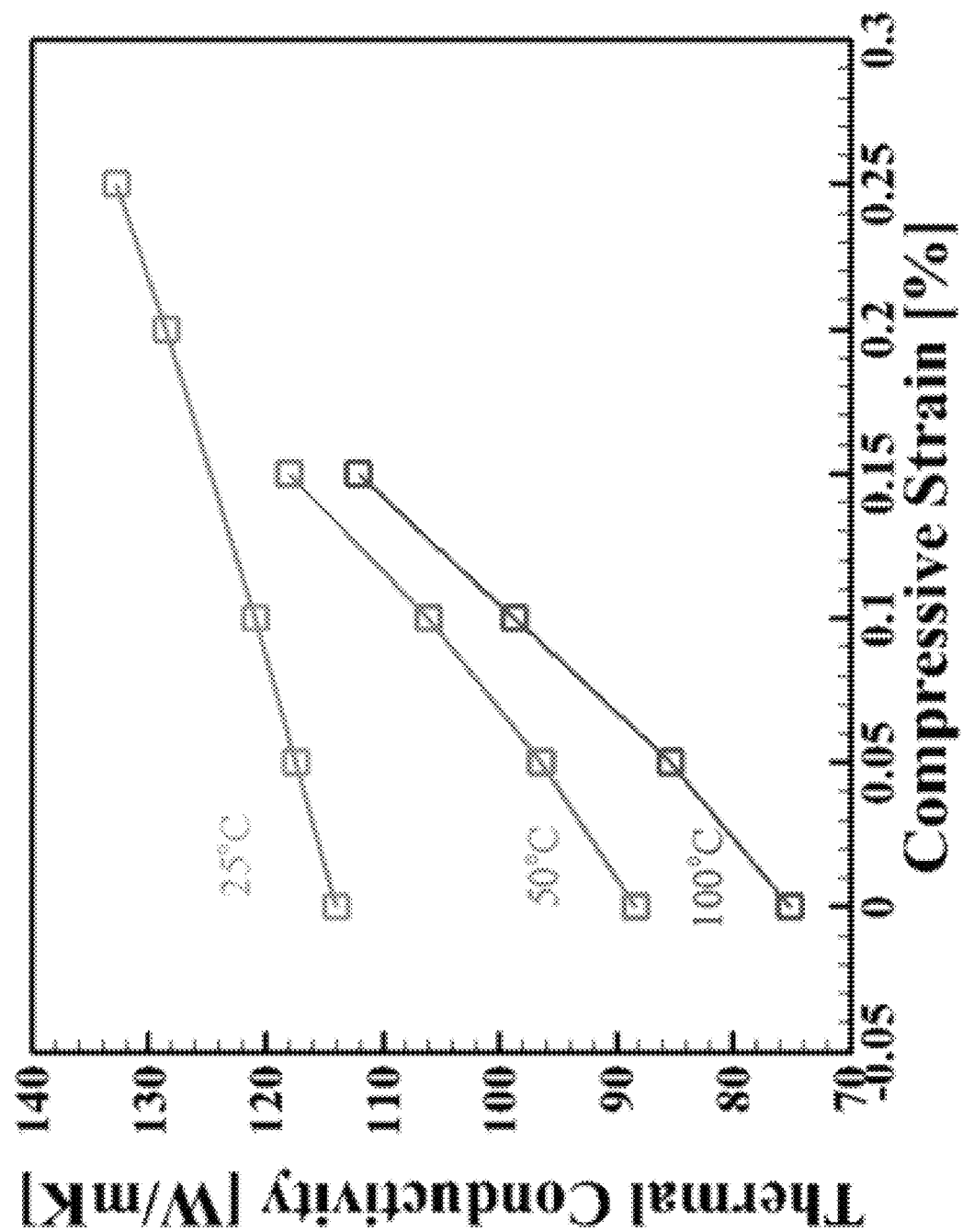
Figures 3, 4, 5, 6, 7, 7B:
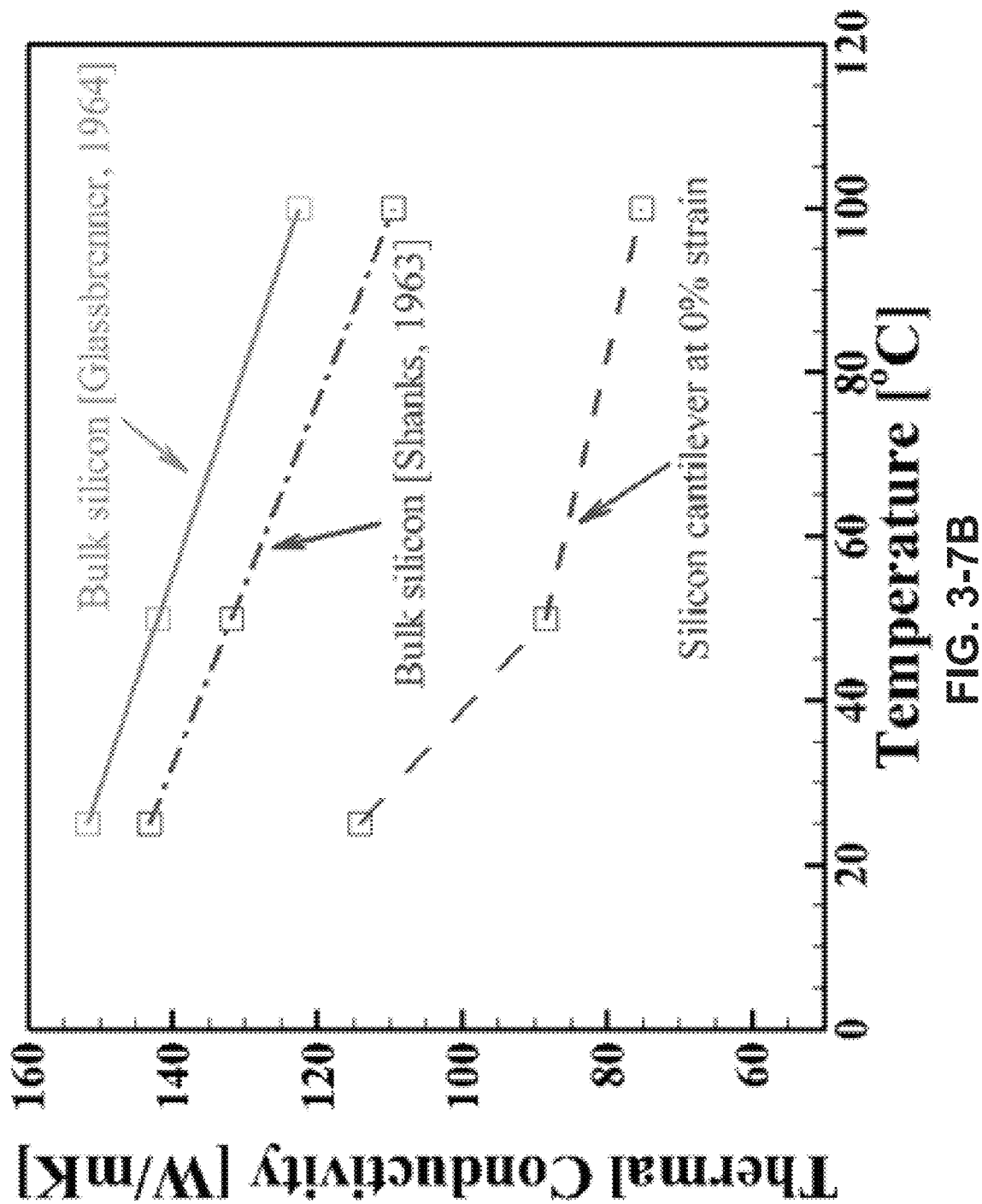
Figures 3, 4, 5, 6, 7, 8, 8A:
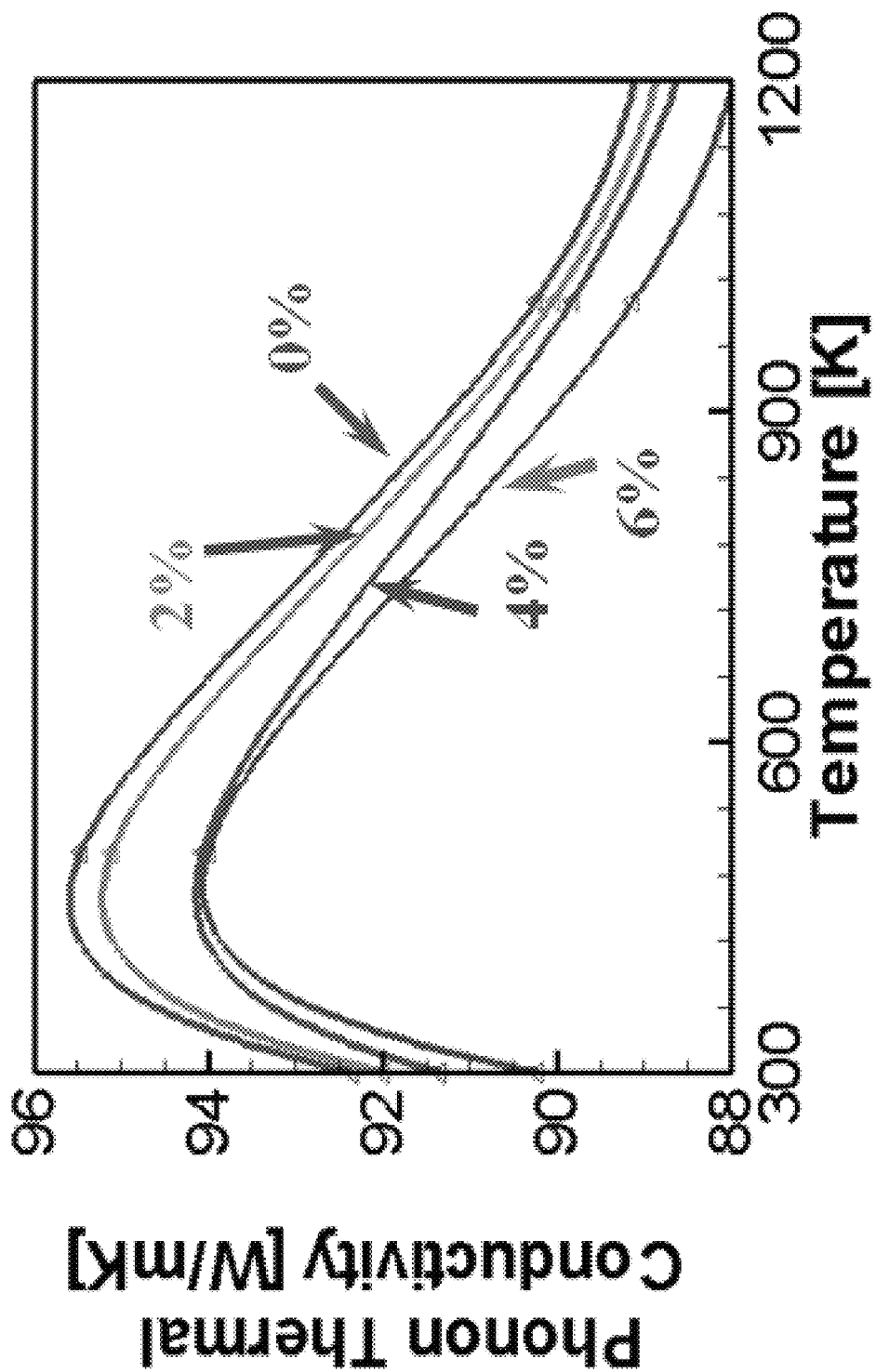
Figures 3, 4, 5, 6, 7, 8, 8B:
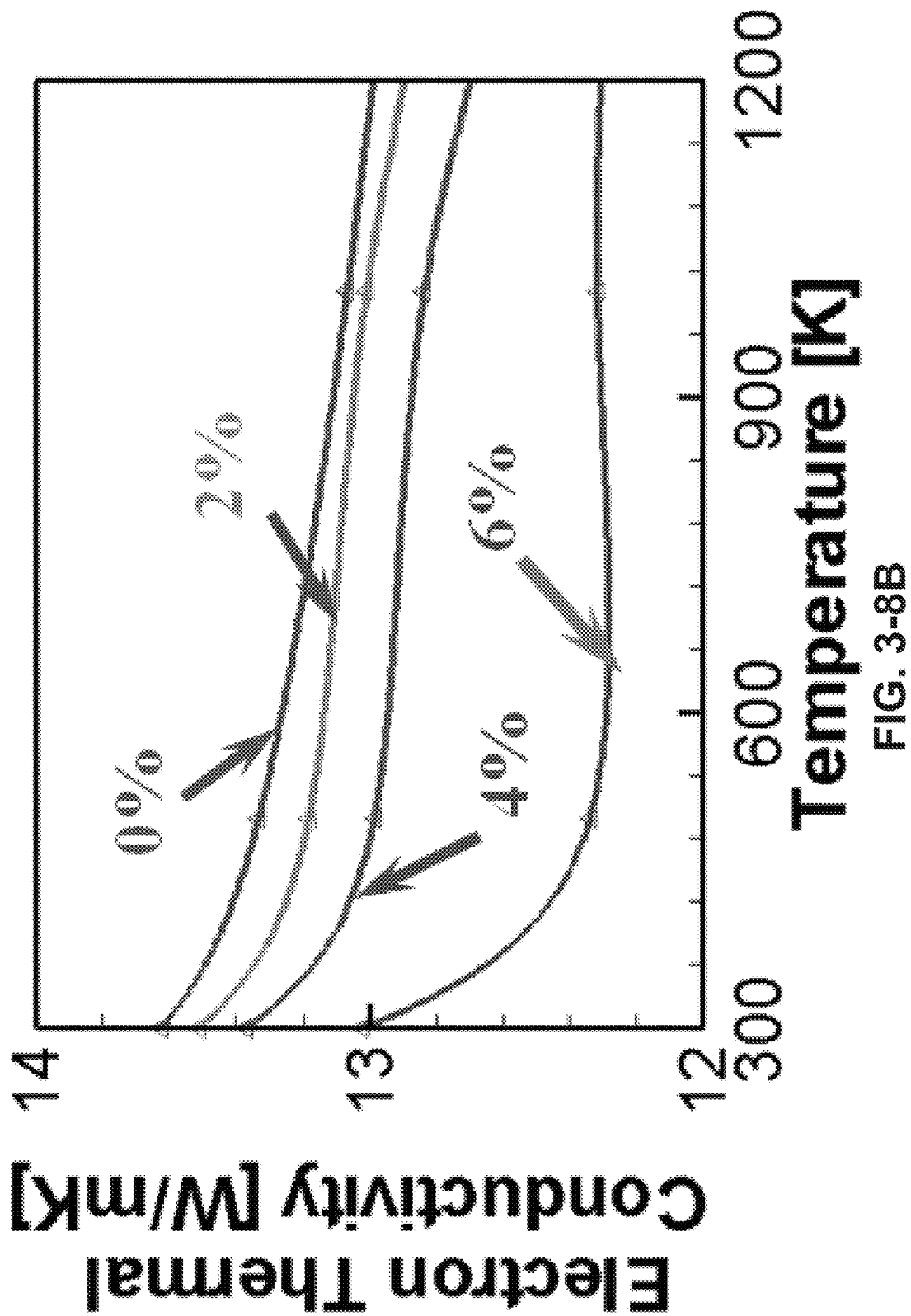

The sample used in this research was Atomic Force Microscope (AFM) cantilever CT170, as shown in FIG. 3-1C. The size of the cantilever is 225 μm by 40 μm by 6.5 μm. All samples have uniform cross sectional area with well characterized surfaces. It is made of highly-doped single-crystalline silicon, with the top surface [100] orientated. The laser used for the Raman spectroscopy setup is 514.5 nm $Ar^+$ laser with a maximum output of 50 mW. The laser was focused and collected using a 40× objective. The Raman spectra were sent to the spectrometer Acton SP2500 manufactured by Princeton Instruments Inc., NJ. The focal length of the spectrograph is 500 mm. The grating of 2400 g/mm was selected for the measurements. The CCD array has the pixel resolution of 1340×100. For the Raman shift measurement of silicon, the peak position of the Raman spectrum is close to 521 nm. The spectrometer scans a range of 15 nm with the center at 521 nm, providing a wavelength resolution of about 0.011 nm.

The thermal conductivity measurement of the silicon sample measuring the surface temperature using Raman spectroscopy. Due to anharmonic terms in the vibrational potential energy, the Raman shift of pure materials is affected by temperature. For non-doped single-crystalline silicon with (111) face perpendicular to the incident beam, a function to describe the relationship between Raman shift and temperature of the sample is given as $$\omega(T) = \overline{\omega}_0 + C\left(1 + \frac{2}{e^x - 1}\right) + D\left(1 + \frac{3}{e^y - 1} + \frac{3}{(e^y - 1)^2}\right), \quad (3\text{-}2)$$

$$x = \frac{hc\overline{\omega}_0}{2k_BT}, \quad (3\text{-}3)$$

$$y = \frac{hc\overline{\omega}_0}{3k_BT},$$

where ω is the Raman shift in frequency/wavenumber; $\overline{\omega}_0$, C and D are constants; h is Planck's constant; c is the speed of light; $k_B$ is the Boltzmann constant and T is the absolute temperature. This function fits well with experimental data obtained between 5 K and 1400 K. A more accurate relationship between the Raman shift of silicon and temperature in the temperature range of 20° C. and 300° C. given as $$\frac{d\omega}{dT} = -0.022 \pm 0.001 \text{ cm}^{-1}K^{-1}. \quad (3\text{-}4)$$

This relationship is applicable to bulk silicon, as well as silicon nanowires. Eq. (3-4) is the main relationship used in this research to derive the temperature of the sample from measured Raman shift. As discussed before, the temperature of the sample surface can be detected by Raman spectroscopy. Using the absorbed laser energy by the sample and the corresponding temperature increase of the laser spot on the sample, the thermal conductivity of the sample can be derived with proper heat transfer model. Depending on the relative size of the sample dimension to the laser spot, the heat conduction models could be different. The laser spot size in this research is between 3.5 μm and 4.5 μm, which is comparable to the thickness of the silicon sample. The diagram of the laser heating on the sample, and the corresponding coordinate system used in the following analysis are shown in FIG. 3-2.

The intensity of the laser follows Gaussian distribution in the radial direction, which is described by Eq. (3-5), $$I(r) = \frac{2P}{\pi r_0^2}\exp\left(-\frac{2r^2}{r_0^2}\right) \quad (3\text{-}5)$$

where $r_0=d/2$ is the radius of the laser spot; P is the laser power. For steady state heat transfer in cylindrical coordinate system, the general heat transfer equation is given as, $$\frac{1}{r}\frac{\partial}{\partial r}\left(kr\frac{\partial T}{\partial r}\right) + \frac{1}{r^2}\frac{\partial}{\partial \phi}\left(k\frac{\partial T}{\partial \phi}\right) + \frac{\partial}{\partial z}\left(k\frac{\partial T}{\partial z}\right) = 0, \quad (3\text{-}6)$$

where k is the thermal conductivity. To obtain an analytical solution to Eq. (3-6), k is taken to be homogeneous in the following analysis. The sample thickness δ is comparable to the laser spot size, while the width of the sample is one magnitude higher than the laser spot size. Therefore, the temperature distribution is not changing in the φ direction. φ can be eliminated from Eq. (3-6). In order to achieve homogeneous boundary conditions, the temperature is normalized using $t(r,z)=T(r,z)-T_s$, where $T_s$ is the surrounding temperature. Further normalize Eq. (3-6) using $s=r/r_0$, and take t(r,z) as θ(s,z). Now Eq. (3-6) becomes, $$\frac{\partial^2 \theta(s,z)}{\partial s^2} + \frac{1}{s}\frac{\partial \theta(s,z)}{\partial s} + r_0^2\frac{\partial^2 \theta(s,z)}{\partial z^2} = 0 \quad (3\text{-}7)$$

By assuming that the temperature gradient of the sample does not change when $r \leq 10r_0$ (corresponding to s≤10), the boundary conditions are $$\frac{\partial \theta(s,z)}{\partial z} = f(s) - \frac{I(s)}{k} = -\frac{2P}{k\pi r_0^2}\text{Exp}(-2s^2) \quad (3\text{-}8)$$

$$-k\frac{\partial \theta(s,z)}{\partial z} - h\theta(s,z) = 0, \quad (3\text{-}9)$$

when z = δ

θ(s, z) is finite, (3-10)

when s = 0

$$\frac{d\theta(s,z)}{dd} = 0, \quad (3\text{-}11)$$

when s = 10

Here, h in Eq. (3-9) is the natural convection cooling coefficient in the air. Since the governing equation and the boundary conditions are all linear, the method of separation of variables could be applied. The temperature at the laser spot could be measured, which corresponds to t(r,z) at z=0. The average temperature at the laser spot is expressed by $$\bar{t} = \frac{1}{\pi r_0^2} \int_0^{r_0} t(r,0) 2\pi r \, dr. \quad (3\text{-}12)$$

Here, $$\bar{t} = -\frac{4P}{k\pi r_0} \sum_{n=1}^{\infty} \frac{J_1(\lambda_n)}{N_n \lambda_n^2} \quad (3\text{-}13)$$

$$\frac{\left(1 - \frac{hr_0 + k\lambda_n}{hr_0 - k\lambda_n} \text{Exp}\left(\frac{2\delta\lambda_n}{r_0}\right)\right)}{\left(1 + \frac{hr_0 + k\lambda_n}{hr_0 - k\lambda_n} \text{Exp}\left(\frac{2\delta\lambda_n}{r_0}\right)\right)} \int_0^1 \text{Exp}(-2s'^2) J_0(\lambda_n s') s' \, ds'.$$

Eq. (3-13) relates the measured surface temperature $\bar{t}$ to the thermal conductivity k of the material. But in real practice, the equation needs to be truncated to solve the value of k. FIG. 3-3 shows the value of each item in the summation and also the overall value of $\bar{t}$ as a function of n, with assumed value of the thermal conductivity. As shown in FIG. 3-3, the first 15 items dominate the value of $\bar{t}$. The items starting from the 16th were truncated in the calculation process.

For the measurements at about 300° C., the temperature resolution of the equipment is about 2° C., which means the temperature change within 2° C. will not be detected by the Raman spectroscopy method. However, this temperature change may be detected by the RTD sensor, which has a resolution of 0.1° C. For the thermal conductivity measurement using Raman thermometry, the localized temperature increase at the laser spot is required. The laser power should be high enough to create a temperature increase of at least 2° C. for the system to detect it.

The Raman peaks that can be observed depend on the polarization of the laser and the orientation of the silicon crystal. The silicon cantilevers used in this research have the top surface [100] oriented, and the side surface [011] oriented. The uniaxial load was applied to the cantilever in the [01$\bar{1}$] direction. The laser was focused onto the [100] surface and backscattered from the same surface. According to the Raman selection rule, the third polarized phonon would be observed.

The CCD camera of the Raman spectrometer captures the Raman spectra using discretized pixels. A difference of 0.03 nm in Raman peaks corresponds to a stress difference of more than 300 MPa. The accuracy of the Raman peak detection can be improved by fitting the Raman shift spectrum with proper fitting function. The Gaussian profile was shown to fit with the least error. The peak position of the fitted Gaussian curve was used for subsequent calculation. With the assistance of Raman curve fitting, the wavenumber resolution is about 0.037 cm$^{-1}$. To further improve the Raman shift measurements, for each capture of the Raman shift signal, the laser line was also scanned.

In the experiments, the stress-induced Raman shift was examined at different temperatures. Low laser power was applied as not to create detectable localized temperature increase on the sample surface. The temperature was chosen as 25° C., 50° C. and 100° C. The strain levels are 0%, 0.05%, 0.1%, 0.2%, and 0.25%. The measurements were also performed at high laser power to create temperature increase on the sample surface for thermal conductivity measurement. For each set of measurement, 5 to 10 repeated tests were performed. The integration of a Raman spectrum usually took less than 10 s. The integration time of the Raman spectra was taken as 10 s.

As shown in FIG. 3-3, uniaxial mechanical loading was applied to silicon samples along their axes. The surface stress measurements were performed at the load values which were kept constant at specified levels.

In order to achieve optimized Raman signal intensity and for control of the absorbed laser power, the laser spot size on the sample surface should be determined. The laser spot size is affected by focusing distance and by the quality of incident laser beam. Therefore, the laser spot size needs to be determined for each measurement. One way to obtain the spot size is to scan across a cleaved edge. In this research, the laser spot size was found to in the range of 3.5 μm to 4.5 μm with a 40× objective. Researchers have shown a laser spot size of less than 1 μm with a 100× objective. The absorbed laser power P is determined by measuring laser power at different points of the optical path as shown in the FIG. 3-4-2A. When the output laser intensity from the Ar$^+$ laser machine was stable, the laser power at different locations shown in FIG. 3-4-2A was measured using a power meter (S140C+PM100USB, Thorlabs Inc., NJ). The total laser power $I_A$ coming out from the fiber end was mostly reflected by the dichroic mirror. A portion of $I_A$ gets transmitted through the dichroic mirror, noted as $I_C$. In the experiments, $I_C$ is the only "free end" of the optical path. $I_E$ represents the laser power delivered to the sample. The absorbed laser power is the difference between $I_E$ and the reflected portion. The reflected laser power from the sample surface was derived from $I_D$ after taking into account the transmission ratio of the objective and the dichroic mirror. The final relationship between the absorbed laser power $I_{AB}$ and $I_C$ is represented as, $$\frac{I_{AB}}{I_C} = \frac{I_C \times I_E^2 - I_A \times I_B \times I_D}{I_C \times I_C \times I_E} = a. \quad (3\text{-}14)$$

In Eq. (3-14), the ratio is a constant a. After calibration at different laser power levels, the value of a was found to be 273±21. For each measurement, the absorbed laser power was calculated as, $$I_{AB} = a \times I_C. \quad (3\text{-}15)$$

The Raman shift of silicon is affected by both temperature and mechanical stress of the sample. The temperature-effect-only Raman shift can be measured without applying mechanical load. However, when the stress-effect-only Raman shift is to be measured, the laser power should be chosen as not to create detectable temperature increase of the sample surface caused by laser heating. Therefore, there is a threshold laser power, above which detectable temperature increase of the sample surface will be created. The threshold laser power was calibrated by setting the sample to a constant temperature (room temperature in this case) and measuring the temperature of the sample surface with different incident laser power using Raman thermometry. The threshold laser power was determined when the temperature measured by Raman thermometry appeared just higher than sample temperature measured by a RTD sensor. In the measurement, the sample was kept at 27° C. The plot of measured temperature by Raman spectroscopy versus absorbed laser power follows a linear pattern, as shown in FIG. 3-4-2B. The data points were fitted linearly. The intersection of the fitted line and the actual temperature line denoted the threshold laser power. In this case, the threshold laser power is about 2.43 mW. Preferably, the laser power should be kept lower than the threshold laser power, when measuring stress-effect-only Raman shift. However, if the laser power is too low, the exposure time for each Raman spectrum increases tremendously (>5 min), which introduces the measurement error of background noise, and vibration of the platform, etc. Therefore, the laser power used in the experiment was kept slightly higher than the threshold laser power, but less than 4 mW. Divided by the laser spot size, this leads to the average laser power density of 0.04~0.10 mW/$\mu m^2$ over the laser spot at the sample surface. The laser density should be less than 2 mW/$\mu m^2$ to avoid detectable temperature increase. The laser they used was 442 nm $Ar^+$ laser. The sample was silicon covered with a thin layer of silicon oxide. For thermal conductivity measurement, maximum laser power was applied to create localized temperature increase on the sample surface, with more than 10 mW of laser power delivered to the sample surface.

The Raman shift of silicon is affected by both temperature and mechanical stress. The thermal conductivity measurement relies on the temperature of the sample surface measured by Raman spectroscopy. In order to obtain the effect of mechanical stress on thermal conductivity, the stress-induced Raman shift and temperature-induced Raman shift are separated. The effect of stress on Raman shift needs to be separated as well. The effect of mechanical stress on Raman shift was obtained by setting the laser power at a low level so that there was no detectable laser heating of the sample. After that the laser power was turned to a higher level to create the localized temperature increase on the sample surface. The difference of these two sets of Raman shift is actually the Raman shift caused by localized temperature increase, which was used to calculate the thermal conductivity.

Figures 1, 2, 3, 4, 5:
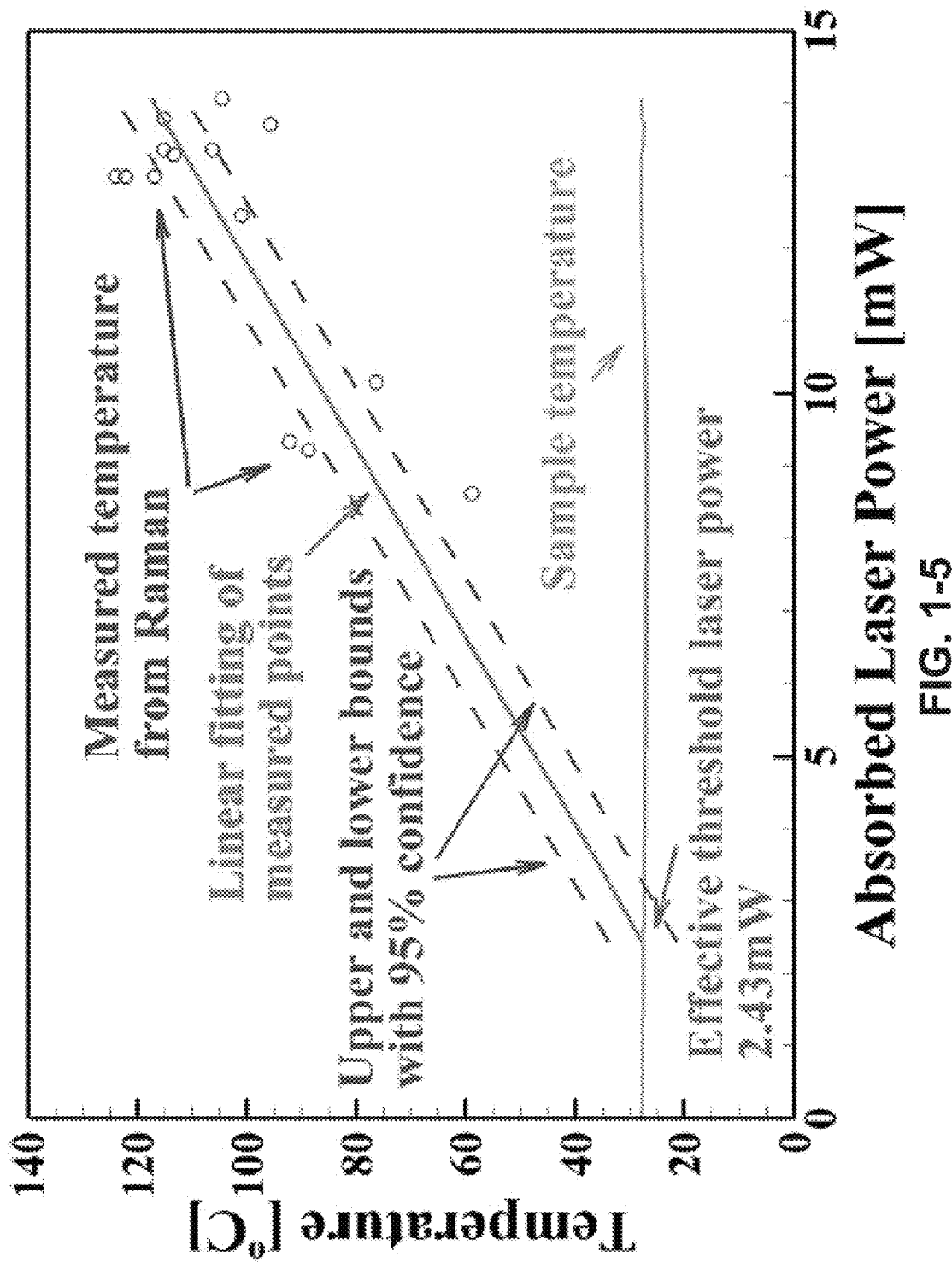
Figures 1, 2, 3, 4, 5, 6, 6A:
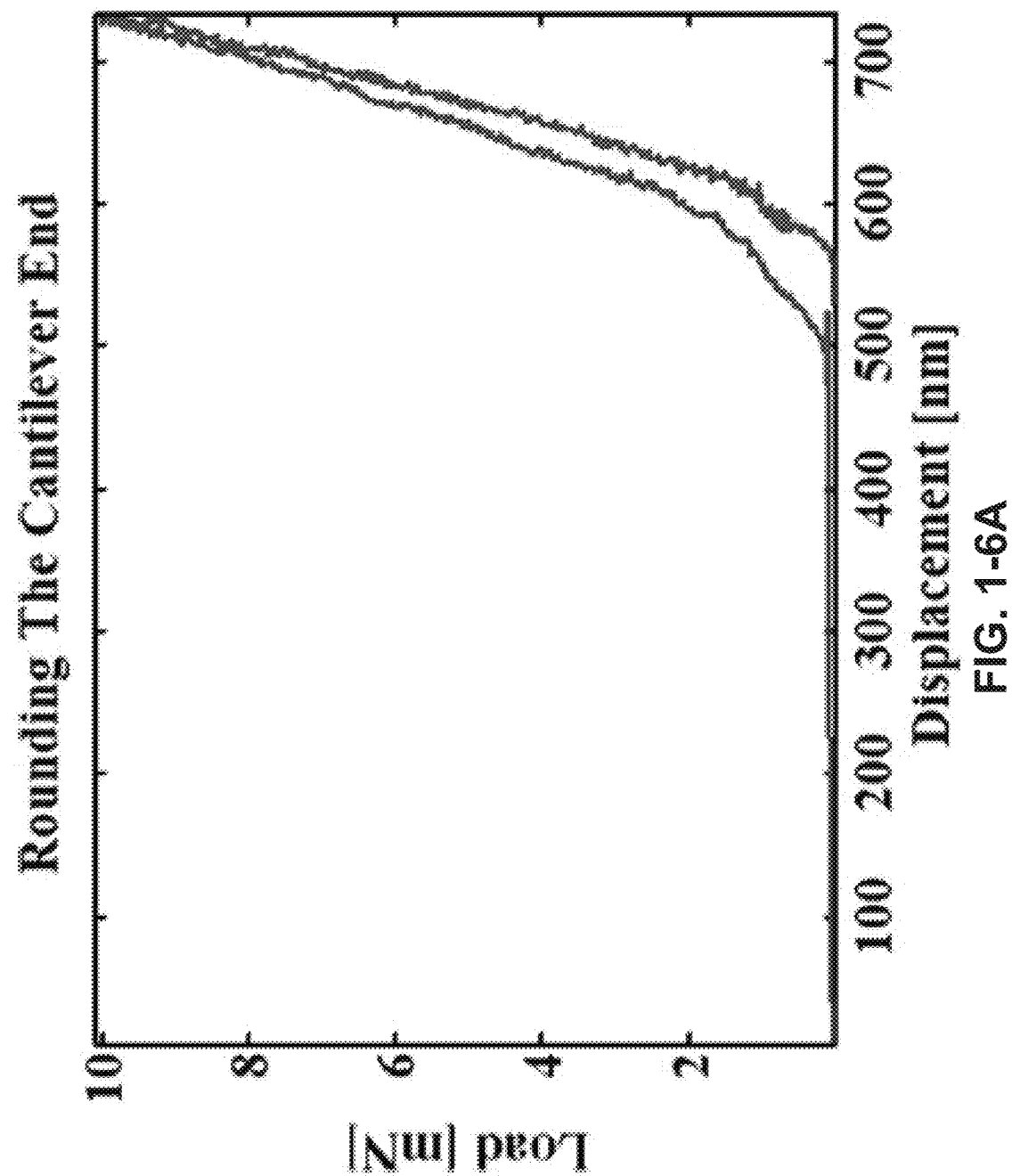
Figures 1, 2, 3, 4, 5, 6, 6B:
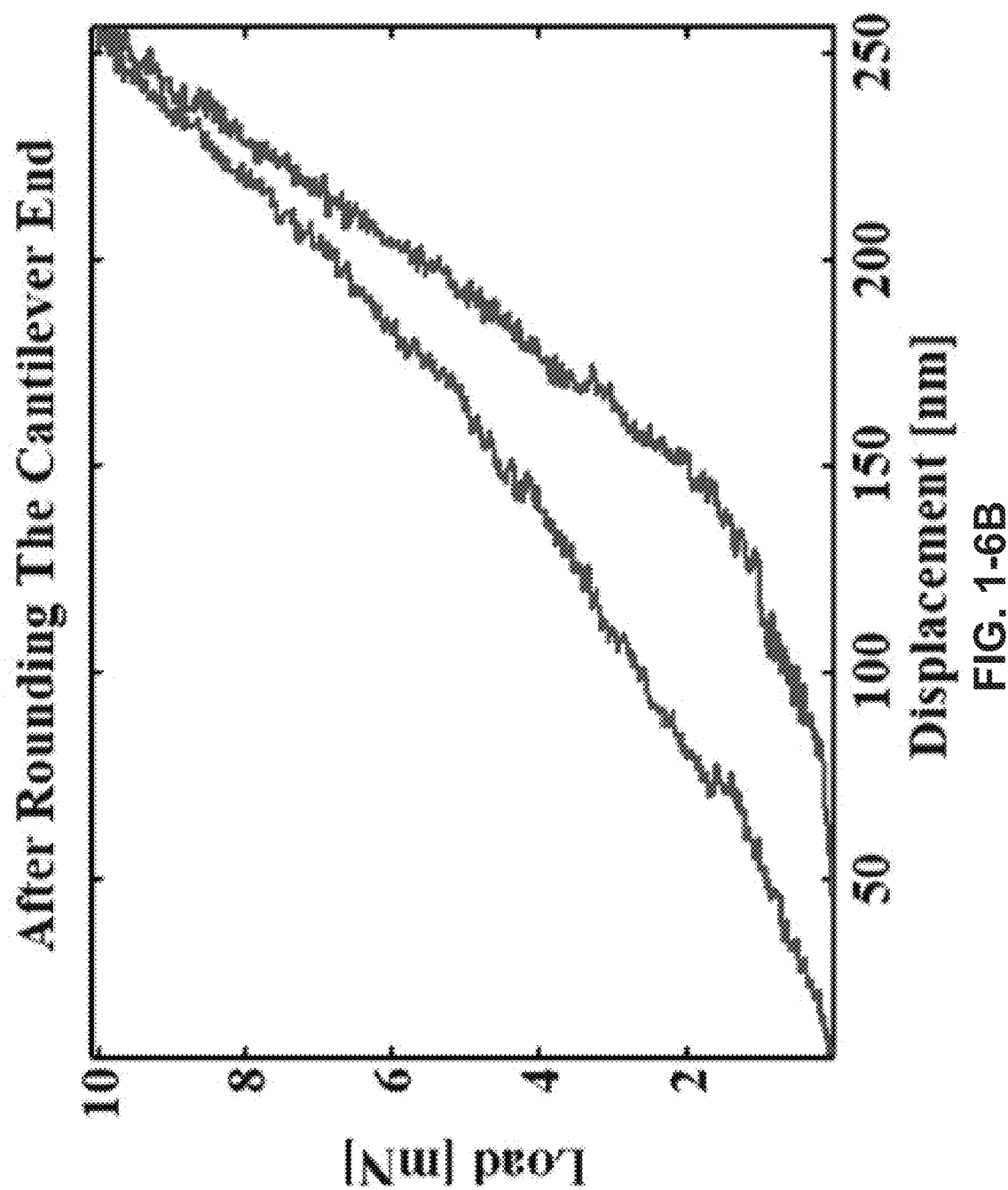
Figures 1, 2, 3, 4, 5, 6, 7, 7A:
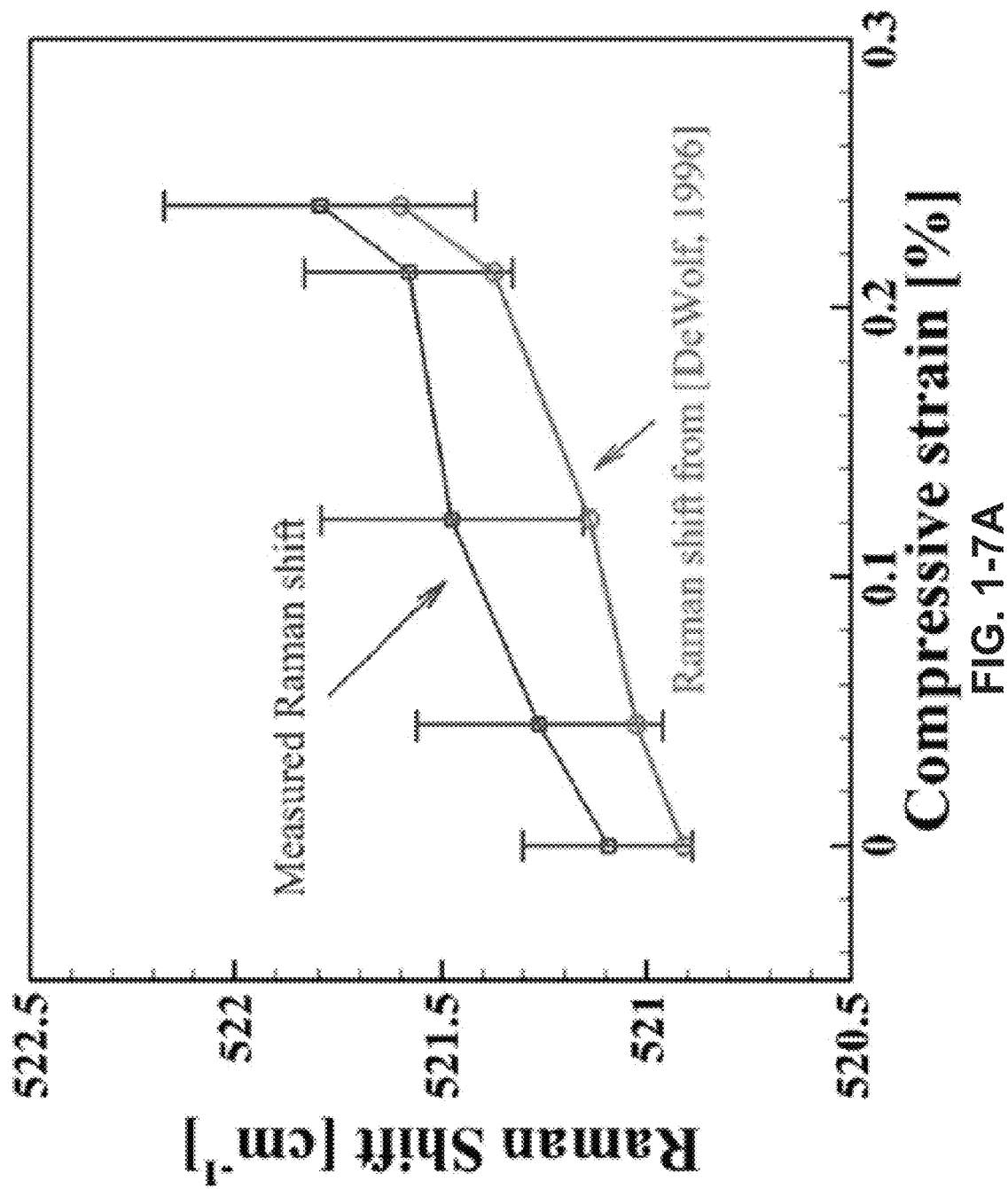
Figures 1, 2, 3, 4, 5, 6, 7, 7B:
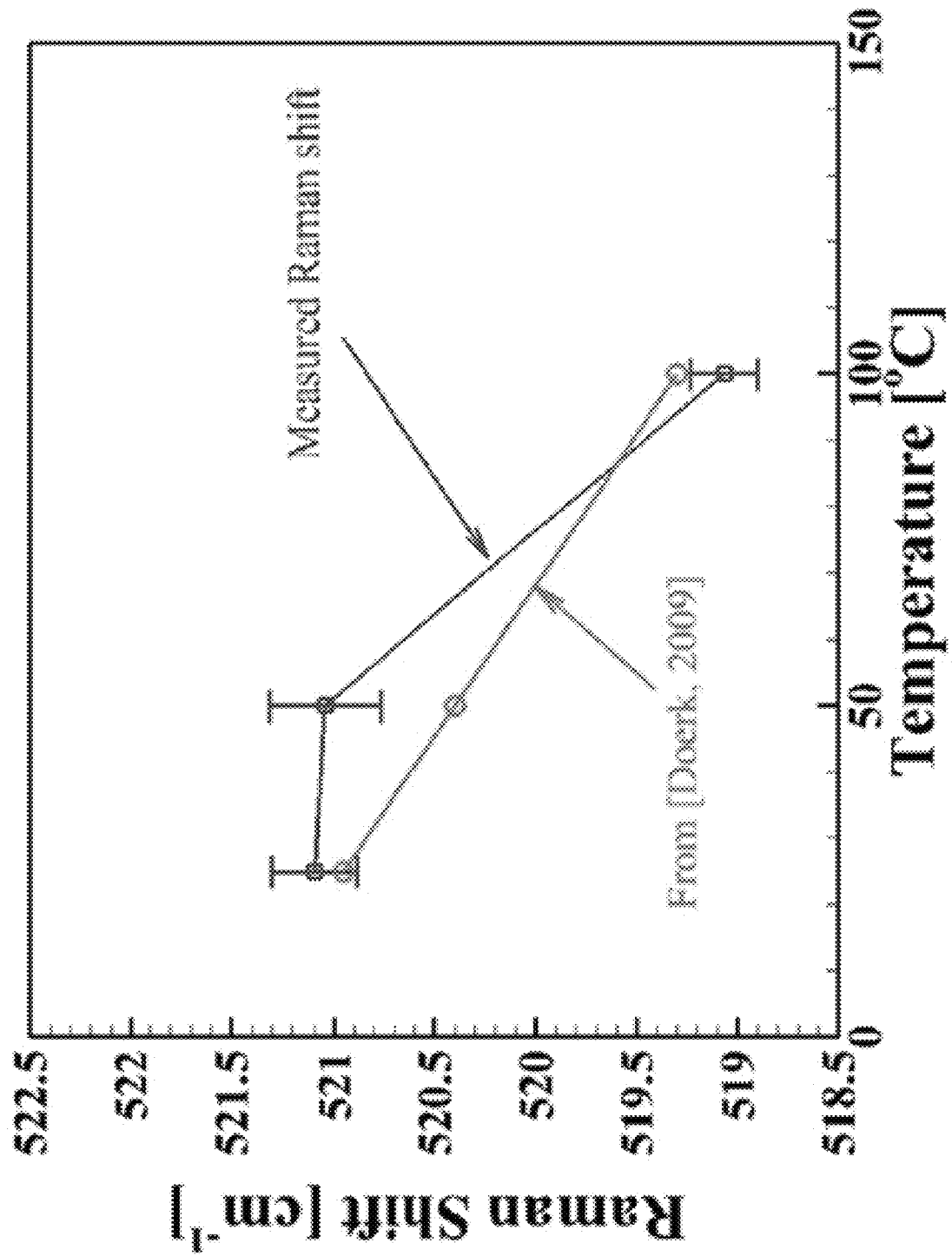
Figures 1, 2, 3, 4, 5, 6, 7, 8, 8A:
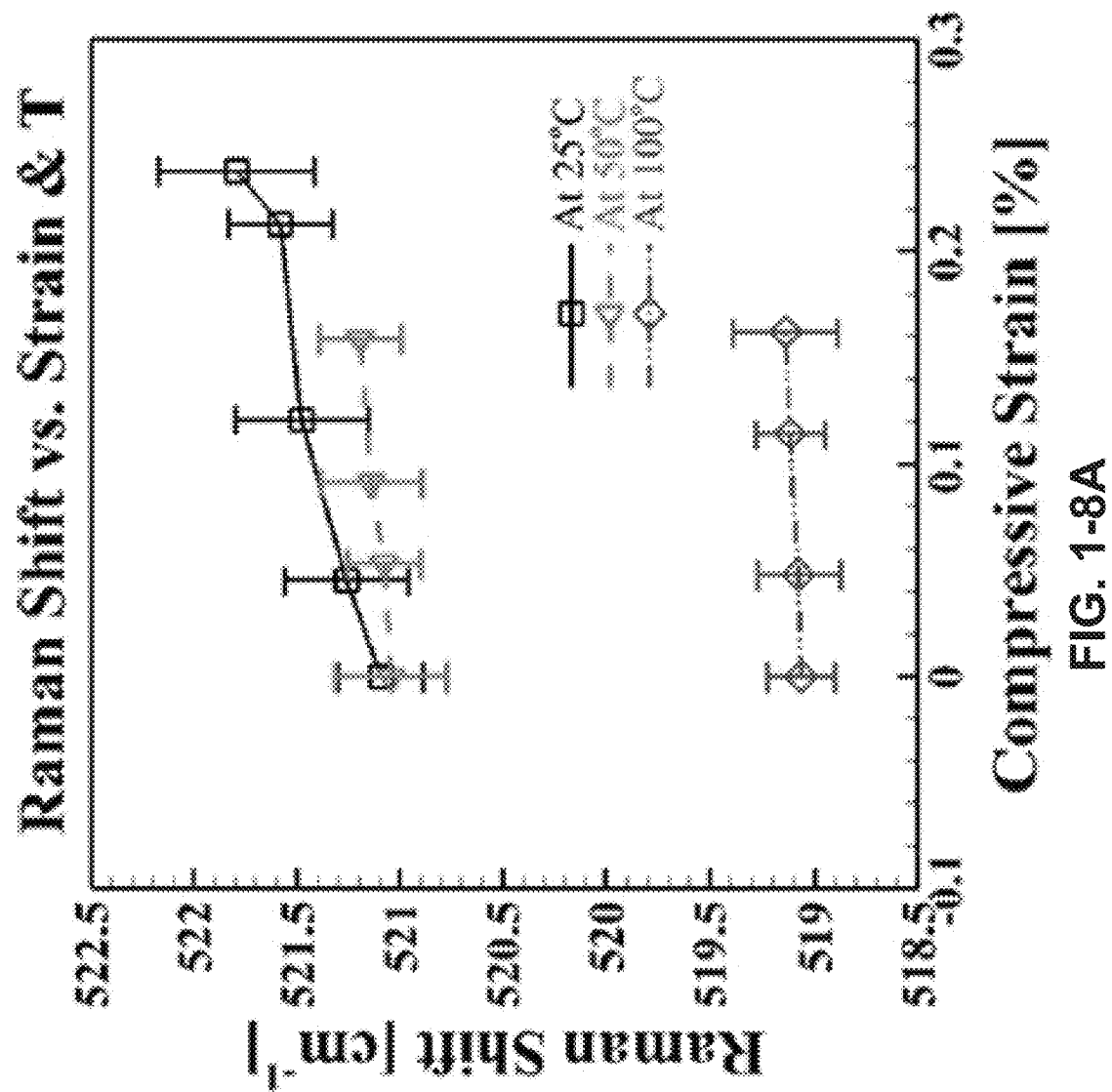
Figures 1, 2, 3, 4, 5, 6, 7, 8, 8B:
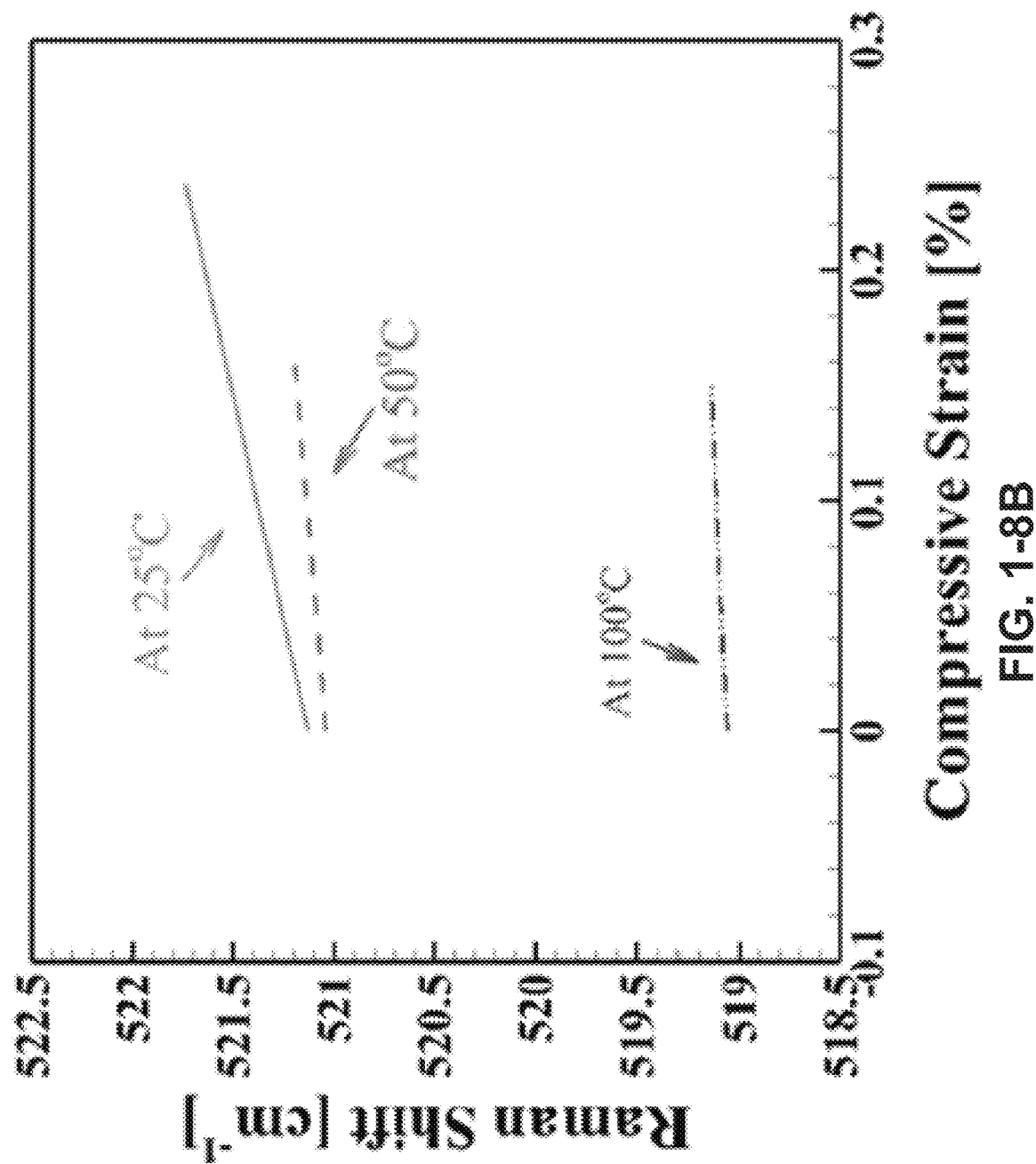
Figures 1, 2, 3, 4, 5, 6, 7, 8, 8C:
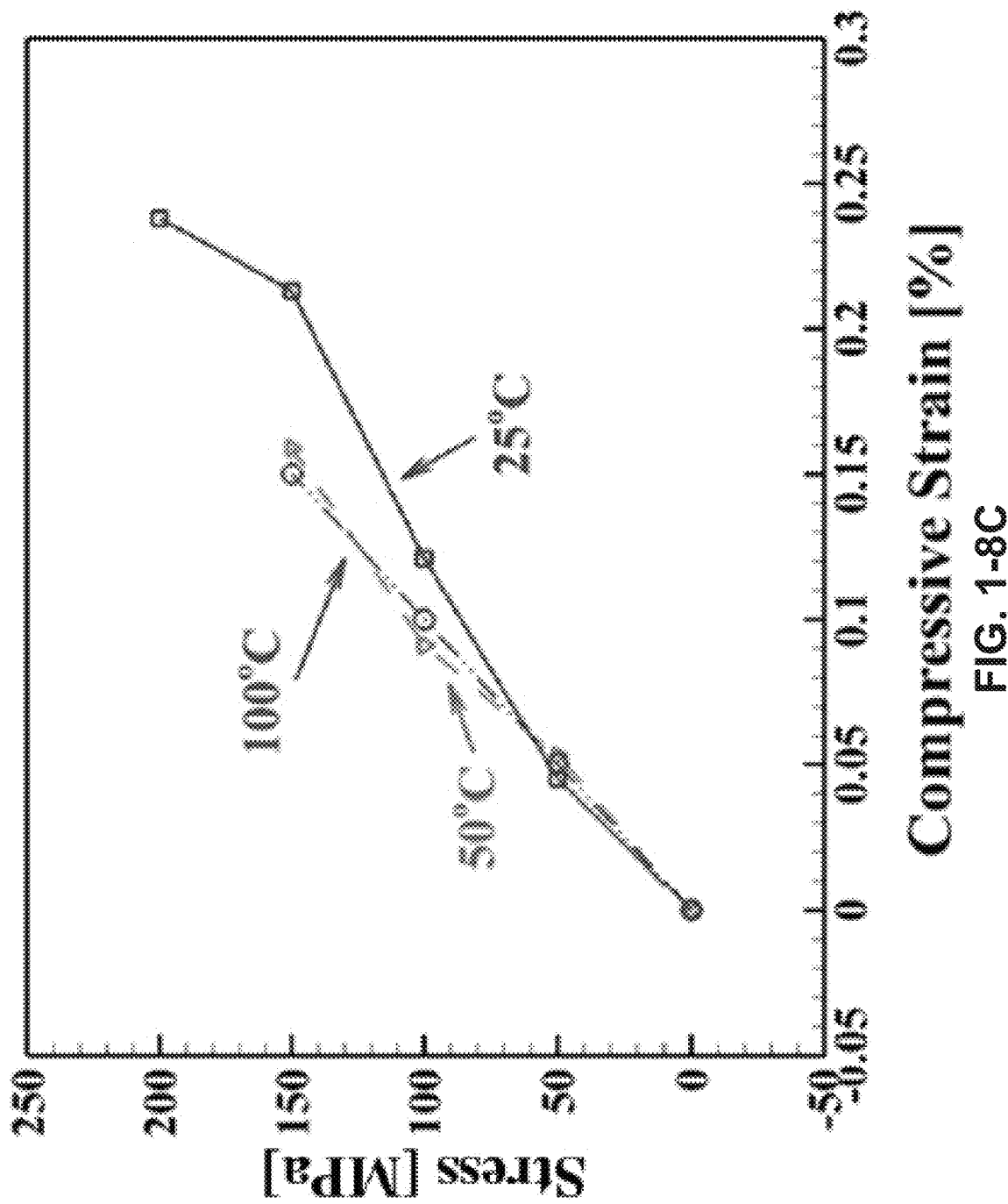

The Raman shift affected by both temperature and mechanical stress is shown in FIG. 3-5. The Raman shift has a generally linear relationship with the compressive strain. The measurement error is relatively low, since the signal to noise ratio is high at high laser power. Compared with the Raman shift without laser heating, the Raman shift with laser heating has lower value, which was caused by the localized temperature increase leading to localized relaxation. At a specific strain level, the difference between these two Raman shift values reveals the localized temperature increase due to laser heating.

This temperature increase is actually $\bar{t}$ in Eq. (3-13). In order to eliminate the calculation error, the subtraction of the Raman shift between the cases with laser heating and without laser heating were not performed directly. As for both cases, the Raman shift follows a linear relationship with respect to the compressive strain, the Raman shift was first fitted as a linear function of the strain, then the Raman shift was subtracted using the fitted values at the strain level of 0%, 0.05%, 0.1%, 0.15%, 0.2% and 0.25%. The resultant Raman shift is shown in FIG. 3-6.

At the lower temperatures of measurement, the temperature increase due to localized laser heating is relatively low, which is caused by relatively higher thermal conductivity at lower temperatures. When the compressive strain increases, the thermal conductivity also increases, which results in even lower localized temperature increase. In addition, the sample absorbed less laser power when the temperature of the sample itself was high, because the high temperature of the sample surface reduced the temperature gradient between the laser spot and other part of the sample. The corresponding thermal conductivity as a function of mechanical stress is shown in FIG. 3-7.

For the thermal conductivity measurement in this research, the error was mainly originated from the signal to noise ratio of the Raman spectra, the stability of the output power of the laser, and the fluctuation of the surrounding temperature. It is possible that some of the results can have a low signal to noise ratio, possibly due to a misaligned optical path and background light. The laser power fluctuates within a small range. Although this fluctuation was monitored and recorded during all experiments, the fluctuation of the laser power can result in an unstable thermal state of the silicon cantilever. Because the heat transfer model is valid for steady state only, the fluctuation of the laser power can cause error to the thermal conductivity measurement. When the laser heating of the cantilever occurs, the localized temperature increase of the cantilever perturbs the air around the cantilever. This may also affect the thermal conductivity measurement. As shown in FIG. 3-7, the thermal conductivity of silicon shows an increase as a function of compressive strain at all temperatures. It also decreases when the overall temperature increases from room temperature to 100° C. At higher temperature, the dependence of the thermal conductivity on the mechanical stress is higher.

An effect of the difference in scales can be highlighted based on the Non-equilibrium Green's Function (NEGF) based approach to calculate strain dependent thermal conductivity of Si at nanoscale, FIGS. 3-8. This simulation used tensile strain. Unlike the compressive strain leading to increase in thermal conductivity, the effect of tensile strain was to reduce thermal conductivity. More importantly, the reduced scale values were in close proximity to the experimental values predicted. This result validates that with reduction in length scale the mean free path for phonons reduces leading to decrease in thermal conductivity values. The length scale of experiments in this work lies just above the MD and quantum values and much below the length scales of various experiments reported.

FIG. 3-8-B shows electronic contributions to thermal conductivity values of Si as a function of strain and temperature. The strain dependent thermal conduction data, however, points to a possible trend. As shown, the contribution of strain is measurable. Invariably, the straining leads to reduction in electronic component. Overall, fundamentally, electron mobility change in correlation with atomic rearrangements significantly affect electron-phonon coupling in response to the applied strain and stress. One simple expression of thermal conductivity from kinetic energy is, $$k = \frac{1}{3} C v_s \Lambda, \quad (3\text{-}16)$$

where k is the thermal conductivity; C is the specific heat; $v_s$ is the average phonon group velocity and $\Lambda$ is the phonon mean free path. As shown here, the thermal conductivity of silicon is linearly dependent on the phonon mean free path, which is an average of a group of free paths of phonon. The way to calculate the average of the free paths is not unique. It depends on the particle energy. Therefore, different values of phonon mean free path of silicon are observed. The phonon mean free path of silicon is 43 nm at room temperature, if not considering the phonon dispersion. The phonon mean free path of single-crystalline thin-film silicon has been reported to be about 300 nm at room temperature.

The phonons in silicon can also be categorized to low-frequency and high-frequency groups. When the temperature is much lower than 650K, low frequency phonons are the main energy carriers. Low frequency phonons have long mean free path, which makes them more sensitive to the dimension of the material. This is exhibited as the size effect on the thermal conductivity. High frequency phonons dominate the heat transfer at higher temperature, because of the large number of high frequency phonons when the temperature is high. The high frequency phonons are sensitive to the point defects and impurities, such as dopants. Low frequency phonons are more sensitive to extended defects and grain boundaries. Therefore, the dopants affect the thermal conductivity of silicon mainly by affecting the high-frequency phonons, while reducing the scale of silicon structures mainly affects the low-frequency phonons.

The mechanical stress affects the thermal conductivity of silicon mainly by affecting the group velocities of mode-specific phonons and also affecting the specific heat. Compressive stress/strain increases the thermal conductivity of silicon, while tensile stress/strain decreases the thermal conductivity. The relationship between the mechanical stress/strain and thermal conductivity follows a linear pattern, which is in accordance to Eq. (3-16). It has been shown in this research that the effect of mechanical stress on thermal conductivity becomes more obvious at higher temperature. This reveals that the mechanical stress/strain mainly affects the group velocities of high-frequency phonons. While the dopants inevitably reduce the thermal conductivity of silicon due to affecting the high-frequency phonons, the mechanical stress and strain can be used to compensate this decrease of thermal conductivity.

Overall, results in this work offer interesting insights into thermomechanical behavior coupling in microscale Si. The load was applied in uniaxial manner and the measured behavior was not affected by in-plane loading artifacts. Increase in temperature leads to stronger thermomechanical coupling. Specific heat of materials has been repeatedly shown to be unaffected by temperatures, until those are in the range of material melting point temperature. Therefore, one possible assumption is that the increase in thermal conductivity is associated with increase in thermal diffusivity with increased mechanical strain. Current high temperature models do not account for change in thermal diffusivity with increasing strain and temperature. The presented work offers that such possibility needs to be taken into account. In the following, a discussion of the results in light of the performed experiments is provided.

While thermal conductivity measurement at micrometer range has been challenging, the measurement at nanometer range is likewise difficult. The resolution of Raman spectroscopy is limited by the wavelength of the incident laser. With shorter wavelength of ultraviolet (UV) light and atomic force microscope (AFM) tip enhancement technology, the spatial resolution of Raman spectroscopy can be as low as 100 nm. However, this scale is still bigger than that of current silicon structures in micro-processors, for which is already lower than 30 nm. For silicon nanowires and nanotubes, the diameter could be less than 15 nm. Measurement of thermal conductivity at such small scale can benefit from fabrication of nano-heaters and nano-sensors with photolithography method, and then bond the nanowire between the nanoscale heater and sensor. Although the resolution of Raman spectroscopy method can only be optimized down to 100 nm, it has the advantage of minimum sample preparation, for which the photolithography method does not have. Therefore, Raman spectroscopy method is still widely used for thermal conductivity measurement at microscale.

The mechanical strain has been demonstrated to have an effect on the thermal conductivity of silicon. Besides mechanical strain, there are other methods available to tune the thermal conductivity of materials, including creating nanostructures and gas passivation.

Nano-structuring has been an effective way to reduce the thermal conductivity of materials. The thermal conductivity of the crystalline structured material can be reduced even lower than that of its amorphous counterpart. It had been believed for a long time that the thermal conductivity of the amorphous structured material is the lower bound of the thermal conductivity for a specific material. This lower bound is called "amorphous limit" or "lower limit". The thermal conductivity of nanostructured material is much lower than its amorphous limit. The nanostructured material can reduce the thermal conductivity of a material by order of magnitudes. Roughened silicon nanowires reduce the thermal conductivity of silicon to 1.6 W/(m·K), which is two magnitudes lower than that at bulk scale. The thermal conductivity can be reduced by 11% to 17% by hydrogen passivation, and 37% to 51% by oxygen passivation.

Mechanical straining is one method of tuning the thermal conductivity of materials. The method of mechanical straining has an advantage of versatility, simplicity and being able to tune the thermal conductivity either up or down. This method is applicable a wide range of materials from bulk scale to nanometer scale. Compared to the nanostructured technology, the mechanical straining method is simpler. It is one of the few methods which can enhance the thermal conductivity of materials.

Embodiments of the present disclosure include devices and methods that measure mechanical properties (e.g., modulus, failure stress, surface stress), thermal properties, crystalline structure, and/or detect elements/components of solid samples in the micrometer to nanometer range/scale, some embodiments combining two or more of these features in one combined test platform or method, and some embodiments simultaneously performing two or more of these features in one combined test platform or method. Further embodiments include devices and methods that perform two or more of these features while a load (which in some embodiments is a uniaxial load) is applied to the sample under test. Yet other embodiments evaluate the properties of the sample as a function of temperature, testing scale, or other conditions, while further embodiments evaluate the interaction/correlation of these properties.

Example materials that may be evaluated by various embodiments of the present disclosure include, for example, metals, ceramics, semiconductors, biomimetic material, and biological materials. Various embodiment perform these functions with the sample under test (which may be a solid) in air or in liquid. Still further embodiments perform these functions at temperatures ranging from room temperature to 1000° C.

Various embodiments of the present disclosure perform in-situ correlation of nonlocal stress and/or applied stress, some embodiments performing these functions while the sample is under a loading condition, some embodiment performing these functions while the sample is under uniaxial loading.

Embodiments of the present disclosure perform in-situ stress and thermal property measurements, some measuring stress-induced thermal conductivity and/or thermal diffusivity changes.

Still additional embodiments perform in-situ stress and crystal structure/orientation measurement, some measuring stress-induced crystal orientation changes.

Alternate embodiments perform mechanical tests, such as nanoindentation, indentation creep, scratch, nano-impact/impulse, and nano-surface profiling. Still other embodiments perform thermal tests, such as thermal conductivity and/or thermal diffusivity measurements. Further embodiments perform Raman spectroscopy tests. And still further embodiments perform two or more of these mechanical, thermal, or spectrographic tests simultaneously and/or with the same device.

Embodiments of the present disclosure measure various mechanical properties and/or thermal properties, which may be performed simultaneously or separately. Example mechanical and thermal properties measured include applied stress, nonlocal stress, overall displacement, elastic modulus, hardness, creep property, scratch resistance, nano-fatigue resistance, nano-scale surface roughness, thermal conductivity, thermal diffusivity. Thermal conductivity and nonlocal stress are example properties that may be measured by Raman spectroscopy in some embodiments.

Solids with one or more flat surfaces are suitable for embodiments that perform nanoindentation and/or Raman spectroscopy. It is advantageous if the samples under test have a Raman effect for Raman-related measurements.

The testing scale of various embodiments is in the sub-micron to tens of microns range.

The working temperature for some embodiments is from 20° C. to 750° C.

The mechanical loading provided by embodiments is adjustable from 0.1 mN (miliNewtons) to 500 mN with a resolution of 0.1 mN.

Embodiments are capable of measuring displacements up to 14 microns, and some embodiments are capable of detecting displacement to a resolution of one nanometer (nm) or smaller.

Various embodiments include an $Ar^+$ laser, example wavelengths being 457.9 nm, 488 nm, and 514.5 nm.

Some embodiments utilize a multi-line laser.

Laser output power can range from 8 mW to 150 mW. Example laser output power is 8 mW for 457.9 nm lasers, 40 mW for 488 nm lasers, 50 mW for 514.5 nm lasers, and 150 mW for Multi-Line lasers.

Embodiments utilize a spectrometer with a scanning range of 0 to 1000 nm.

The resolution of the spectrometer will typically depend on the particular type of excitation laser, diffraction grating, and line fitting technique used. Embodiment of the present disclosure have a resolution of 0.1 $cm^{-1}$.

Reference systems that may be used herein can refer generally to various directions (e.g., upper, lower, forward and rearward), which are merely offered to assist the reader in understanding the various embodiments of the disclosure and are not to be interpreted as limiting. Other reference systems may be used to describe various embodiments, such as referring to the direction of projectile movement as it exits the firearm as being up, down, rearward or any other direction.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. A method for measuring mechanical properties of a microscale or nanoscale structure, comprising:
    supporting an elongate structure at one end, the opposite end being free;
    heating the structure;
    applying a load to the free end;
    receiving energy reflected from the loaded structure while the loaded structure is being heated; and
    measuring a Raman shift in the reflected energy;
    determining a stress in the heated and loaded structure from the Raman shift.

2. The method of claim 1, comprising:
    illuminating the structure with a laser.

3. The method of claim 1, which further comprises determining a temperature of the structure from the energy received from the structure, wherein said determining a stress and said determining a temperature of the structure is from the energy received from the heated and loaded structure.

4. The method of claim 1, wherein said determining includes:
    measuring the Raman shift difference $\Delta\omega_m$; and
    calculating stress components σij.

5. The method of claim 1, wherein said determining includes determining the stress distribution below the surface of the structure.

6. The method of claim 3, wherein said determining includes determining the thermal conductivity of the structure.

7. An apparatus for measurement of stress and temperature of a nanoscale or microscale structure, comprising:
    a load cell configured and adapted to impart an axial compressive load to a nanoscale or microscale structure;
    an electronic heater adapted and configured to heat the nanoscale or microscale structure by conduction while the nanoscale or microscale structure is being axially loaded;
    a receiver configured and adapted to receive reflected energy from the nanoscale or microscale structure while the structure is being illuminated with laser energy; and
    a processor connected to said receiver, the processor configured and adapted to detect a Raman shift in the received reflected energy, and
    determine a stress and a temperature of the nanoscale or microscale structure from the Raman shift.

8. The apparatus of claim 7, comprising:
    a laser, the laser configured and adapted to impart laser energy to the structure.

9. The apparatus of claim 7, wherein the processor determines at least one stress and at least one temperature of the structure from the same reflected energy.

10. The method of claim 1 wherein the elongate structure has an axis extending from the one end to the opposite end, and said applying a load is a compressive load in the direction of the axis.

11. The method of claim 1 wherein said heating is with an electronic heater in contact with a surface of the elongate structure.

12. The method of claim 11 wherein the surface is an end of the elongate structure.

13. The method of claim 1 wherein said heating is with a pair of electronic heaters, each heater being in contact with a different end of the elongate structure.

14. The method of claim 1 which further comprises illuminating a surface of the elongate structure with a laser, and said receiving energy is energy from the laser.

15. The method of claim 1 wherein the applied load is more than about one-tenth of a milliNewton and less than about five hundred milliNewtons.

16. The method of claim 1 which further comprises determining a temperature of the loaded structure from the Raman shift.

17. The method of claim 1 wherein the applied load is a compressive load.

18. The method of claim 17 wherein said heating is with an electronic heater in contact with a surface of the elongate structure.

19. The method of claim 18 which further comprises determining a temperature of the loaded structure from the Raman shift.

20. The method of claim 1 wherein the applied load is less than about five hundred milliNewtons.

21. The method of claim 7 wherein the nanoscale or microscale structure has an axis extending from the one end to the opposite end, and said load cell imparts the axial load to the one end.

22. The method of claim 21 wherein the structure is supported in cantilevered manner, and the one end is the free end.

23. The method of claim 7 wherein said heater is a first heater, and which further comprises a second electronic heater adapted and configured to heat the nanoscale or microscale structure by conduction, said first heater and said second heater being located on opposite sides of the nanoscale or microscale structure.

24. The method of claim 7 which further comprises a laser configured and adapted to illuminate the structure.

25. The method of claim 7 wherein said load cell is configured and adapted to impart a load of more than about one-tenth of a milliNewton and less than about five hundred milliNewtons.

26. The method of claim 7 wherein said load cell is adapted and configured to impart the axial compressive load to the free end of a cantilevered nanoscale or microscale structure.

27. The method of claim 26 wherein said load cell is configured and adapted to impart a load less than about five hundred milliNewtons.

28. The method of claim 27 wherein said heater is a first heater, and which further comprises a second electronic heater adapted and configured to heat the nanoscale or microscale structure by conduction, said first heater and said second heater being located on opposite sides of the nanoscale or microscale structure.

* * * * *